United States Patent [19]

Ando et al.

[11] Patent Number: 5,512,821
[45] Date of Patent: Apr. 30, 1996

[54] METHOD AND APPARATUS FOR MAGNETICALLY DETECTING DEFECTS IN AN OBJECT, WITH COMPENSATION FOR MAGNETIC FIELD SHIFT BY MEANS OF A COMPENSATING COIL

[75] Inventors: Seigo Ando; Yasuhiro Matsufuji; Hiroshi Maki; Mamoru Inaba; Kenichi Iwanaga; Atsuhisa Takeoshi; Masaki Takenaka, all of Tokyo, Japan

[73] Assignee: NKK Corporation, Tokyo, Japan

[21] Appl. No.: 974,585

[22] PCT Filed: Feb. 24, 1992

[86] PCT No.: PCT/JP92/00191

§ 371 Date: Feb. 1, 1993

§ 102(e) Date: Feb. 1, 1993

[87] PCT Pub. No.: WO92/21964

PCT Pub. Date: Dec. 10, 1992

[30] Foreign Application Priority Data

Jun. 4, 1991 [JP] Japan ................. 3-132911
Jul. 16, 1991 [JP] Japan ................. 3-175488
Dec. 3, 1991 [WO] WIPO ........... PCT/JP91/01685

[51] Int. Cl.⁶ ..................... G01R 39/02; G01N 27/72
[52] U.S. Cl. ................. 324/225; 324/240; 324/244; 361/146
[58] Field of Search ..................... 324/225, 234, 324/235–243, 262, 226, 227, 229–231, 261; 361/143, 146, 267, 149; 72/10, 11

[56] References Cited

U.S. PATENT DOCUMENTS

| | | | |
|---|---|---|---|
| 4,510,447 | 4/1985 | Moyer | 324/240 X |
| 4,564,809 | 1/1986 | Huschelrath et al. | 324/240 X |
| 4,823,081 | 4/1989 | Geisler | 324/225 |
| 4,944,028 | 7/1990 | Iijima et al. | 324/225 X |

FOREIGN PATENT DOCUMENTS

| | | | |
|---|---|---|---|
| 51-63666 | 6/1976 | Japan . | |
| 61-119760 | 7/1986 | Japan . | |
| 61-147158 | 7/1986 | Japan . | |
| 61-170068 | 10/1986 | Japan . | |
| 61-277051 | 12/1986 | Japan . | |
| 63-96547 | 4/1988 | Japan . | |
| 63-107849 | 7/1988 | Japan . | |
| 1-134238 | 5/1989 | Japan . | |
| 1-148856 | 10/1989 | Japan . | |
| 0739387 | 6/1980 | U.S.S.R. | 324/225 |
| 0974240 | 11/1982 | U.S.S.R. | 324/225 |
| 1527567 | 12/1989 | U.S.S.R. | |

*Primary Examiner*—Sandra L. O'Shea
*Assistant Examiner*—J. M. Patidar
*Attorney, Agent, or Firm*—Frishauf, Holtz, Goodman, Langer & Chick

[57] ABSTRACT

A magnetic detector includes a magnetizer generating a magnetic field; a first magnetic sensor for detecting a leakage flux resulting from a magnetically defective portion of an object moving in and relative to the magnetic field; a low-pass filter for extracting a low-frequency signal component contained in the signal output by the magnetic sensor, the low-frequency signal component being indicative of a floating flux which crosses the magnetic sensor and is a result of the object moving through the magnetic field; an amplifier for amplifying the extracted low-frequency signal component; a compensating coil excited by the amplified low-frequency signal component output by the amplifier, for generating a magnetic flux which cancels out the floating flux crossing the magnetic sensor; a high-pass filter for extracting a signal resulting from the magnetically defective portion and contained in the signal that is output by the first magnetic sensor; an output amplifier for amplifying a signal output by the high-pass filter to produce a defect signal; a second magnetic sensor located near the first magnetic sensor, for detecting a component of the magnetic field which is parallel to the surface of the object; an amplifier control circuit for controlling an amplification factor of the output amplifier in accordance with a signal from the second magnetic sensor; and a magnetizer control circuit for controlling the intensity of the magnetic field generated by the magnetizer, in accordance with a signal output by the second magnetic sensor.

28 Claims, 40 Drawing Sheets

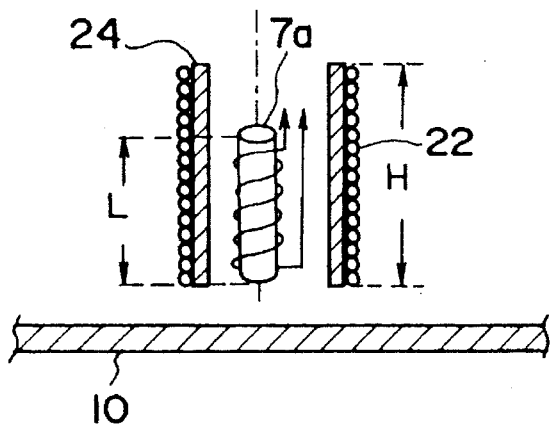 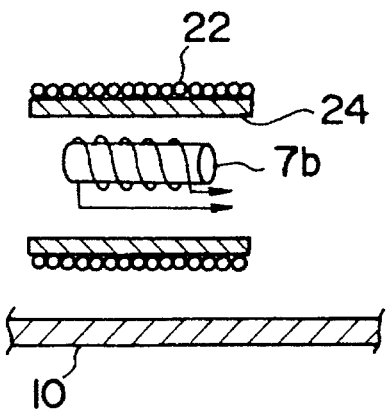
FIG. 6A  FIG. 6B
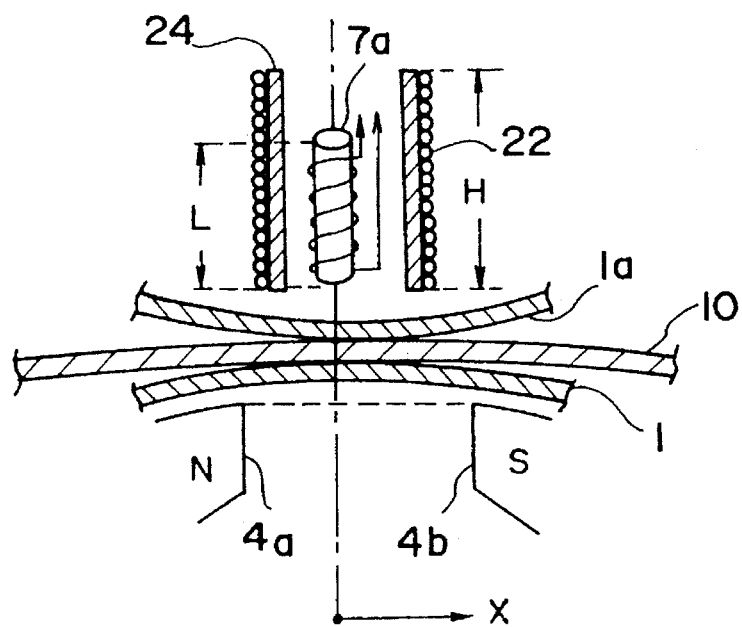
FIG. 6C

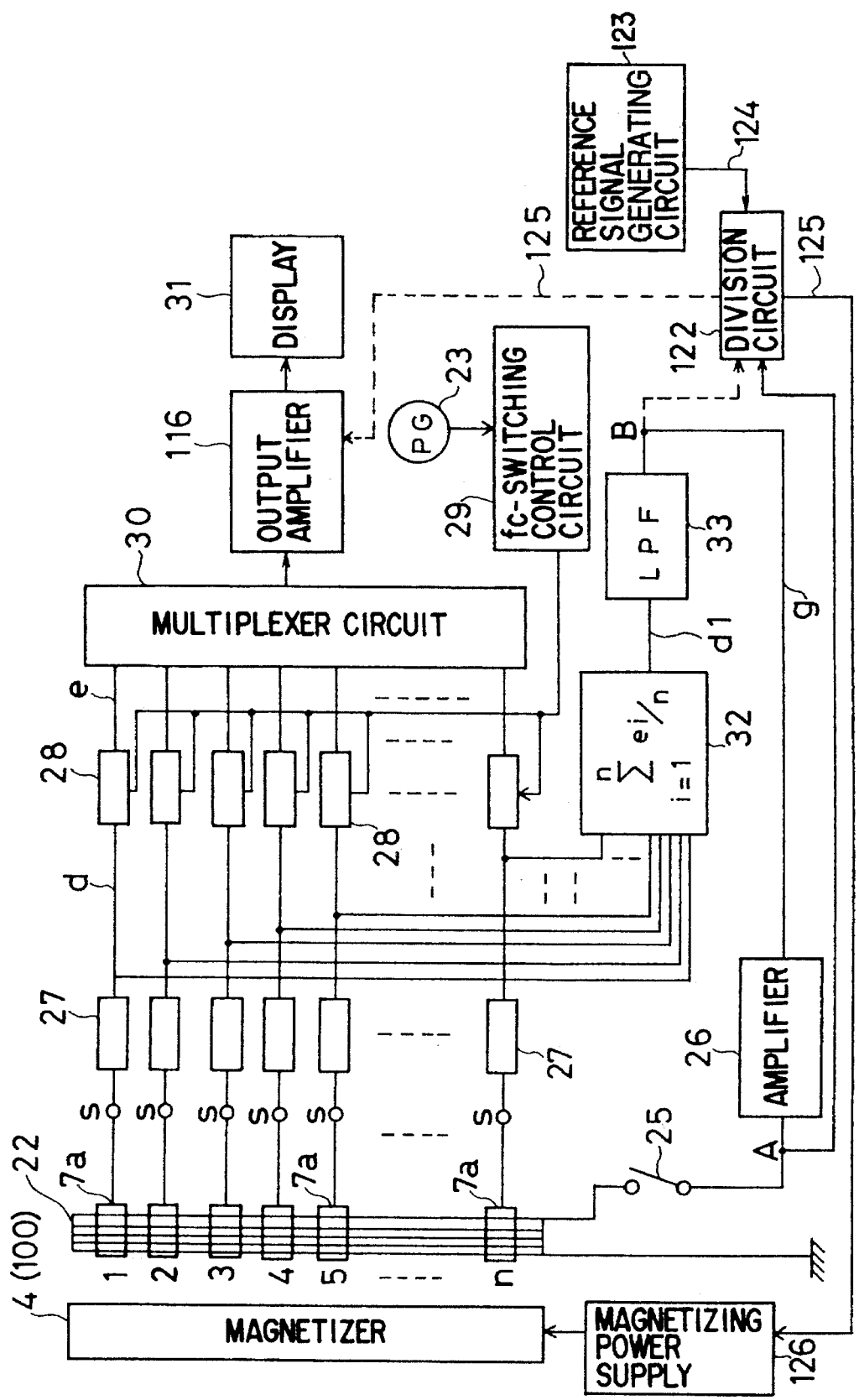
F I G. 31

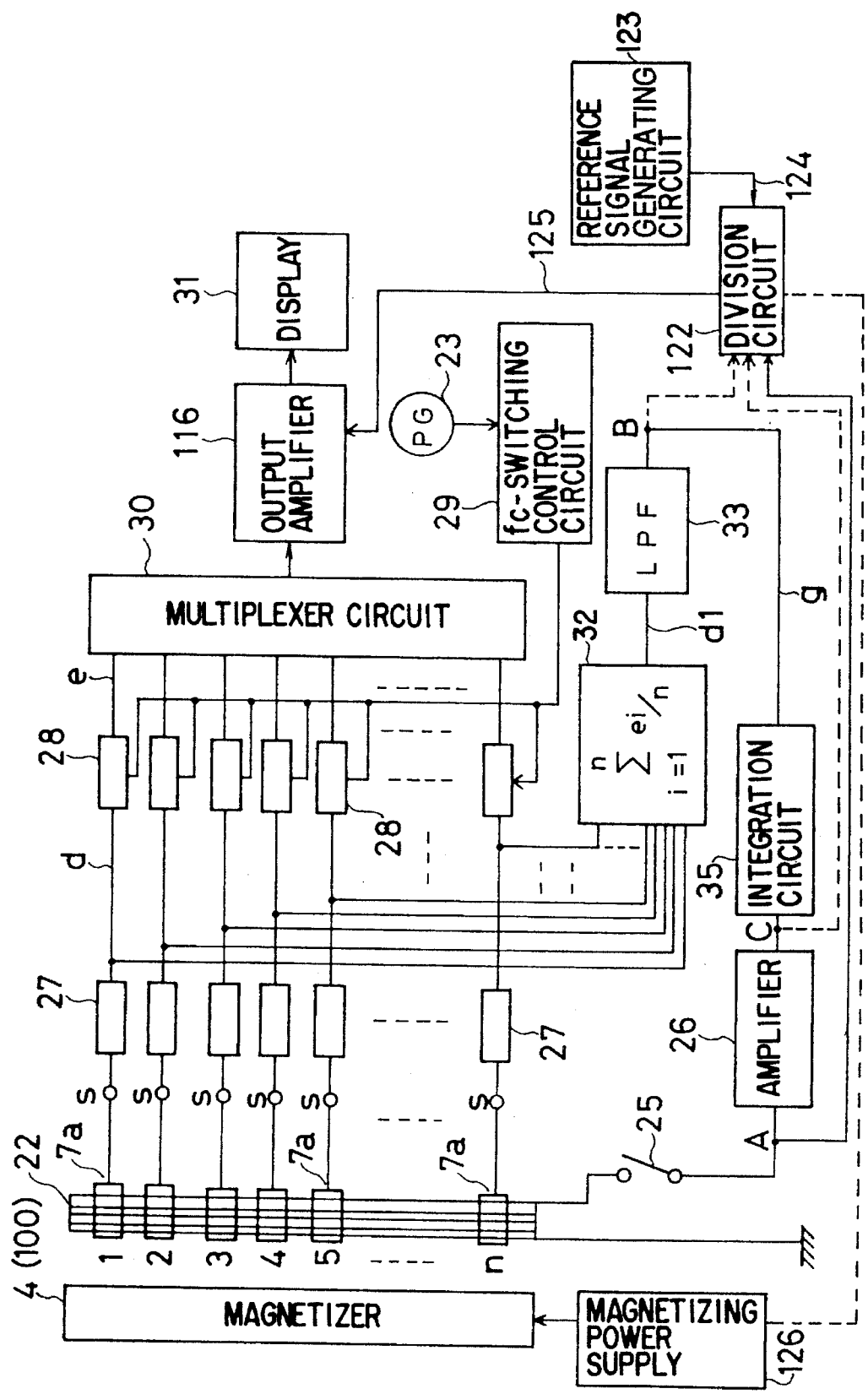
F I G. 32

METHOD AND APPARATUS FOR MAGNETICALLY DETECTING DEFECTS IN AN OBJECT, WITH COMPENSATION FOR MAGNETIC FIELD SHIFT BY MEANS OF A COMPENSATING COIL

BACKGROUND OF THE INVENTION

The present invention relates to a magnetic detecting method and a magnetic detector, in which magnetizers applys magnetic fields crossing over an object made of magnetic material, such as a steel plate, and magnetic sensors are used to detect leakage fluxes generated at magnetically defective portions of the object.

A magnetic detector utilizes magnetism to detect magnetically defective portions of an object, e.g., a thin steel strip, such as flaws or inclusions existing in the surface of the thin steel strip. It is reported that a magnetic detector having a group of magnetic sensors arranged linearly for detecting magnetic fluxes can continuously detect defects existing in a moving thin steel strip, over the entire width thereof. (See Published Unexamined Japanese Utility Model Application 63-107849.)

FIGS. 46A and 46B are sectional views schematically showing the magnetic detector for continuously detecting defects in a moving thin steel strip. FIG. 46C is a side view showing the magnetic detector and also a support device supporting the detector.

As is illustrated in FIG. 46C, a horizontal arm 12 is supported in a frame 11 secured on the floor of a building, by means of a pair of spring members 13a and 13b. The horizontal arm 12 can thereby move up and down. The magnetic detector has a hollow roll 1 and a rigid shaft 2. The rigid shaft 2 is fastened to the center part of the horizontal arm. Two guide rolls 14a and 14b are located at the sides the frame 11, respectively, for guiding a thin steel strip to the outer circumferential surface of the hollow roll 1 of the magnetic detector.

As FIGS. 46A and 46B show, one end of the rigid shaft 2 extends through the hollow roll 1 made of non-magnetic material, located coaxial with the hollow roll 1. The other end of the rigid shaft 2 is fastened to the horizontal arm 12. The rigid shaft 2 is supported and located coaxial with the hollow roll 1, by means of a pair of rolling bearings 3a and 3b. Hence, the hollow roll 1 can freely rotate around the rigid shaft 2.

In the hollow roll 1, a magnetizing core 4c, substantially U-shaped, is fastened to the rigid shaft 2 by a support member 5, having its magnetic poles 4a and 4b positioned near the inner circumferential surface of the hollow roll 1. A magnetizing coil 6 is wound around the magnetizing core 4c. The core 4c and the coil 6 constitute a magnetizer 4. A plurality of magnetic sensors 7a, forming a group 7, are fixed on the rigid shaft 2, located between the magnetic poles 4a and 4b and arranged parallel to the axis of the shaft 2.

A power-supply cable 8 for supplying an exciting current to the magnetizing coil 6, and a signal cable 9 for supplying signals output by the magnetic sensors 7a pass through the rigid shaft 2 and extend outwardly from the shaft 2. Hence, the magnetizer 4 and the group 7 of magnetic sensors are fixed in place, whereas the hollow roll 1 can rotate around the magnetizer 4 and the sensor group 7, slightly spaced apart therefrom.

When the hollow roll 1 of the magnetic detector described above is so moved as to have its outer circumferential surface pushed, with a predetermined pressure, onto one side of a thin steel strip 10 moving in the direction of arrow a, the hollow roll 1 is rotated in the direction of arrow b. This is because the shaft 2 is fastened to the horizontal arm 12.

In the magnetic detector, when an exciting current is supplied to the magnetizing coil 6, the magnetic poles 4a and 4b of the magnetizing core 4c and the thin steel strip 10 form a closed magnetic path. If defects exist in the steel strip 10 or in the surface thereof, the magnetic resistance in the strip 10 changes, generating leakage fluxes. The leakage fluxes are detected by those of the magnetic sensors 7a forming the group 7, which oppose the defective portion of the strip. These magnetic sensors 7a output signals representing the defects.

The levels of the signals detected correspond to the sizes of the defects existing in the thin steel strip 10 or in the surface thereof. The sizes of the defects and the positions they assume widthwise of the strip 10 can be determined by measuring the levels of the output signals.

In this magnetic detector, each magnetic sensor 7a is located at a midpoint between the magnetic poles 4a and 4b. The reason for this specific positioning will be described.

FIG. 47 is a schematic representation of the main section of the magnetic detector shown in FIGS. 46A and 46B. In the detector, the magnetic poles 4a and 4b are arranged, opposing a thin steel strip 10 which has no defects and which is not moving. The magnetizing coil 6 is excited with a DC current. A magnetic field is thereby generated in the vicinity of the magnetic poles 4a and 4b. This magnetic field has a vertical magnetic-field distribution D shaped like a sine wave and a horizontal magnetic-field distribution F shaped like an angle i.e. a curve having substantially symmetrical rising and falling slopes. In the magnetic-field distribution D, the magnetism is maximum and minimum at the poles 4a and 4b, respectively, as is shown in the figure. In the distribution F, the magnetism is maximum at the midpoint between the magnetic poles 4a and 4b. Hence, a magnetic sensor of vertical type, which responds to magnetism applied in the vertical direction, will not be influenced by the magnetic field if the sensor is located at the midpoint between the poles 4a and 4b spaced by distance W, at which the curve of the vertical distribution D crosses the zero-level line.

If a magnetic sensor of horizontal type, which responds to magnetism applied in the horizontal direction, is located at the midpoint between the poles 4a and 4b spaced by distance W, and if the signal output by the horizontal-type magnetic sensor is differentiated, the output signal will have a waveform which is similar to the vertical magnetic-field distribution D in the vicinity of the midpoint between the magnetic poles 4a and 4b. The waveform of the differentiated signal crosses the zero-level line at the midpoint between the poles 4a and 4b. Thus, like the vertical-type magnetic sensor, the horizontal-type magnetic sensor will not be influenced by the magnetic field.

It is, however, desirable that a vertical-type magnetic sensor be used, rather than a horizontal-type one. This is because it can generally be said that a horizontal-type magnetic sensor needs to have a broad dynamic range since, as indicated above, the floating flux at a non-defective portion of a base metal exhibits a great magnitude. To obtain the same output as this, by means of a horizontal-type magnetic sensor, the output of the horizontal-type magnetic sensor must be first processed by a differentiation circuit. Consequently, the detector will be complex. Further, the ratio $(f_S/f_N)_H$ of the frequency $f_S$ of a signal component resulting from a magnetically defective portion to the frequency fN of a noise component achieved by the use of a horizontal-type magnetic sensor is less than the ratio $(f_S/f_N)_V$ achieved by the use of a vertical-type magnetic sensor.

Hence, when a vertical-type magnetic sensor is used, it will be easier to remove noise from the output signal. It is therefore better to use a vertical-type magnetic sensor for the purpose of simplifying the detector for practical use. It is not to say that a magnetic sensor other than a vertical-type one cannot detect a magnetically defective portion.

Even if the magnetic sensors 7a are not located at the midpoint between the magnetic poles 4a and 4b as is shown in FIG. 48, it is possible to eliminate such influence of a magnetic field as has been explained above. Namely, the voltages Vov and Voh which each magnetic sensor 7a so located outputs are determined beforehand from the magnetic-field distributions D and F. Then, as is shown in FIG. 49, a fixed bias voltage output by a bias voltage generator 16 is adjusted to the voltage Vov or Voh, and the voltage Vov (Voh) is subtracted from the output signal of the magnetic sensor 7a by means of a subtracter 15.

Unless otherwise noted, the following description relates to the case where vertical-type magnetic sensors are positioned at the midpoint between the magnetic poles.

The vertical magnetic-field distribution D illustrated in FIG. 47 is the one observed when a flawless thin steel strip 10, not moving, opposes the magnetic poles 4a and 4b. In practical use of the magnetic detector, however, the thin steel strip 10 is moving at speed V in one direction. As the strip 10 moves so, it is magnetized by the magnetic poles 4a and 4b. Because of the speed effect of the strip 10, i.e., an object, moving through the excited magnetic field, the flux distribution is biased in the direction in which the object is moving. More specifically, as the object, which is a conductor, moves through the magnetic field, an eddy current flows in the object, which generates a magnetic field. This magnetic field is assumed to bias the flux distribution in said manner.

As a result, the curve of the vertical magnetic-field distribution crosses the zero-line, not always at the midpoint between the magnetic poles. The vertical magnetic-field distribution shifts in parallel, in the direction in which the object is moving, as is indicated by a vertical magnetic-field distribution E illustrated in FIG. 47.

Thus, while the thin steel strip 10 is moving, the curve representing the vertical magnetic-field distribution E does not cross the zero-level line at the midpoint (X=0) between the magnetic poles 4a and 4b. Therefore, floating fluxes exist at the midpoint.

Floating fluxes are detected around the object, and are distinguished from the leakage fluxes generated due to surface defects, internal defects, and magnetically defective portions such as welded portions. The floating fluxes outwardly emanate from mostly the object, i.e., a bulk, or the magnetizing core of the magnetizer. The floating fluxes, therefore, have a distribution which is similar to each of the magnetic-field distributions illustrated in FIG. 47.

Naturally, the floating fluxes change as the moving speed V of the thin steel strip 10 increases. The floating fluxes change, too, as the exciting current I supplied to the magnetizer 4 is increased. FIG. 50 is a diagram representing how the output voltage of a vertical-type magnetic sensor 7a located at the midpoint (X=0) actually varied as the moving speed V of a flawless thin steel strip 10 was increased from 0 m/min to 1200 m/min. The characteristics shown in FIG. 50 were recorded as the exciting current I for the magnetizing coil 6 was set at 0.25 A, 0.50 A, and 0.75 A. As can be understood from the diagram, the floating fluxes increase as the moving speed V and the exciting current I are increased.

There is a specific range for the intensity of a magnetic flux which the magnetic sensor 7a can detect. When the sensor detects a magnetic flux having an intensity higher than a predetermined value, it outputs a saturated signal. FIG. 51 is a diagram showing the relation between the moving speed V of the flawless thin steel strip 10 and the relative output voltage of the magnetic sensor 7a, which relation is an actually recorded one. As can be understood from this diagram, too, the output signal generated form the floating flux is saturated when the moving speed V of the strip 10 is about 600 m/min if the exciting current I is 0.2 A.

It is often demanded that each magnetic sensor 7a have high sensitivity to leakage fluxes resulting from defects. For example, the sensor is expected to detect so small a flux as about mm gausses. Each magnetic sensor 7a should therefore have its sensitivity enhanced very much.

FIG. 52 is a diagram illustrating how the output voltage of the magnetic sensor 7a actually changed as magnetic fluxes of various intensities were applied, crossing the sensor which has such sensitivity that it outputs 1 V when the intensity of the flux is 1 gauss. As can be understood from this diagram, as the sensitivity of the sensor 7a is increased, its output voltage will be saturated when a flux of about 6 gauss crosses the sensor.

This phenomenon that the output signal of the magnetic sensor 7a is saturated becomes more prominent when the moving speed V of the thin steel strip 10 increases. FIG. 53 is a diagram representing the relation which the output of the sensor 7a and the exciting current I had when a steel strip 10 having an artificial defect having a diameter of 0.6 mm was put to defect detection.

As this diagram reveals, the output of the magnetic sensor 7a will decrease, rather than be saturated only, when the exciting current I is increased over a certain value, as the moving speed V of the steel strip 10 and the exciting current I for the magnetizer 4 are increased in order to enhance the defect-detecting sensitivity.

Hence, even if the sensitivity of the magnetic sensor 7a is increased, the sensor is still unable to detect a small defect. Further, since the floating flux emanating from a flawless steel strip is far more intense than the leakage flux generated at a small defect existing in a steel strip, the output signal will be saturated due to the floating flux when the detection sensitivity of the magnetic sensor 7a is increased. As a consequence, it is impossible to detect a small defect with high accuracy.

The problem is not a phenomenon specific to only a magnetic detector of the type which has a hollow roll as is disclosed in Published Unexamined Japanese Utility Model Application 63-107849. In particular, a decrease in the defect-detecting accuracy, resulting from a leakage flux, is the phenomenon which is generally observed in so-called magnetic detection technology of detecting magnetically defective portions by means of a magnetizer.

The thin steel strip 10, i.e., the object of magnetic detection, has its magnetizing characteristic changed with the speed V at which it is moved. The higher the moving speed V of the strip 10, the less liable the steel strip 10 is magnetized, because of the speed effect described above. Consequently, any defect of a specific size will be detected to have a different size if the moving speed V of the thin steel strip 10 changes.

SUMMARY OF THE INVENTION

The first object of the present invention is to provide a magnetic detecting method and a magnetic detector, which can remove a low-frequency component generated from a floating flux and contained in an output signal of a magnetic sensor which detects a leakage flux generated at a magnetically defective portion of an object, can increase the S/N ratio of the output signal of the magnetic sensor, and can detect the magnetically defective portion with greatly improved sensitivity and accuracy.

The second object of the invention is to provide a magnetic detector which not only achieves the object described above, but also can maintain a predetermined detection sensitivity even if the moving speed of the object changes.

To attain the first object, in a magnetic detecting method and a magnetic detector, according to the invention, a low-pass filter extracts a low-frequency component from the output signal of the magnetic sensor which detects the leakage flux generated at a magnetically defective portion of an object which is moving in a magnetic field. The low-frequency component, thus extracted, is amplified and applied to a compensating coil. The magnetic flux generated by the compensating coil cancels out the floating flux crossing the magnetic sensor.

Generally, the floating flux generated also at a non-defective portion of an object moving in a magnetic field changes with time at a frequency much lower than the frequency at which a leakage flux generated at a magnetically defective portion of the object changes. Hence, the floating flux component can be extracted from the output signal of the magnetic sensor by means of a low-pass filter. If this low-frequency component is applied, in reverse polarity, for example, to a compensating coil, the compensating coil will generate a magnetic flux which extends in such a direction as to cancel out the floating flux. As a result of this, the component generated from the floating flux will be removed from the output signal of the magnetic sensor.

To attain the second object, in a magnetic detector according to the invention, a signal-extracting filter comprising, for example, a high-pass filter or a low-pass filter extracts a signal generated at a magnetically defective portion of an object from an output signal of the magnetic sensor which detects the leakage flux generated at the magnetically defective portion. An output amplifier amplifies the output signal of the signal-extracting filter and outputs a defect signal. Another magnetic sensor is located in the vicinity of the sensor for detecting the leakage flux, and detects a magnetic flux extending in parallel to the surface of the object. The output signal of this magnetic sensor controls the amplification factor of the output amplifier.

The magnetic field generated at an object opposing a magnetizer has a vertical magnetic-field distribution D which is represented by a sine wave as is illustrated in FIG. 47. By contrast, the horizontal magnetic-field distribution F of this magnetic field is shaped like an angle. A horizontal-type magnetic sensor which detects a component extending in parallel to the surface of an object is used to measure the intensity of a magnetic field existing in or passing through the object. The intensity of this magnetic field varies with the moving speed of the object, as has been explained. In addition, the horizontal component of the magnetic field has its intensity changed with the magnetization characteristics of the object, which is determined by the thickness or other physical property (e.g., the carbon content in the case of a steel strip).

Hence, the output amplifier can output a defect signal having a speed-compensated correct level, only if a horizontal-type magnetic sensor detects the change in intensity of the magnetic field, which has been caused by the variation of the moving speed, and the amplification factor of the output amplifier is controlled by the change in the magnetic-field intensity change thus detected.

BRIEF DESCRIPTION OF THE DRAWINGS

FIG. 6A is a sectional view of a vertical-type magnetic sensor and a compensating coil, both incorporated in the magnetic detector according to an embodiment;

FIG. 6B is a sectional view of a horizontal-type magnetic sensor and a compensating coil, both incorporated in the magnetic detector according to an embodiment;

FIG. 6C is a sectional view illustrating the positional relation which the vertical-type magnetic sensor and compensating coil incorporated in the magnetic detector shown in FIG. 2A assume with respect to a thin steel strip;

FIG. 31 is a block diagram showing a magnetic detector according to a further embodiment of this invention;

FIG. 32 is a block diagram showing a magnetic detector according to another embodiment of the present invention;

DETAILED DESCRIPTION OF THE PREFERRED EMBODIMENTS

Embodiments of the present invention will be described as follows, with reference to the drawings.

Figure 1:
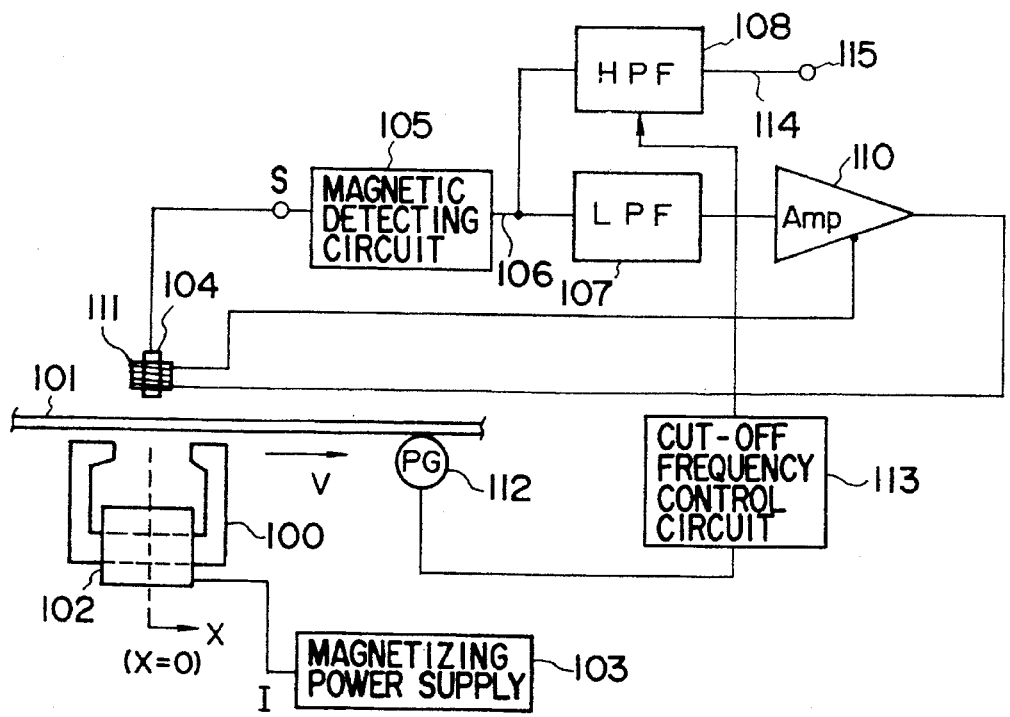
FIG. 1 is a block diagram showing a magnetic detector according to an embodiment of the invention, to which a magnetic detecting method according to the invention is applied.

FIG. 1 is a block diagram showing a magnetic detector according to an embodiment of the invention, to which a magnetic detecting method according to the invention is applied.

A magnetizer 100 is located such that a pair or magnetic poles oppose a thin steel strip 101 which is an object. The magnetizer 100 generates magnetic fluxes crossing the thin steel strip 101. A magnetizing power supply 103 supplies an exciting current I to the exciting coil 102 of the magnetizer 100. A vertical-type magnetic sensor 104 is located above the thin steel strip 101 and at the midpoint between the magnetic poles of the magnetizer 100, for detecting the leakage fluxes generated at magnetically defective portions existing in the thin steel strip 101 or in the surface thereof. A magnetic detecting circuit 105 converts a signal output by the magnetic sensor 104 into an output signal 106 which corresponds to the intensity of the magnetic fluxes crossing the magnetic sensor 104. The output signal 106 is input to a low-pass filter 107 and a high-pass filter 108 which serves as a signal-extracting filter.

The low-pass filter 107 extracts the low-frequency component contained in the output signal 106. The low-frequency signal component, extracted by the low-pass filter 107, is supplied to an amplifier 110. The amplifier 110 amplifies the low-frequency signal component and supplies it to a compensating coil 111 would around the outer circumferential surface of the magnetic sensor 104.

Meanwhile, a speed detector 112 detects the speed V at which the thin steel strip 101 is moving. The signal output by the detector 112 and representing the speed V is input to a cut-off frequency control circuit 113. The control circuit 113 changes the cut-off frequency of the high-pass filter 108 in accordance with the input signal representing the speed V. The high-pass filter 108 extracts the high-frequency component contained in the output signal 106 of the magnetic detecting circuit 105 and outputs the high-frequency component in the form of a defect signal 114.

A band-pass filter whose pass-frequency band is broad can be used in place of the high-pass filter 108. If a band-pass filter is so used, the center frequency of its pass-frequency band is varied with the moving speed V of the thin steel strip 101, under the control of the cut-off frequency control circuit 113. In view of this, the band-pass filter performs a function almost the same as that of the high-pass filter 108.

In the magnetic detector thus structured, if the thin steel strip 101, which has no magnetically defective portions at all, moves in the direction of the arrow shown in FIG. 1, the intensity of the magnetic flux at the position of the vertical-type magnetic sensor 104 (X=0) is not zero. Rather, it has the value of a floating flux corresponding to the moving speed V, as is seen from the magnetic-field distribution E shown in FIG. 47. Therefore, the signal 106 output by the magnetic sensor 104 is a low-frequency signal which has resulted from the floating flux which is at almost constant level corresponding to the moving speed V. If the moving steel strip 101 has a magnetically defective portion such as a portion having a defect, the magnetic sensor 104 detects a leakage flux resulting from this magnetically defective portion. The high-frequency component generated due to the magnetically defective portion is superposed on the low-frequency component which corresponds to the floating flux.

The low-pass filter 107 extracts the low-frequency signal component. The low-frequency signal component is amplified by the amplifier 110 to a predetermined level and is then supplied to the compensating coil 111. When excited, the compensating coil 111 generates magnetic fluxes having such a polarity that they cancel the floating flux. As a result, the magnetic fluxes synthesized and crossing the magnetic sensor 104 are gradually canceled to have their intensity reduced toward zero. Thus, the low-frequency signal component contained in the output signal 106 of the sensor 104 is attenuated.

The compensating coil 111, the magnetic sensor 104, the low-pass filter 107, and the amplifier 110 constitute a kind of a negative feedback loop. The negative feedback loop operates to cancel the low-frequency component contained in the output signal 106 even if the moving speed V of the thin steel strip 101 varies, inevitably changing the level of the low-frequency signal component. The defect signal contained in the output signal 106 and generated due to the magnetically defective portion has a frequency much higher than that of the low-frequency signal component. Hence, the defect signal is removed by the low-pass filter and negatively fed back to the closed feedback loop.

Since the defect signal 114 is extracted from the output signal 106 of the magnetic sensor 104 by means of the high-pass filter 108, the influence of the floating flux contained in the defect signal 114 can be removed completely. When the moving speed V of the thin steel strip 101 changes, the component contained in the output signal 106 of the magnetic sensor 104 and corresponding to the defect signal has its frequency changed to the high-band side. Therefore, the cut-off frequency control circuit 113 controls the cut-off frequency fc of the high-pass filter 108 in accordance with the moving speed V. The size of the magnetically defective portion, such as a portion having a defect, can thereby be detected with improved accuracy.

Thus, it is possible to efficiently extract only the defect signal generated due to the magnetically defective portion, from the signal 106 output by the magnetic sensor 104.

Figure 2A:
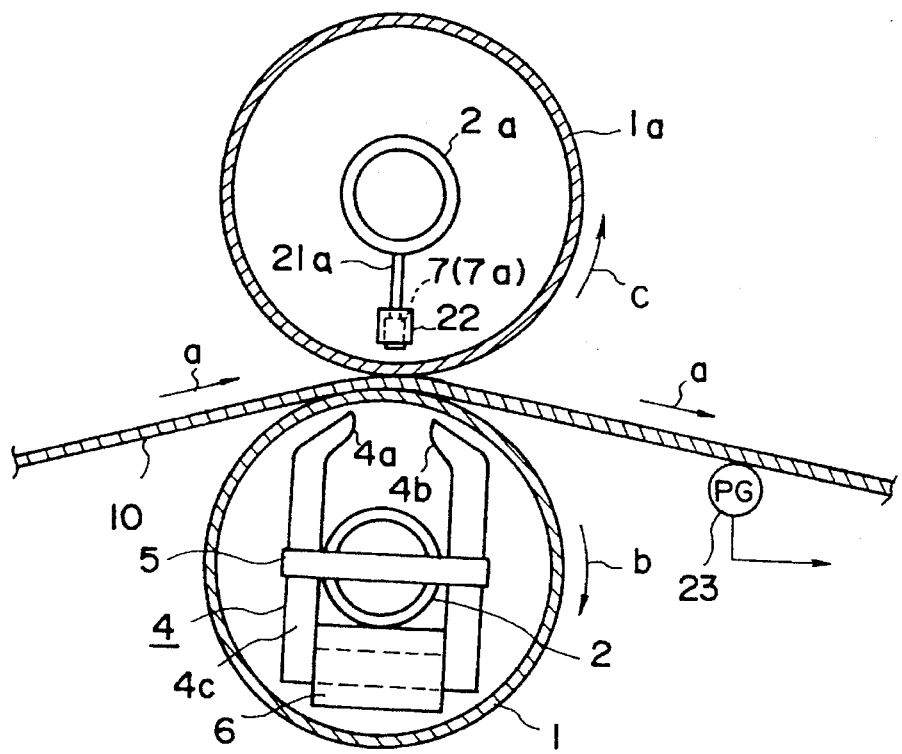
FIG. 2A is a sectional view showing the magnetic detector shown in FIG. 1 in greater detail, taken along a plane extending parallel to the direction in which a thin steel strip is moving.
Figure 2B:
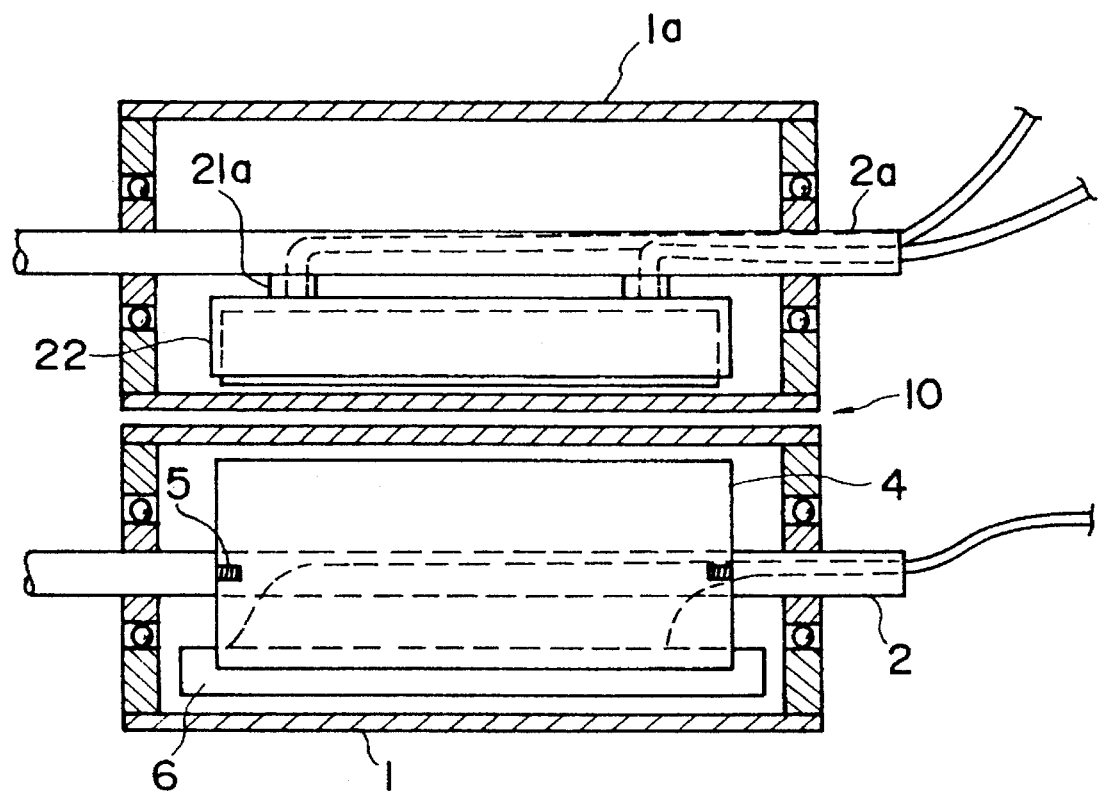
FIG. 2B is a sectional view of the detector, taken along a plane extending at right angles to the direction in which the thin steel strip is moving.
Figure 2C:
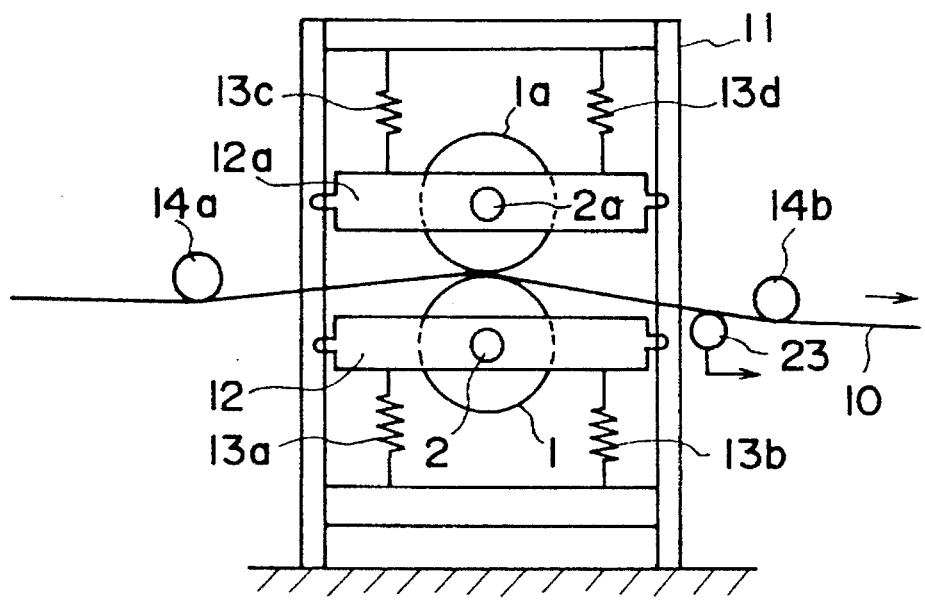
FIG. 2C is a side view of the detector and a support device in which the detector is incorporated.
Figure 46A:
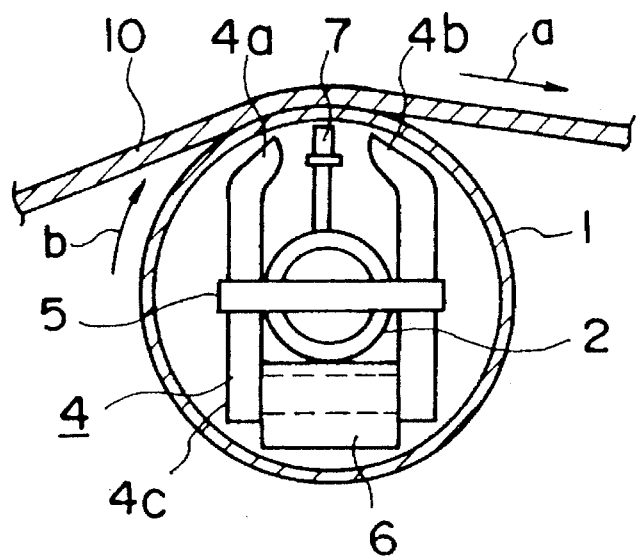
FIG. 46A is a sectional view of a conventional magnetic detector, taken along a plane extending parallel to the direction in which a thin steel strip is moving.
Figure 46B:
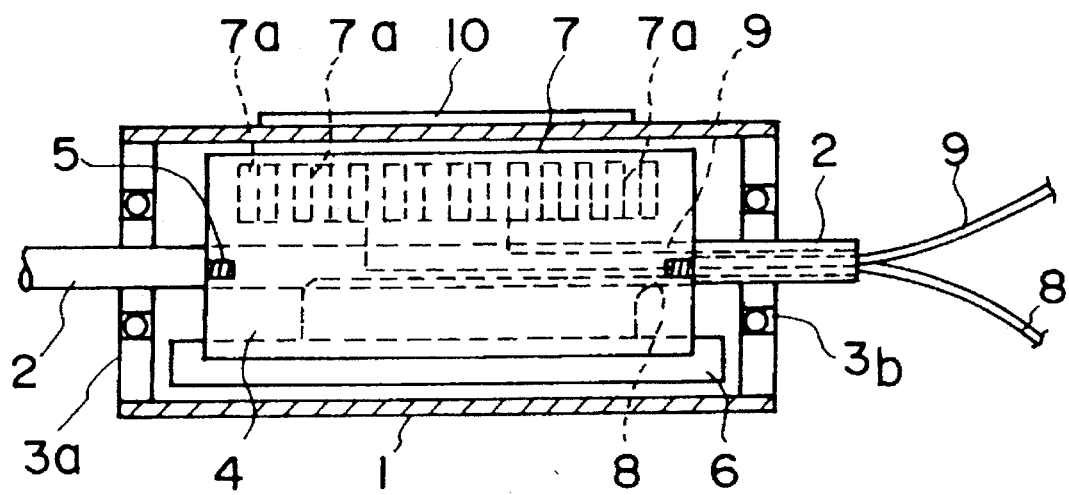
FIG. 46B is a sectional view of the conventional magnetic detector, taken along a plane extending at right angles to the direction in which a thin steel strip is moving.
Figure 46C:
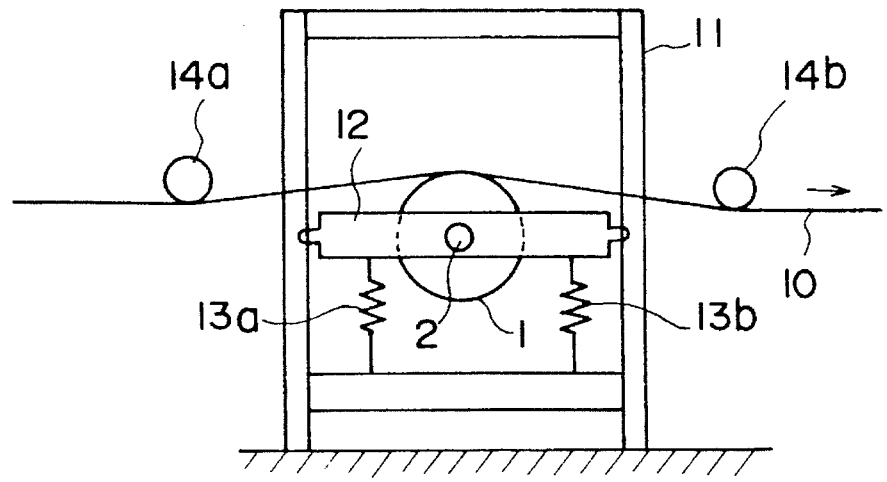
FIG. 46C is a side view of a support device and the conventional magnetic detector incorporated in the support device.

FIGS. 2A, 2B, and 2C are sectional views showing the magnetic detector of FIG. 1, incorporated in an inspection line installed in a factory. The components identical to those of the magnetic detector shown in FIGS. 46A, 46B, and 46C are denoted by the same reference numerals and will not, therefore, be described in detail.

In this embodiment, hollow rolls 1 and 1a are arranged, with a thin steel strip 10, i.e., an object, pinched between them. As is shown in FIG. 2C, two horizontal arms 12 and 12a are supported within a frame 11 by means of spring members 13a, 13b, 13c, and 13d. The horizontal arms 12 and 12a can thereby move up and down. Rigid shafts 2 and 2a are fastened to the center portions of the horizontal arms 12a and 12a, respectively. A pair of guide rolls 14a an 14b are arranged at the sides of the frame 11, respectively, for guiding the thin steel strip 10 into the gap between the hollow rolls 1 and 1a.

As FIGS. 2A and 2B show, an end portion of the rigid shaft 2 extends through the lower hollow roll 1 made of non-magnetic material, along the axis thereof. The rigid shaft 2 is rotatably supported by a pair of rolling bearings, such that it remains coaxial with the hollow roll 1. The hollow roll 1 therefore can freely rotate around the axis of the rigid shaft 2.

In the hollow roll 1, a magnetizing core 4c is secured to the rigid shaft 2 by a support member 5, with its magnetic poles 4a and 4b located near the inner circumferential surface of the hollow roll 1. The magnetizing coil 6 of a magnetizer 4 is wound around the magnetizing core 4c.

The hollow roll 1a, which is located above the hollow roll 1 and pinching the steel strip 10, together with the hollow roll 1, is arranged such that it can rotate around the rigid shaft 2a. It is rotated in the direction of arrow c when the thin steel strip 10 moves in the direction of arrow a. A group 7 of magnetic sensors is secured by support rods 21a to the rigid shaft 2a extending through the hollow roll 1a, such that the magnetic sensors oppose the poles 4a and 4b of the magnetizer 4 contained in the lower hollow roll 1. The group 7 consists of a plurality of magnetic sensors 7a arranged linearly. The signal cable of each magnetic sensor 7a is led through the rigid shaft 2a to the outside.

A compensating coil 22 is wound around the group 7 of magnetic sensors. A support rod 21a of FIG. 2A has an end thereof attached to the coil 22. The support rod 21a is attached at another end thereof to a rigid shaft 2a. A signal line for supplying an exciting current to the compensating coil 22 is supplied through the rigid shaft 2a, as well. A speed detector 23 comprising, for example, a tachometer, is located at the path of the thin steel strip 10, for detecting the speed V at which the strip is moving.

Figure 3A:
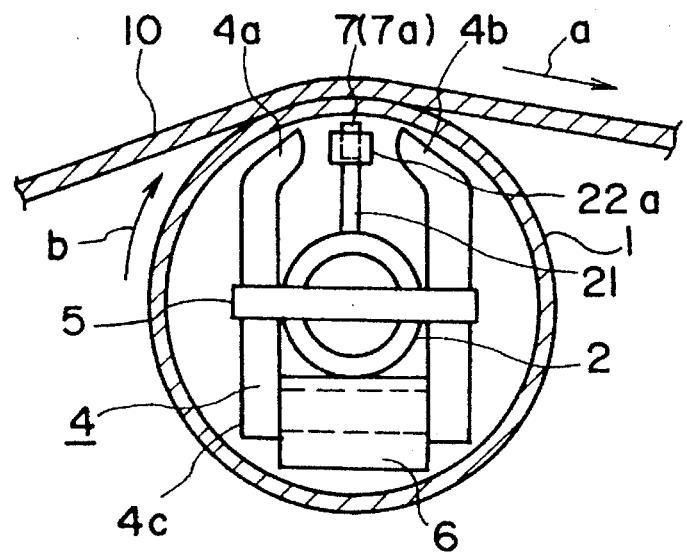
FIG. 3A is a sectional view of a magnetic detector according to another embodiment of the invention, taken along a plane extending parallel to the direction in which a thin steel strip is moving.
Figure 3B:
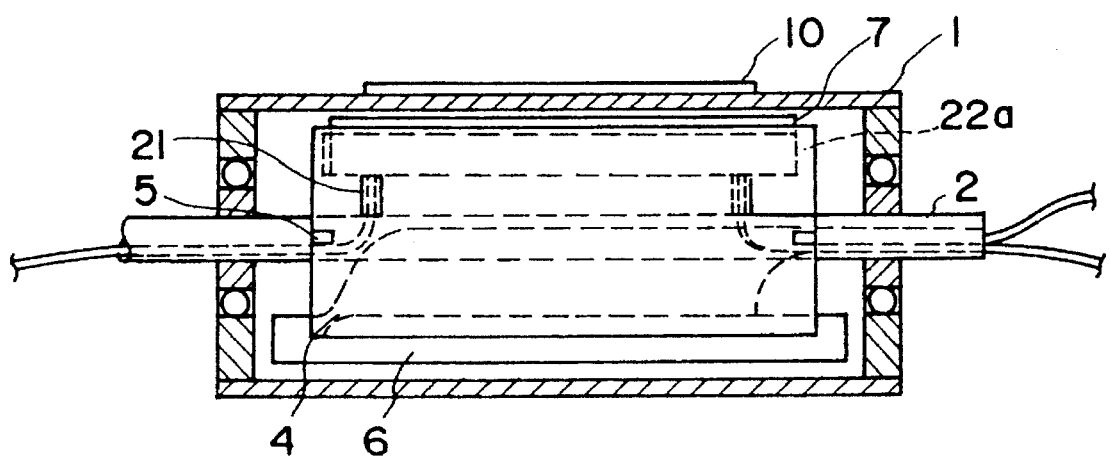
FIG. 3B is a sectional view of the detector, taken along a plane extending at right angles to the direction in which the thin steel strip is moving.

FIGS. 3A and 3B are sectional views showing a magnetic detector according to another embodiment of the present invention. This detector has only one hollow roll 1. As is shown in FIGS. 3A and 3B, each magnetic sensor 7a and a compensating coil 22 are located at the midpoint between the poles 4a and 4b of a magnetizer 4 which is placed within a lower hollow roll 1. Having only one hollow roll 1, this detector can be small as a whole.

Figure 4A:
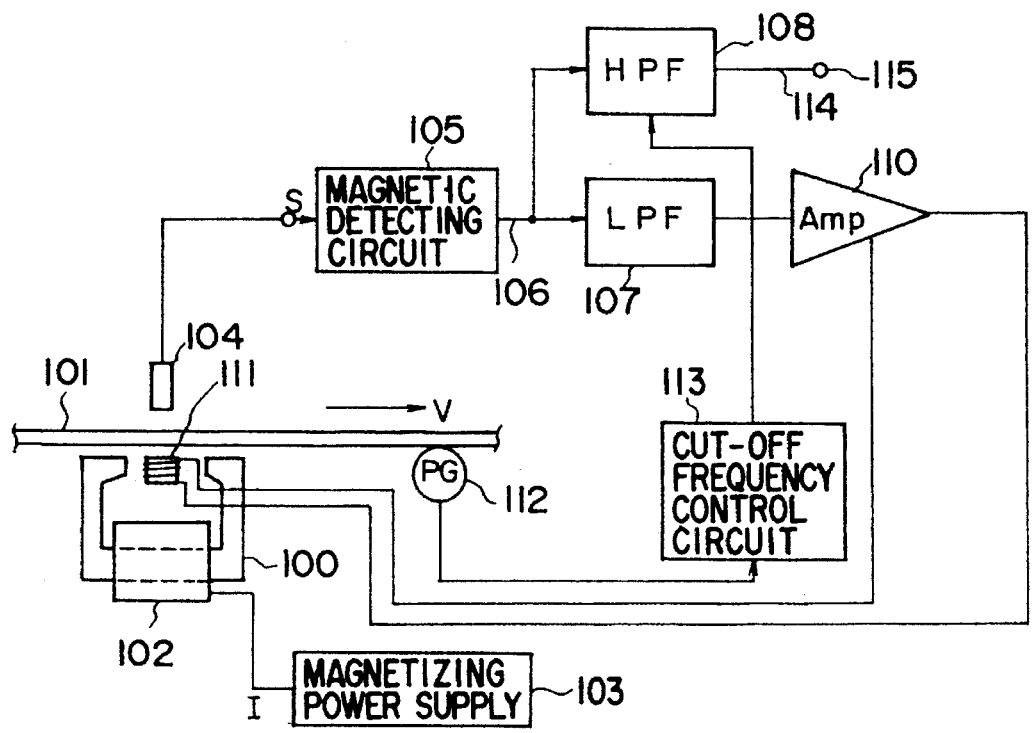
FIG. 4A is a block diagram showing a magnetic detector according to still another embodiment of the invention.

FIG. 4A is a block diagram illustrating a magnetic detector according to still another embodiment of the invention. The components identical to those of the embodiment shown in FIG. 1 are designated by the same reference numerals and will not be described in detail.

In this detector, only magnetic sensors 104 are located above a thin steel strip 101. A compensating coil 111 is positioned between the poles of a magnetizer 100 which is located beneath the thin steel strip 101. The detector is identical to the embodiment FIG. 1 in all other respects.

Figure 4B:
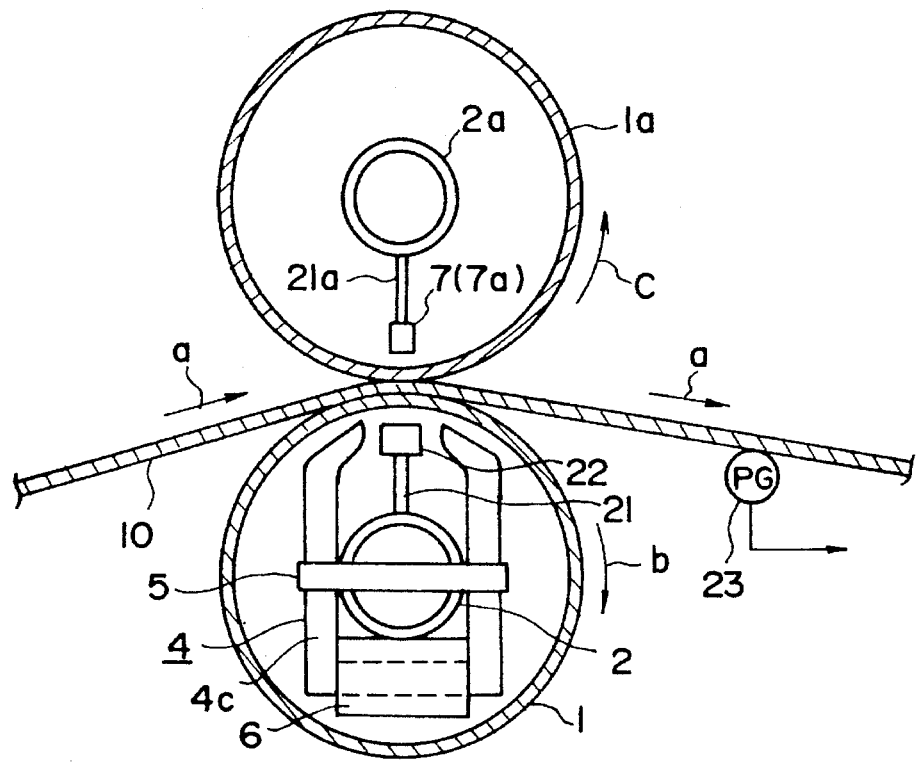
FIG. 4B is a sectional view of the detector, taken along a plane extending parallel to the direction in which a thin steel strip is moving.
Figure 4C:
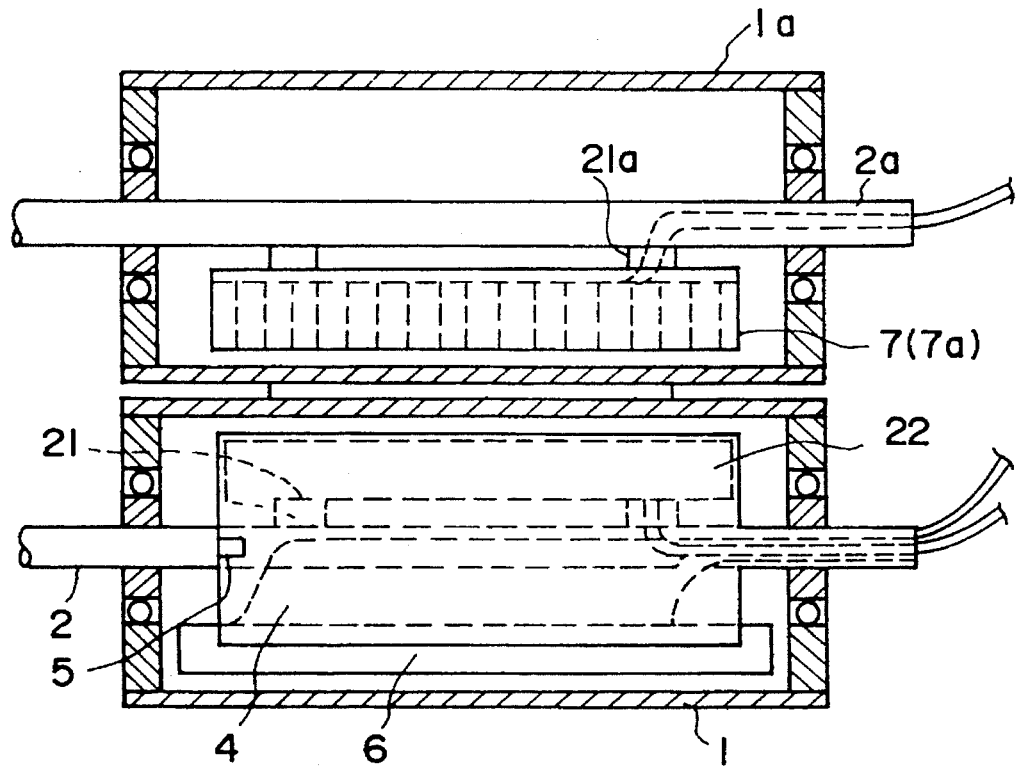
FIG. 4C is a sectional view of the detector, taken along a plane extending at right angles to the direction in which the thin steel strip is moving.

FIGS. 4B and 4C are sectional views showing the detector of FIG. 4A which is incorporated in an inspection line installed in a factory. In this embodiment, each magnetic sensor 7a is attached to a support rod 21a fastened to the rigid shaft 2a held in an upper hollow roll 1a. A compensating coil 22 is arranged at the midpoint between the magnetic poles 4a and 4b of a magnetizer 4 contained in a lower hollow roll 1. The compensating coil 22 is secured by a support rod 21 to a rigid shaft 2.

Figure 5A:
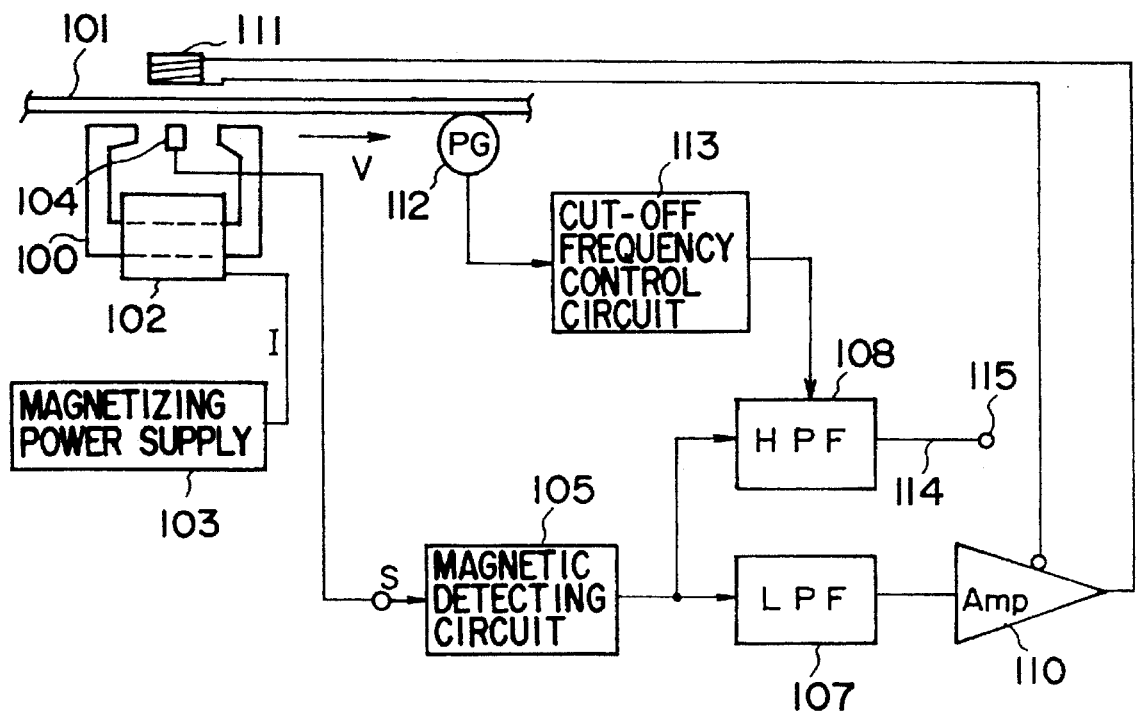
FIG. 5A is a block diagram illustrating a magnetic detector according to another embodiment of the invention.

FIG. 5A is a block diagram showing a magnetic detector according to a different embodiment of the invention. The components identical to those of the embodiment shown in FIG. 1 are denoted by the same reference numerals and will not be described in detail. In this embodiment, only a compensating coil 111 is located above a thin steel strip 101, unlike in the detector shown in FIG. 4A. Magnetic sensors 7a are located below the steel strip 101, at the midpoint between the magnetic poles of a magnetizer 100. Except for these points, the embodiment is identical in structure to the detector shown FIG. 1.

Figure 5B:
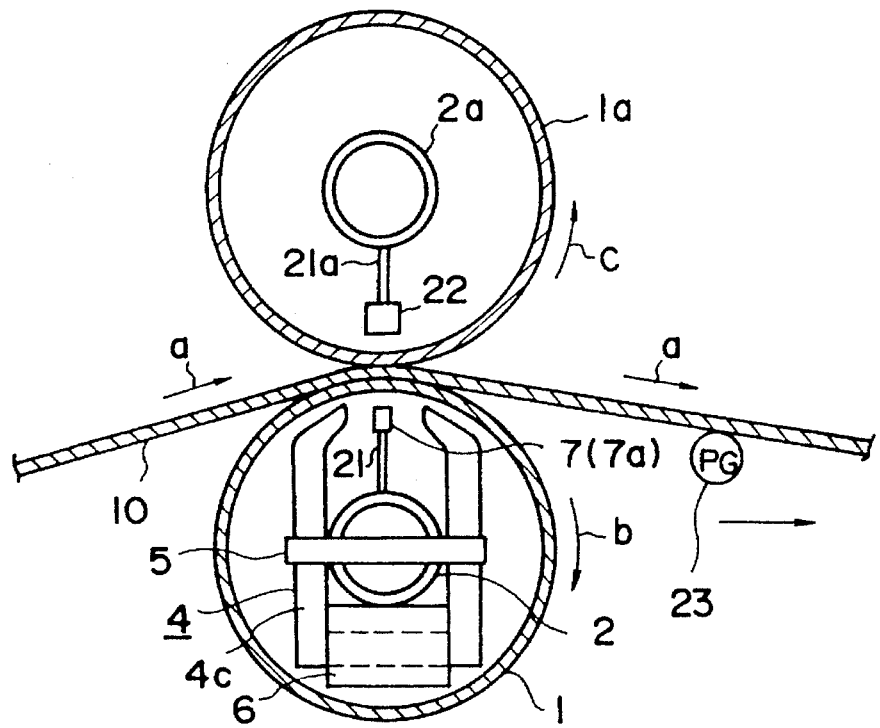
FIG. 5B is a sectional view of the detector, taken along a plane extending parallel to the direction in which a thin steel strip is moving.
Figure 5C:
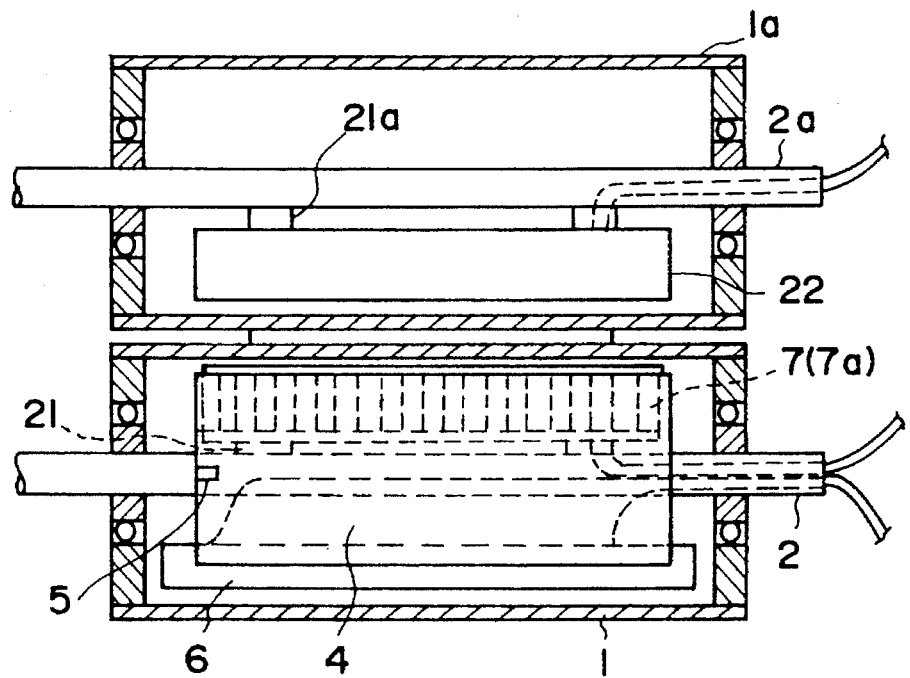
FIG. 5C is a sectional view of the detector, taken along a plane extending at right angles to the direction in which the thin steel strip is moving.

FIGS. 5B and 5C are sectional views showing the detector of FIG. 5A which is incorporated in an inspection line installed in a factory. In the embodiment, the compensating coil 22 is attached to a support rod 21a which is secured to a rigid shaft 2a extending through an upper hollow roll 1a. Each of the magnetic sensors 7a is located at the midpoint between the poles 4a and 4b of the magnetizer 4 which extends through a lower hollow roll 1. Each magnetic sensor 7a is fastened by a support rod 21 to the rigid shaft 2.

Each of the magnetic sensors and the compensating coil, both used in each of the embodiments shown in FIGS. 1 to 5C, will now be described in detail, with reference to FIGS. 6A and 6B.

Shown in FIG. 6A is a vertical-type magnetic sensor 7a for detecting magnetic fluxes extending at right angles to the steel strip 10. Shown in FIG. 6B is a horizontal-type magnetic sensor 7b for detecting magnetic fluxes extending parallel to the steel strip 10. The magnetic sensors 7a and 7b are identical in structure, but different only in the positions they take. Each of the magnetic sensors 7a, forming the group 7, is a saturable magnetic sensor comprising a rod-shaped core made of ferromagnetic material and a detection coil wound around the core. So is each of the magnetic sensors 7b forming the group 7.

A saturable magnetic sensor, which has the high detection sensitivity described above, is the most desirable for the magnetic sensors 7a and 7b. Nevertheless, other known magnetic sensing elements such as an MR element, a Hall element, and a magnetic diode, can be used.

The group 7 of many magnetic sensors 7a or 7b linearly arranged is surrounded by the compensation coil 22 which is wound around the outer circumferential surface of a shield cylinder 24 made of ferromagnetic material such as permalloy.

In the case where the vertical-type magnetic sensors 7a shown in FIG. 6A are used, the compensating coil 22 has a height H greater than the length L of each magnetic sensor 7a (H>L), thus covering the entire group 7 of magnetic sensors. The shield cylinder 24 is used to improve the directivity of the magnetic sensors 7a so that the sensors 7a may efficiently detect only the magnetic fluxes existing below them.

In the case where the horizontal-type magnetic sensors 7b shown in FIG. 6b are used, the compensating coil 22 does not have the above-mentioned dimensional limitations (H>L) which it has with respect to the vertical-type magnetic sensors 7a. It suffices that the compensating coil 22 be large enough to surround the horizontal-type magnetic sensors 7b.

The compensating coil 22 may be wound around the outer circumferential surface of the group 7 of magnetic sensors, with an insulator interposed between the coil and the group. Further, a molded member may be arranged around the group 7 of magnetic sensors, and the compensating coil 22 may be wrapped around the outer circumferential surface of the molded member.

If a magnetic sensor comprises a group 7 consisting of a number of magnetic sensors 7a, as in the embodiments described above, it is desirable that the group 7 of magnetic sensors 7a be surrounded by one compensating coil 22. Nevertheless, a plurality of compensating coils may be used, each surrounding one of the magnetic sensors 7a. Needless to say, if the group of magnetic sensors comprises only one magnetic sensor, it suffices that one compensating coil be used, surrounding the magnetic sensor.

FIG. 6C is an enlarged view showing a main section of the embodiment shown in FIG. 2A, incorporating the vertical-type magnetic sensor 7a and the compensating coil 22, both illustrated in FIG. 6A. Each of the magnetic sensors 7a forming the group 7 are located at the midpoint (H=0) of a line parallel to the line connecting the magnetic poles 4a and 4b, and extends at right angles to the thin steel strip 10. Hence, each magnetic sensor 7a detects the vertical components of the magnetic flux resulting from a defect, which extend at right angles to the surface of the thin steel strip 10.

Figure 7:
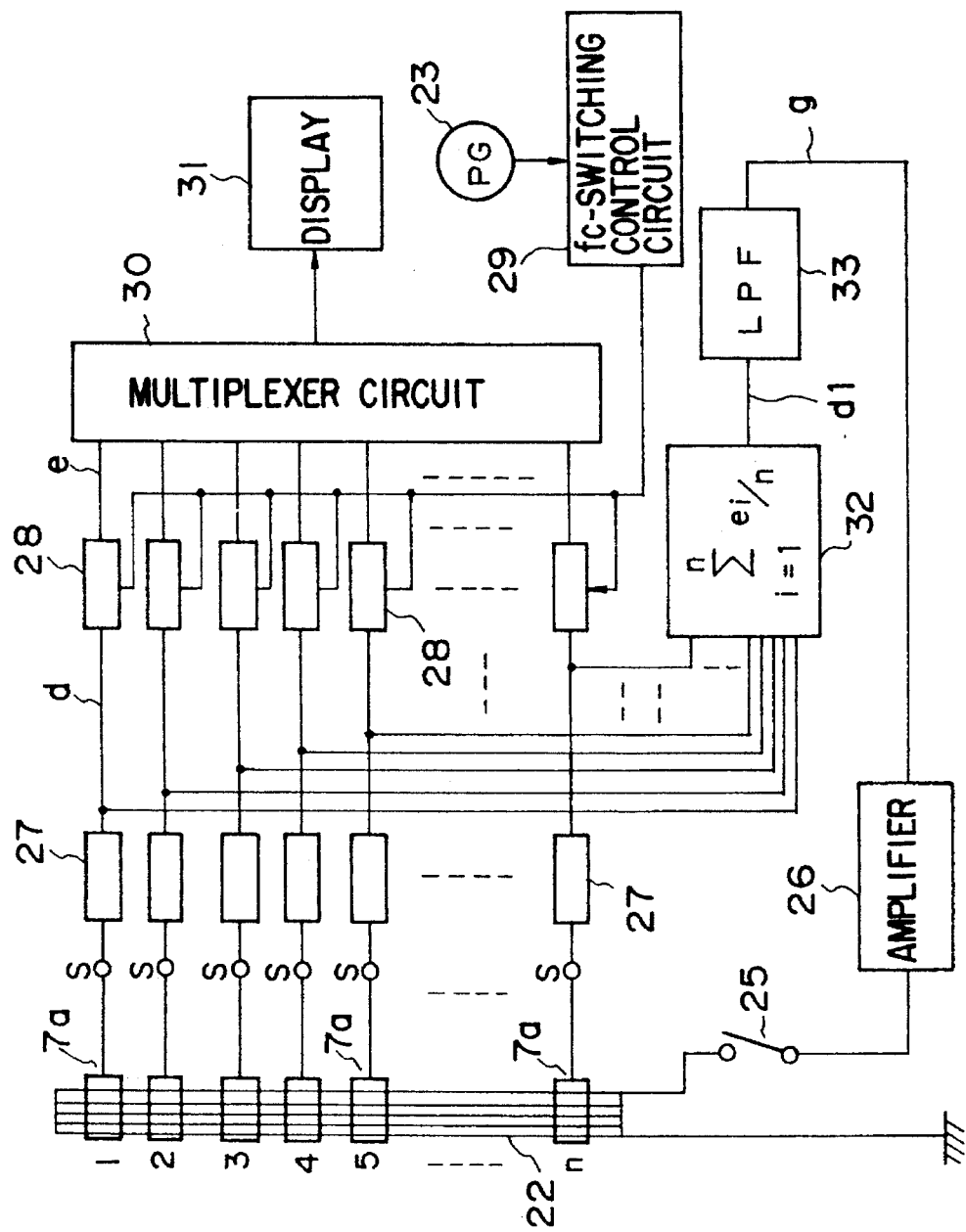
FIG. 7 is a block diagram showing the electrical structure of the magnetic detector shown in FIG. 2A.

FIG. 7 is a block diagram showing the identical electrical structures of the magnetic detectors shown in FIGS. 2A to 2C and FIGS. 3A and 3B, illustrating all components but the magnetizer 4 contained in the lower hollow roll 1.

As is shown in the figure, n magnetic sensors 7a are arranged in the widthwise direction of the thin steel strip 10. The compensating coil 22 is wound around and surrounds the group 7 consisting of n magnetic sensors 7a. One end of the compensating circuit 22 is grounded, and the other end thereof is connected by a switch 25 to the output terminal of an amplifier 26.

The magnetic sensors 7a are connected to magnetic detecting circuits 27, each to one detecting circuit 27. Each magnetic detecting circuit 27 outputs a signal d which is proportional to the magnetic fluxes crossing the magnetic sensor 7a. The n signals d output from the magnetic detecting circuits 27 are input to high-pass filters 28, each to one high-pass filter. Each high-pass filter 28 has a plurality of cut-off frequencies ranging from 20 Hz to 3 kHz, for example. One of the cut-off frequencies fc is selected in accordance with a switching signal supplied from a cut-off frequency switching control circuit 29. As has been indicated, band-pass filters, whose pass-frequency band is broad, can be used in place of the high-pass filters 28.

The moving speed V output by the speed detector 23 is input to the cut-off frequency switching control circuit 29. The circuit 29 outputs a switching control signal corresponding to the moving speed V input. As a result, the cut-off frequency fc of each high-pass filter 28 increases as the moving speed V increases. Hence, each high-pass filter 28 extracts from the output signal d a defect signal e corresponding to leakage flux resulting from a defect, with the cut-off frequency fc which corresponds to the moving speed V.

The defect signal e extracted by each high-pass filter 28 is input to a multiplexer circuit 30. The multiplexer circuit 30 sequentially selects defect signals e at regular intervals, which are displayed by a display 31 such as a CRT display.

The n signals output from the magnetic detecting circuits 27 are input to an equalizing circuit 32. The equalizing circuit 32 equalizes the n output signals d and outputs an equalized signal d1. The equalized signal d1 output from the equalizing circuit 32 is input to a low-pass filter 33. The cut-off frequency fc of the low-pass filter 33 is very low, for example, 1 Hz. From the output terminal of the low-pass filter 33 there is output a low-frequency component g corresponding to the intensity of a floating flux generated when a portion of the base metal, which is flawless in terms of properties and thickness, or the magnetic sensor 7a is displaced (for example, in the direction of arrow X), or when the thin steel strip 10 is moved.

The low-frequency component extracted by the low-pass filter 33 is input to an amplifier 26. The amplifier 26 amplifies the low-frequency component g with a prescribed amplification factor and applies it to the compensating coil 22 through the switch 25.

The polarity of the current to supply to the compensating coil 22 is set such that the coil will generate a magnetic field having the polarity which is opposite to the that of the magnetic field formed of the floating flux. Therefore, when an exciting current is supplied from the amplifier 26 to the compensating coil 22, there will be generated a magnetic flux which extends to cancel out the floating flux. As a result, the vertical magnetic flux is canceled and reduced greatly.

A terminal S is provided on the signal path extending from each magnetic sensor 7a to the magnetic detecting circuit 27 to which the sensor 7a is connected. If necessary, a fixed bias circuit shown in FIG. 49 and comprised of a subtracter 15 and a bias voltage generator 16 is connected to the terminal S. More specifically, if each magnetic sensor 7a is displaced from the midpoint (X=0) between the magnetic poles 4a and 4b of the magnetizer 4, a fixed bias voltage Vov is applied (subtraction), thereby to compensate the displacement electrically.

Figure 8:
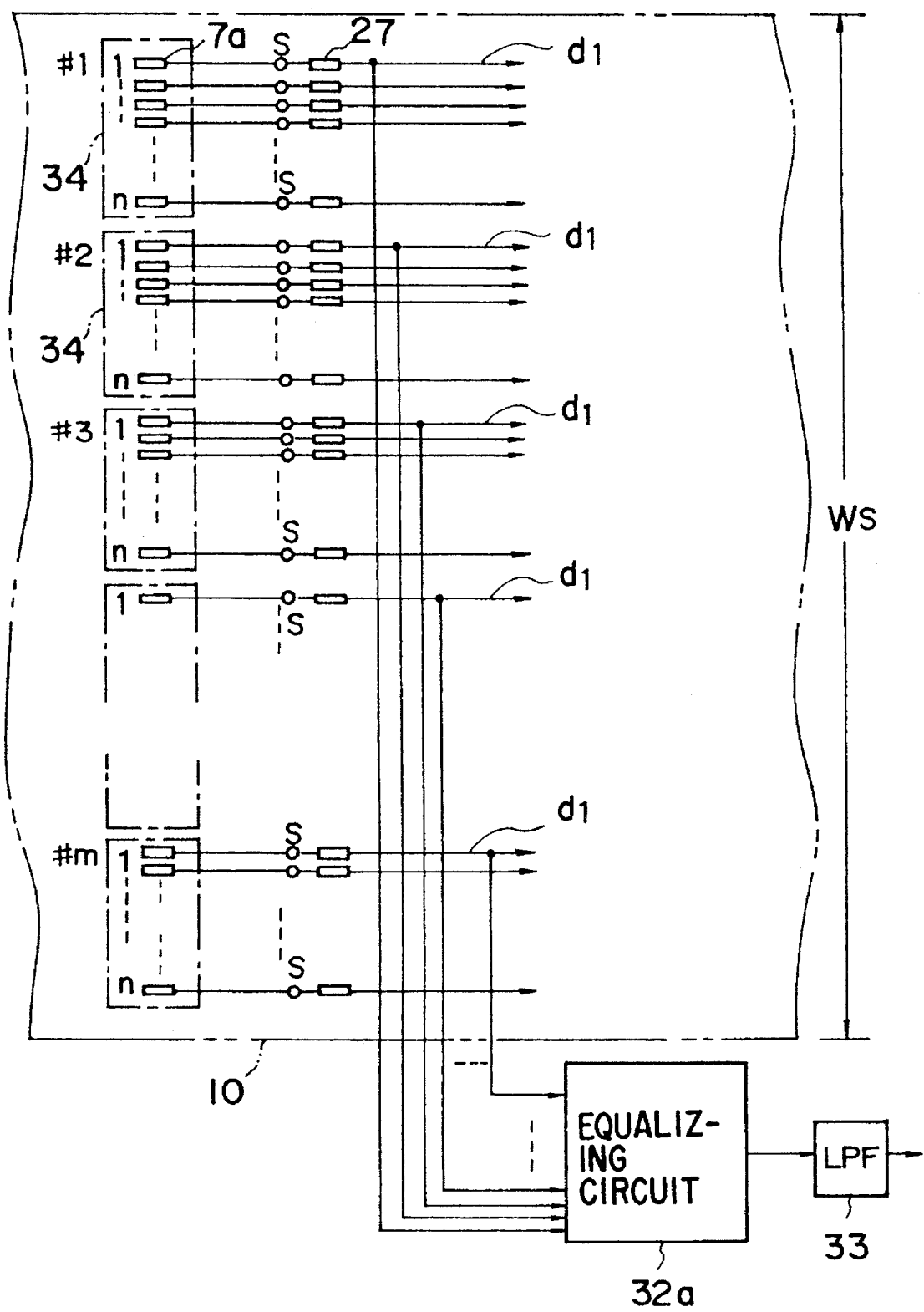
FIG. 8 is a block diagram showing the electrical structure of a magnetic detector according to another embodiment of the present invention.

FIG. 8 is a block diagram showing the main section of a magnetic detector according to another embodiment of the present invention. The components identical to those of the embodiment shown in FIG. 7 are designated by the same reference numerals and will not be described in detail.

In this embodiment, 100 to 200 magnetic sensors 7a, for example, are arranged in the widthwise direction of a thin steel strip 10. The magnetic sensors 7a are divided into blocks each consisting of 10 sensors. More precisely, they are divided into m blocks 34. The signals d1 output by magnetic detecting circuits 27 connected to the first magnetic sensors 7a of the m blocks 34 are sequentially extracted and input to an equalizing circuit 32a. The equalizing circuit 32a equalizes the m output signals d1, producing an equalized signal, and supplies the equalized signal to a low-pass filter 33.

The equalizing circuit 32a can therefore be more simple than the equalizing circuit 32 used in the embodiment illustrated in FIG. 7.

The advantages of the magnetic detectors of FIGS. 7 and 8, which incorporate the compensating coil 22, will be described with reference to the data obtained of the actual detectors made.

In the embodiments, the floating flux resulting from the moving of the thin steel strip 10 having no defects at all will ultimately not cross each of the magnetic sensors 7a. As a result, the output signal d of each magnetic sensor 7a contains no low-frequency component g. The output signal d will not be saturated even if the sensitivity of each sensor 7a is increased. Hence, the sensitivity of each magnetic sensor 7a can easily be enhanced.

In order to confirm the advantages described above, the inventors hereof conducted various comparative experiments, in which thin steel strips 10 were used, a low-frequency signal corresponding to the low-frequency component g was fed back (feedback performed), and the switch 25 was opened (no feedback performed). The results obtained are shown in FIGS. 9 to 13.

Figure 9:
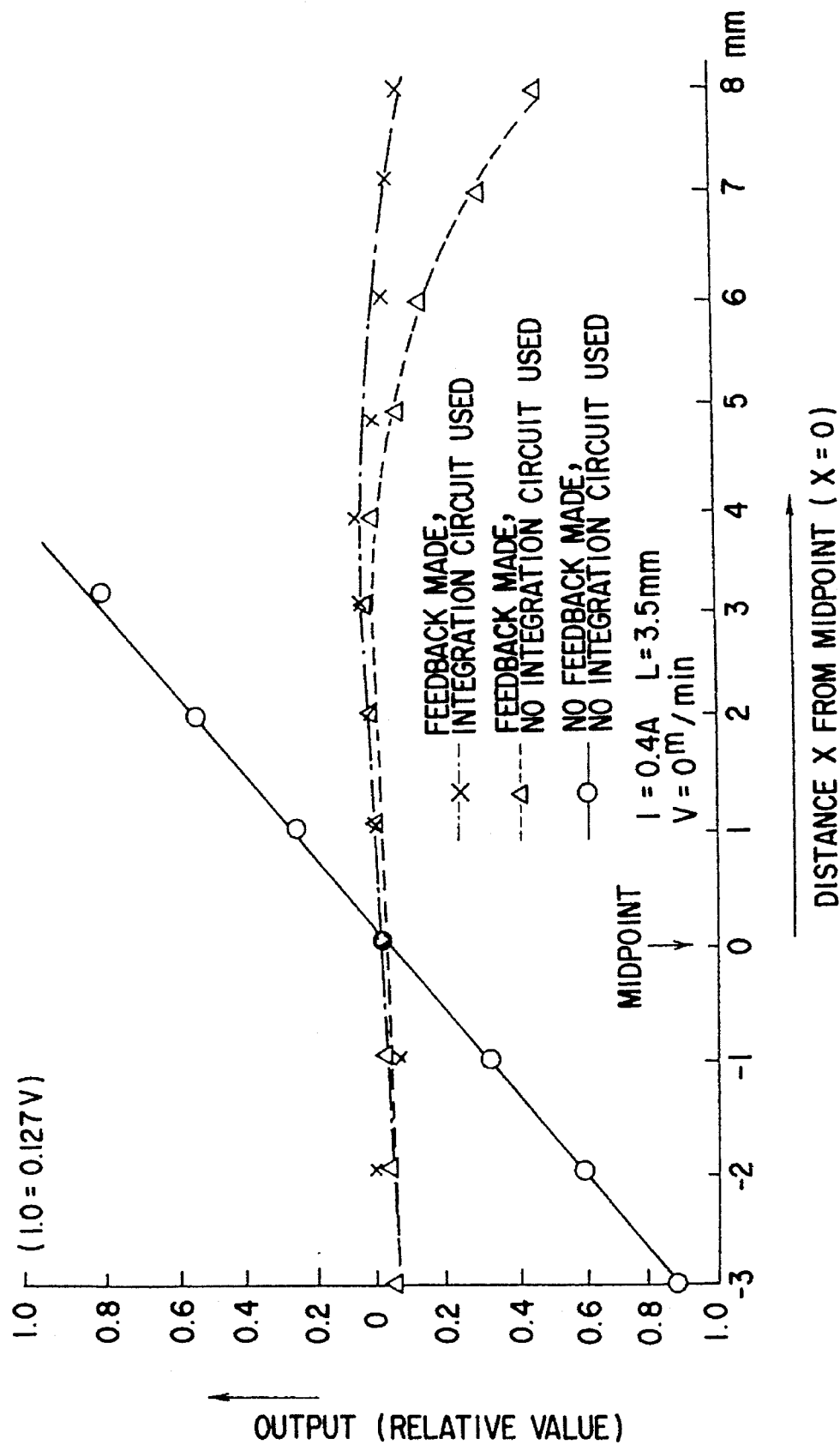
FIG. 9 is a diagram representing the relation which the position of a sensor and an output signal level actually had when the detector performed magnetic detection on a flawless thin steel strip.

First, the exciting current I of the magnetizing coil 6 incorporated in the magnetizer 4 was set at 0.4 A before a thin steel strip 10 having no defects was moved (hence, V=0). Then, each magnetic sensor 7a was moved in the horizontal direction for −3 mm to +3 mm with respect to the midpoint (X=0) between the magnetic poles 4a and 4b, and the level of the output signal d to be input to the high-pass filter 28 was measured. FIG. 9 is a diagram showing the level of each signal, which was actually measured, in terms of relative value.

Figure 47:
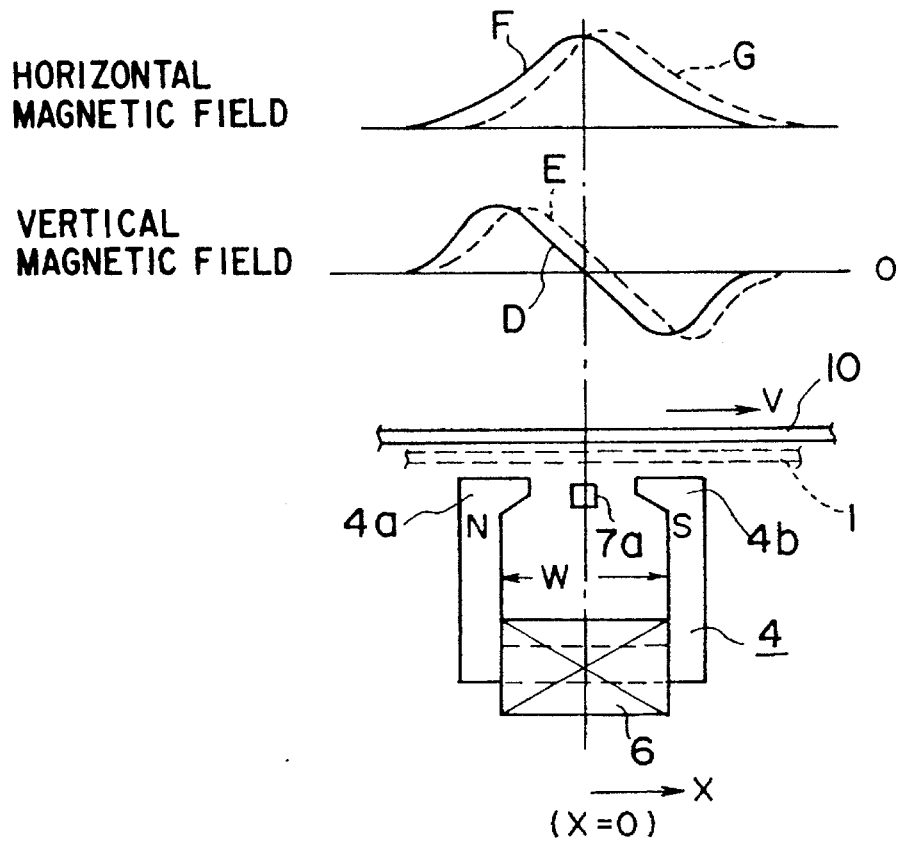
FIG. 47 is a diagram showing magnetic-field distribution of a general type, which correspond to the positions of magnetic poles.
Figure 48:
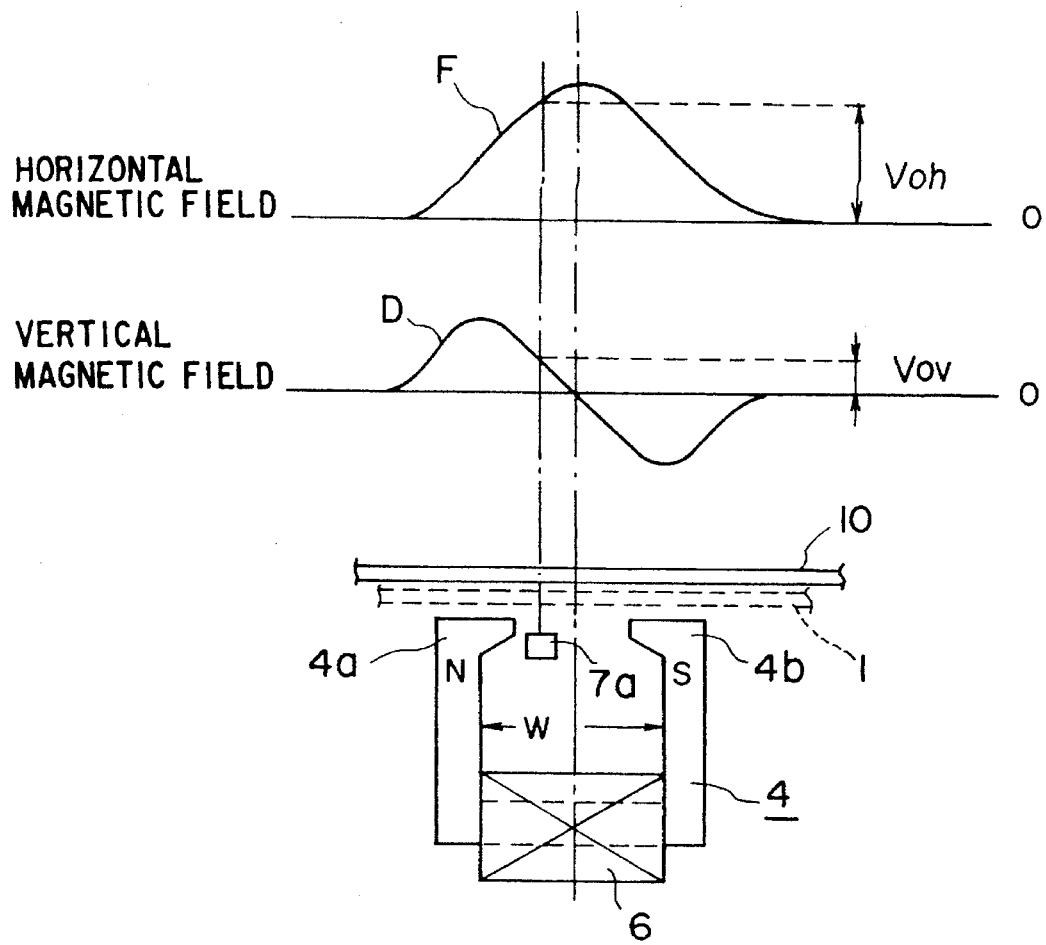
FIG. 48 is a diagram illustrating the relation between the magnetic-field distributions, on the one hand, and the fixed bias voltage applied to the output signal of a magnetic sensor.

As can be understood from these results, if the switch 25 is turned on, causing the compensating coil 22 to generate magnetic in the vertical magnetic-field distribution D shown in FIG. 47 extending to cancel out the floating flux corresponding to the vertical magnetic-field distribution D shown in FIG. 47, it is possible to set the output signal of each magnetic sensor 7a at a predetermined level which is substantially zero, despite the displacement of the sensor 7a over a long distance from the −3 mm point to the +3 mm point. With the conventional detector it is necessary to place each magnetic sensor 7a, precisely at the midpoint between the magnetic poles 4a and 4b. In the embodiments of the invention, the influence of the floating flux resulting from the vertical magnetic-field distribution D can be removed from the output signal d even if the magnetic sensors 7a are not placed exactly at the midpoint (x=0), provided that they are positioned within ±3 mm from the midpoint (X=0).

In FIG. 9, the lines showing the characteristics recorded when no feedback was made are substantially symmetrical with respect to the point of X=0 and the point of relative output of 0. The line showing the characteristic recorded when feedback was made is substantially symmetrical to the line passing the point of x=0 and perpendicular to the X axis. To facilitate understanding, only parts of these characteristics are indicated in FIG. 9, just the same as in FIG. 10 which will be referred to later.

Figure 49:
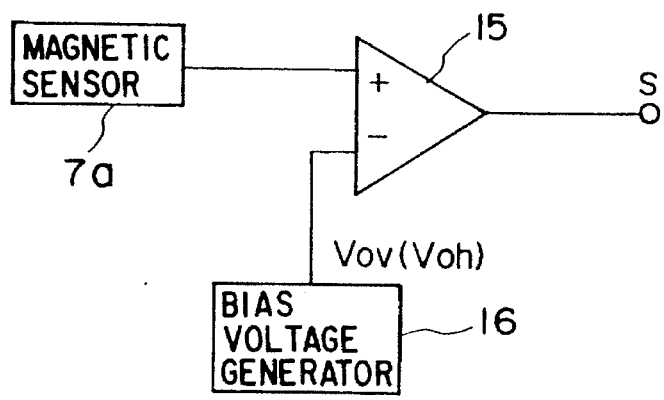
FIG. 49 is a diagram showing a bias circuit for applying a fixed bias voltage to the output signal of the magnetic sensor.
Figure 50:
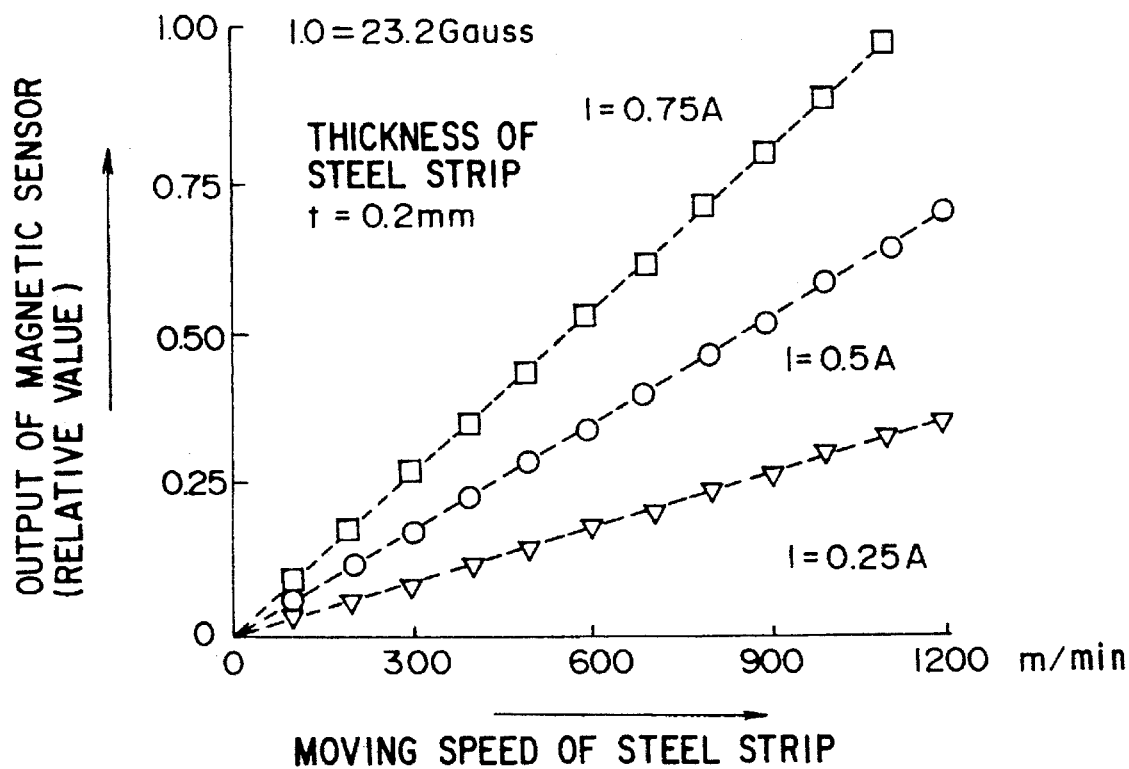
FIG. 50 is a diagram illustrating the relation between the moving speed of a thin steel strip and the level of a signal output by the magnetic sensor incorporated in the conventional magnetic detector.
Figure 51:
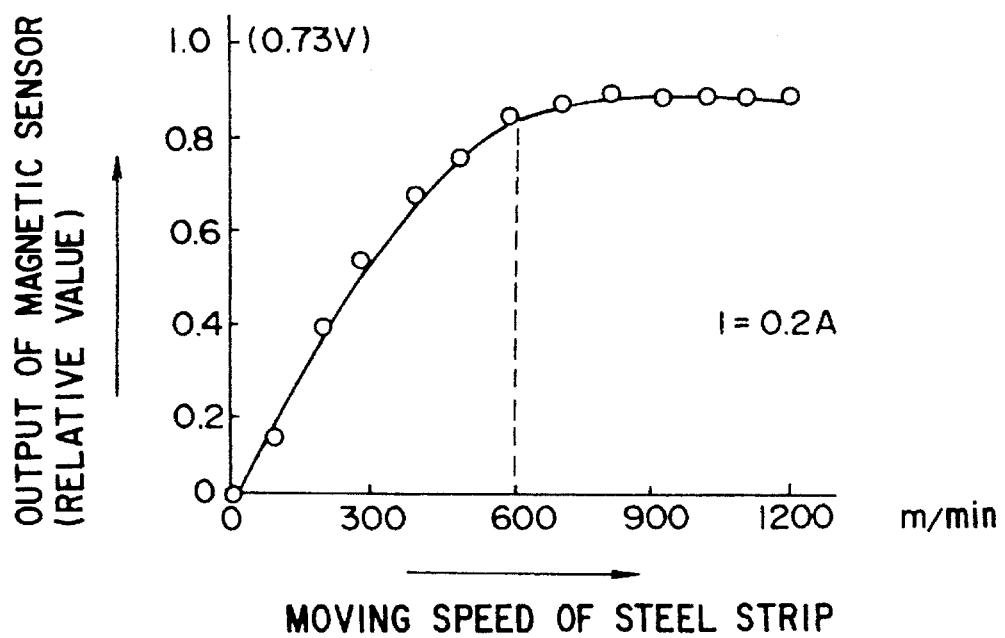
FIG. 51 is a diagram representing another relation between the moving speed of a thin steel strip and an output-signal level, which was recorded of the conventional magnetic detector.
Figure 52:
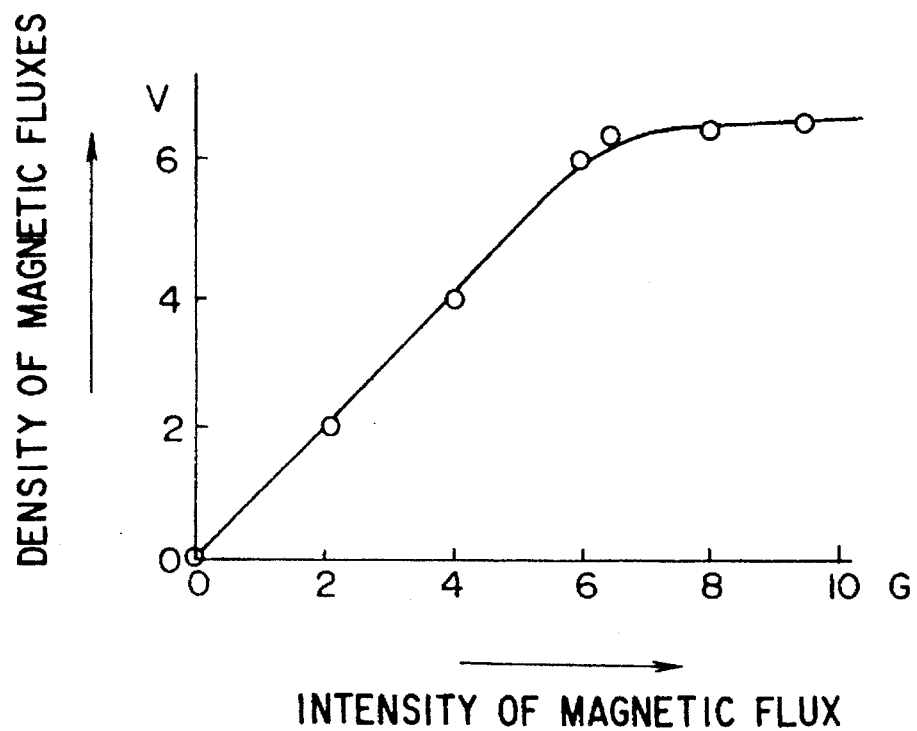
FIG. 52 is a diagram showing the relation between the density of magnetic fluxes and an output-signal level, which was recorded by the conventional magnetic detector.
Figure 53:
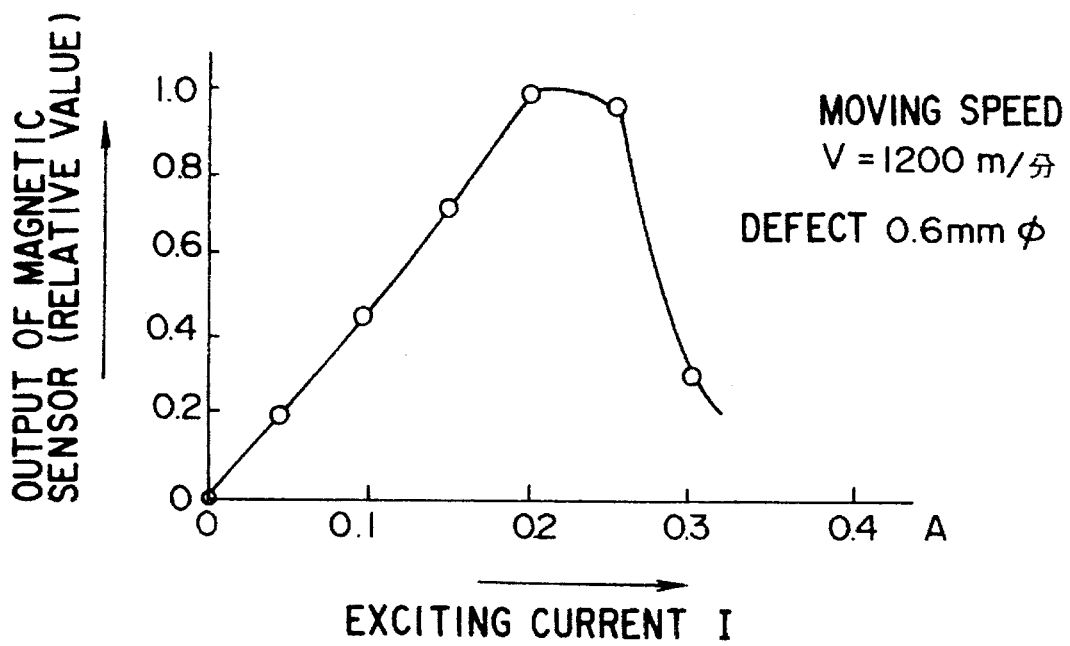
FIG. 53 is a diagram indicating the relation between an exciting current and an output-signal level, which was recorded by the conventional magnetic detector.

Hence, even if the fixed bias circuit shown in FIG. 49 is not connected to the terminal S, it is possible to fully eliminate the influence of the floating magnetic field which corresponds to the vertical magnetic-field distribution.

Figure 10:
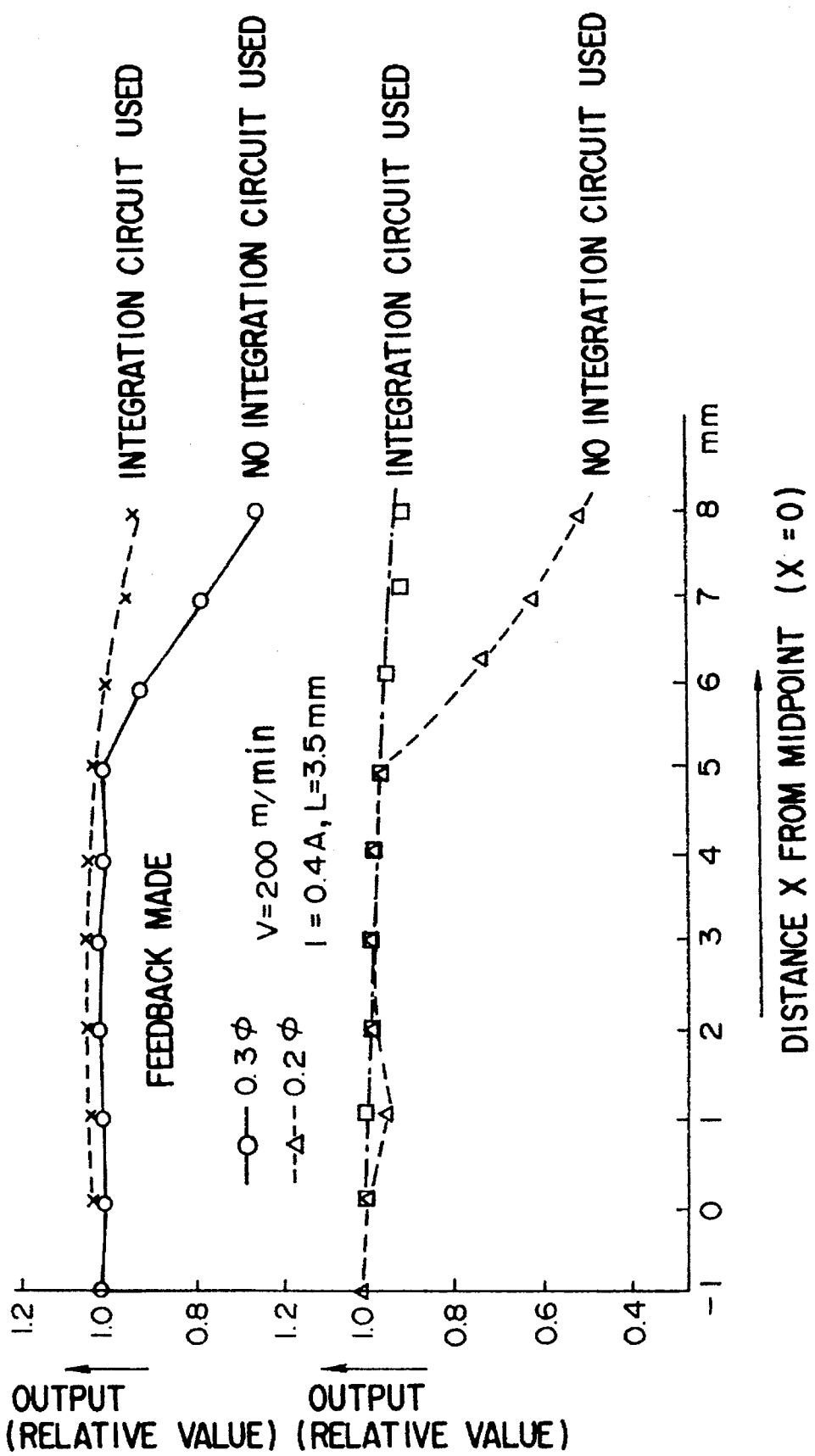
FIG. 10 is a diagram representing the relation which the position of the sensor and the output-signal level actually had when the detector performed magnetic detection on a thin steel strip having a defect.
Figure 11:
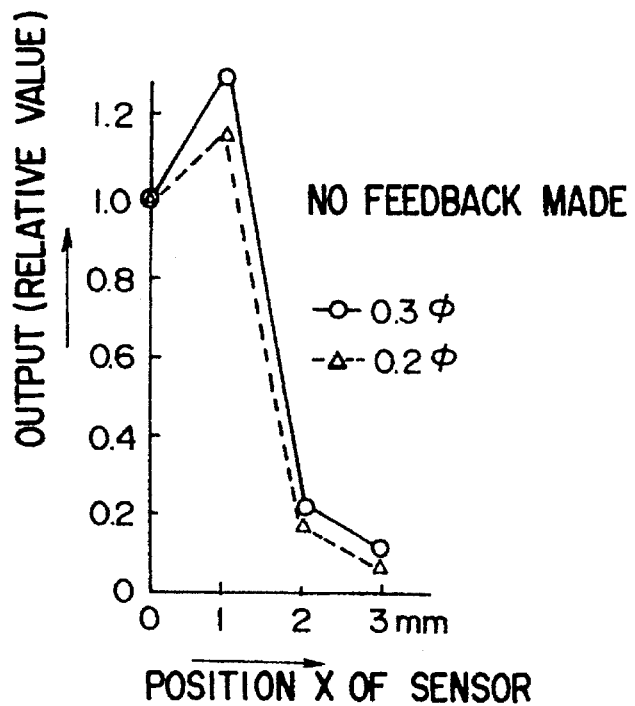
FIG. 11 is a diagram representing the relation which the position of the sensor and the output signal level actually had when a conventional detector performed magnetic detection on a thin steel strip having a defect.

Next, a thin steel strip 10, which had two standard defects having diameters of 0.2 mm and 0.3 mm, respectively, was moved at a constant speed (V= 200 m/min). While the strip 10 was moving, the switch 25 was turned on (thus, making feedback), and each magnetic sensor 7a was gradually displaced in the moving direction of the strip, for a distance of 8 mm. The level of the signal d of each sensor 7a output in this process was measured. The results were as indicated in FIG. 10, in which the level of each signal is represented in terms of relative value. Further, an experiment which was identical, except that the switch 25 was left turned off (thus making no feedback), was conducted, obtaining the results which are shown in FIG. 11.

As has been described, a floating flux is generated when the thin steel strip 10 is moved. The results of the experiment performed on the conventional detector and shown in FIG. 11 indicate that the levels of the standard-defect signals greatly fluctuated under the influence of the floating flux when each magnetic sensor 7a was displaced about 3 mm from the midpoint. By contrast, the results of the experiment on the detector of this invention and represented in FIG. 10 indicate that the levels of the standard-defect signals little fluctuated even when each magnetic sensor 7a at point X was displaced about 5 mm from the midpoint.

Figure 12:
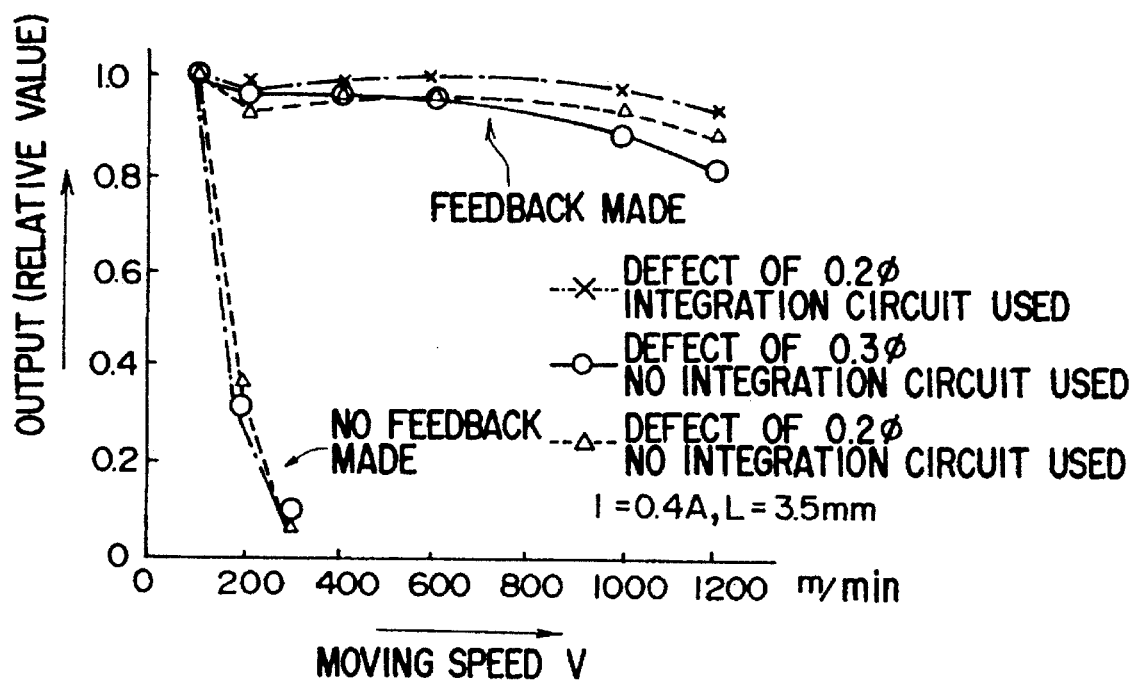
FIG. 12 is a diagram illustrating the relation between the moving speed of a thin steel strip and the level of a signal output by the magnetic sensor incorporated in the detector according to the invention.

Then, the same thin steel strip 10, having two standard defects having diameters of 0.2 mm and 0.3 mm, was moved at a speed V changing from 200 m/min to 1200 m/min. While the strip 10 was moving in this way, the switch 25 was turned on, and the level of each output signal d was measured. Also, another experiment was conducted under the same conditions, but the switch 25 was left turned off. The results of these experiments are shown in FIG. 12, in which the level of each signal is represented in terms of relative value.

As can be understood from this figure, particularly from the curves denoted by "FEEDBACK MADE," the detector of the invention can detect each defect from a virtually constant, high-level signal, even if the moving speed V changes greatly. In other words, even if the speed V varies, the signal level representing the size of the defect detected little changes, whereby the size of the defect can be measured more quantitatively. In addition, the efficiency of the flaw detection performed on the thin steel strip 10 in the inspection line can be much enhanced, merely by increasing the moving speed V of the strip 10.

Another experiment was performed. The magnetic sensors 7a were positioned at the midpoint (X=0), the cut-off frequency fc of the high-pass filters 28 was set at 1500 Hz, and a thin steel strip 10 having a standard defect having a diameter of 0.6 mm was moved at speed V of 1200 m/min. Under these conditions, the exciting current I supplied to the magnetizer 4 was changed from 0 A to 0.6 A, and the levels of the defect signals e output by the high-pass filters 28 were measured. The results are shown in FIG. 13, in which the level of each signal is represented in terms of relative value.

As the exciting current I is increased, the level of the defect signal e rises. Nonetheless, if the switch 25 is turned off (making no feedback), the signal level will be saturated when the exciting current I is about 0.2 A. If the switch 25 is turned on, however (making feedback), the level of the defect signal e continues to rise until the exciting current I increases to about 0.5 A. The detection sensitivity can, therefore, be enhanced easily by increasing the exciting current supplied to the magnetizing coil 6 of the magnetizer 4.

Thus, the moving speed V of the thin steel strip 10 can be increased, the detection sensitivity can easily be enhanced by increasing the exciting current, and the magnetic sensors 7a need not be positioned with precision. The magnetic detector according to the present invention can maintain its high measuring accuracy even if installed in poor measuring conditions inherent in the manufacture line in a factory.

Figure 13:
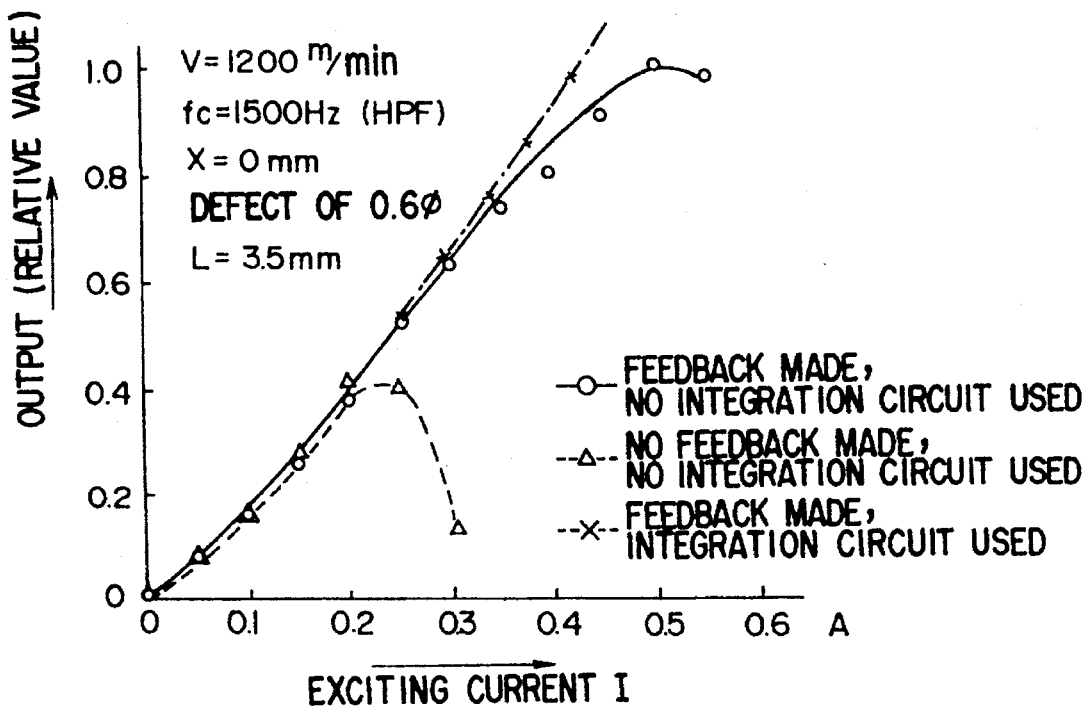
FIG. 13 is a diagram indicating the relation between the exciting current and the output-signal level, which was observed in the detector according to the invention.
Figure 14:
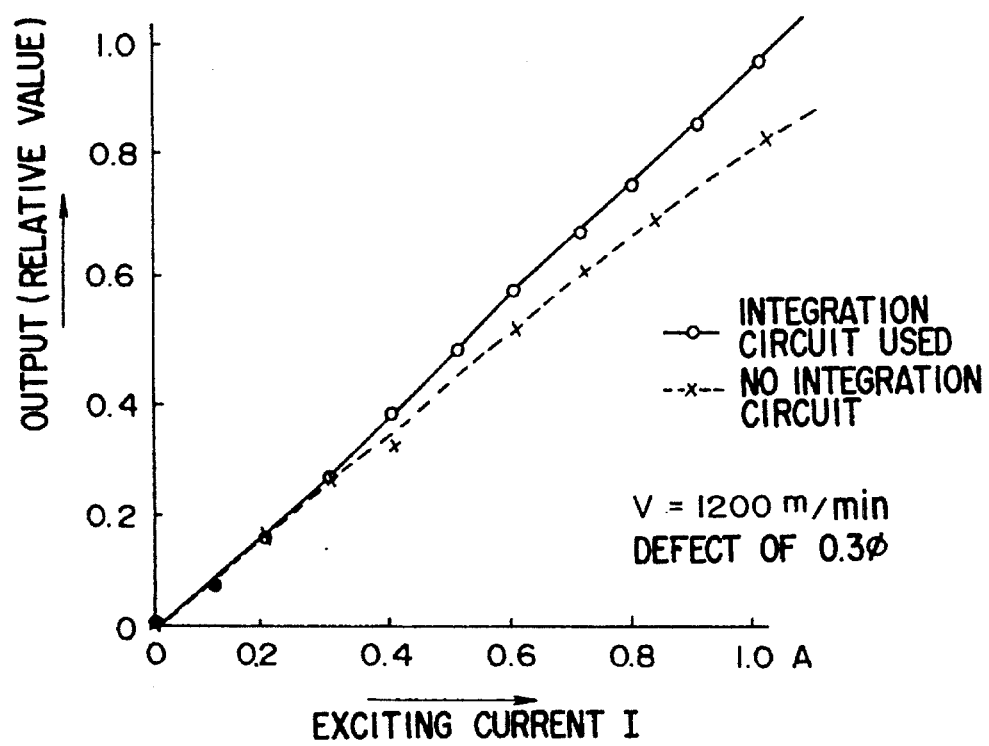
FIG. 14 is a diagram showing the relation which the exciting current and the output-signal level had when an integration circuit was used, and the relation which the exciting current and the output-signal level had when no integration circuit was used.

FIG. 14 shows how the level of the defect signal e output by the high-pass filter 28 actually rose as the exciting current I was increased to 1.0 A under the same condition as with the case shown in FIG. 13. The signal output in the case of "NO INTEGRATION CIRCUIT USED" assumed non-linear relation with the exciting current when its level rose to 0.3 (relative value) or more. Hence, the characteristic of the embodiment must be improved further.

Figure 15:
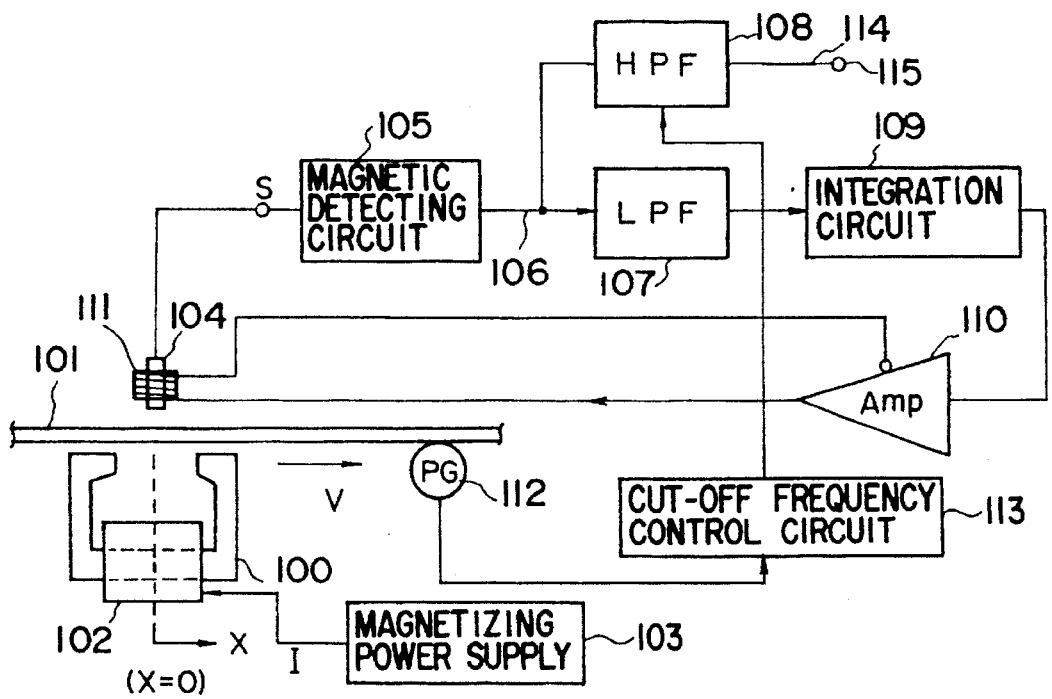
FIG. 15 is a block diagram showing a magnetic detector according to an embodiment of the invention.

FIG. 15 is a block diagram showing a magnetic detector according to an embodiment of the invention. The components identical to those of the embodiment shown in FIG. 1 are designated by the same reference numerals and will not be described in detail.

In the detector according to this embodiment, an integration circuit 109 is connected between a low-pass filter 107 and an amplifier 110.

A magnetic detecting circuit 105 converts a signal output by a magnetic sensor 104 into an output signal 106 which corresponds to the intensity of a magnetic flux crossing the magnetic sensor 104. The output signal 106 is input to the low-pass filter 107 and a high-pass filter 108. The low-pass filter 107 extracts the low-frequency signal component contained in the output signal 106. The integration circuit 109 converts the low-frequency signal component, extracted by the low-pass filter 107, into a substantially DC bias signal, which is supplied to the amplifier 110. The bias signal amplified by the amplifier 110 is supplied to a compensating coil 111 wound around the circumferential surface of the magnetic sensor 104.

In the magnetic detector thus constructed, the compensating coil 111, the magnetic sensor 104, the low-pass filter 107, the integration circuit 109, and the amplifier 110 constitute a kind of a negative feedback loop, just as in the detector of FIG. 1. Even if the moving speed V of a thin steel strip 101 varies, changing the level of the low-frequency component of the output signal 106, the negative feedback loop operates to cancel the low-frequency signal component. The resultant phenomenon is as if the external magnetic field, responsible for the low-frequency component, did not act at all. As a result, the output signal 106 of the magnetic sensor 104 comes to contain almost no low-frequency component.

Figure 16:
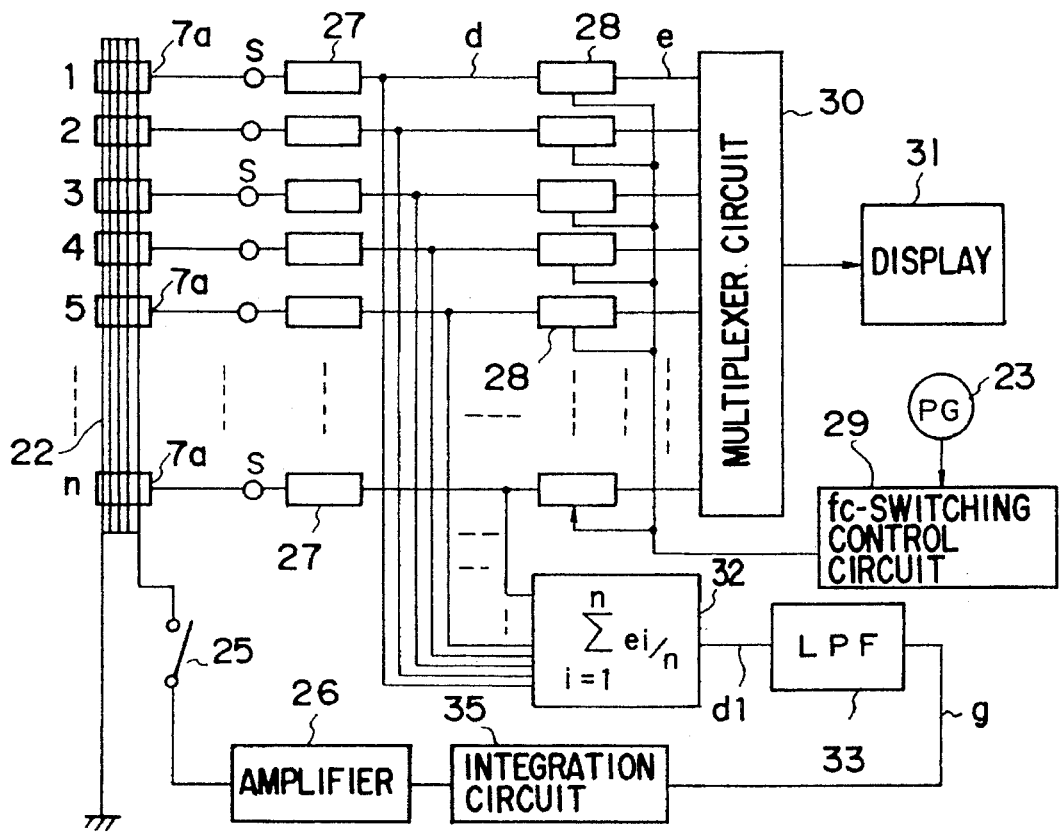
FIG. 16 is a block diagram showing the electrical structure of the magnetic detector.

FIG. 16 is a block diagram showing the electrical structure of the magnetic detector shown in FIG. 15, not showing the magnetizer 4 contained in the lower hollow roll 1. The components identical to those of the embodiment shown in FIG. 7 are designated by the same reference numerals and will not be described in detail.

In this embodiment, the integration circuit 35 is connected between the low-pass filter 33 and the amplifier 26. Thus, the low-frequency signal component g extracted by the low-pass filter 33 is input to the integration circuit 35. The integration circuit 35 integrates the low-frequency signal component g, converting the same into a substantially DC bias signal. The bias signal output from the integration circuit 35 is amplified by the amplifier 26 and supplied to the compensating coil 22 through a switch 25.

The advantage achieved by connecting the integration circuit between the low-pass filter and the amplifier, as is illustrated in FIGS. 15 and 16, will be explained, with reference to FIGS. 9, 10, 11, 13, and 14.

Referring to FIGS. 9 and 10, the tolerance of the position of the magnetic sensor 7a is about 3 to 4 mm from the midpoint in the embodiment using no integration circuit. This tolerance greatly increases to about 8 mm if an integration circuit is used. This makes it easy to position the component in manufacturing the magnetic detector. As is shown in FIG. 12, the use of the integration circuit can reduce the decrease in the level of the signal output by the magnetic sensor 7a in the case where the moving speed V of the thin steel strip 10 changes. In other words, even if the speed V greatly changes, the accuracy of detecting the size of a defect can be maintained at a substantially constant value. The defect-detecting accuracy can, thus, remain high at all times.

Further, as is shown in FIG. 14, owing to the use of the integration circuit, the relation between the exciting current I and the output signal can remain linear, provided the exciting current I is 1.0 A or less. In the embodiment of FIG. 7 which has no integration circuit, the output signal is about to be saturated when the exciting current is approximately 3.5 A. By contrast, in the embodiment of FIG. 16, the signal does not appear to be saturated until the current is increased to about 1.0 A. Hence, the detection sensitivity can easily be enhanced, merely by increasing the exciting current I.

Figure 17:
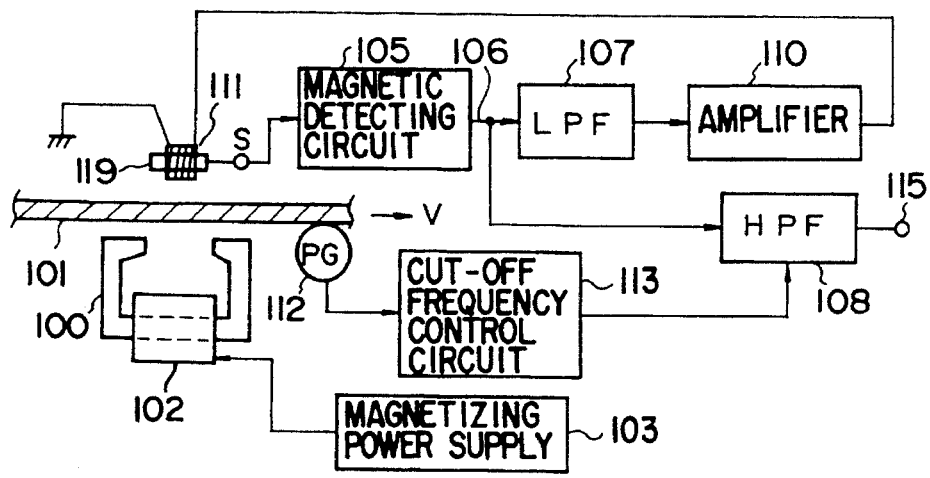
FIG. 17 is a block diagram illustrating the electrical structure of a magnetic detector according to still another embodiment of the invention.

FIG. 17 is a block diagram showing a magnetic detector according to still another embodiment of the present invention. The components identical to those of the embodiment shown in FIG. 1 are designated by the same reference numerals and will not be described in detail.

In this embodiment, a horizontal-type magnetic sensor 119 is used for detecting magnetic fluxes extending parallel to a thin steel strip 101, instead of the vertical-type magnetic sensor 104 shown in FIG. 1. A signal from the horizontal-type magnetic sensor 119 is 10 input to a magnetic detecting circuit 105. The horizontal-type magnetic sensor 119 detects the floating flux at the midpoint (X=0) in the horizontal magnetic-field distribution F illustrated in FIG. 47. At the midpoint (X=0) in the horizontal magnetic-field distribution F, the flux changes rather moderately, whereas the leakage flux resulting from a defect changes greatly and has a steep waveform. It is therefore possible to detect the waveform representing the defect, fully distinguished from other waveforms.

The signal 106 output by the magnetic detecting circuit 105 is input to a low-pass filter 107. The signal is processed by the low-pass filter 107 and the other components following this filter, in substantially the same way as in the embodiment of FIG. 1. Therefore, this embodiment achieves almost the same advantage as the embodiment of FIG. 1.

Figure 18:
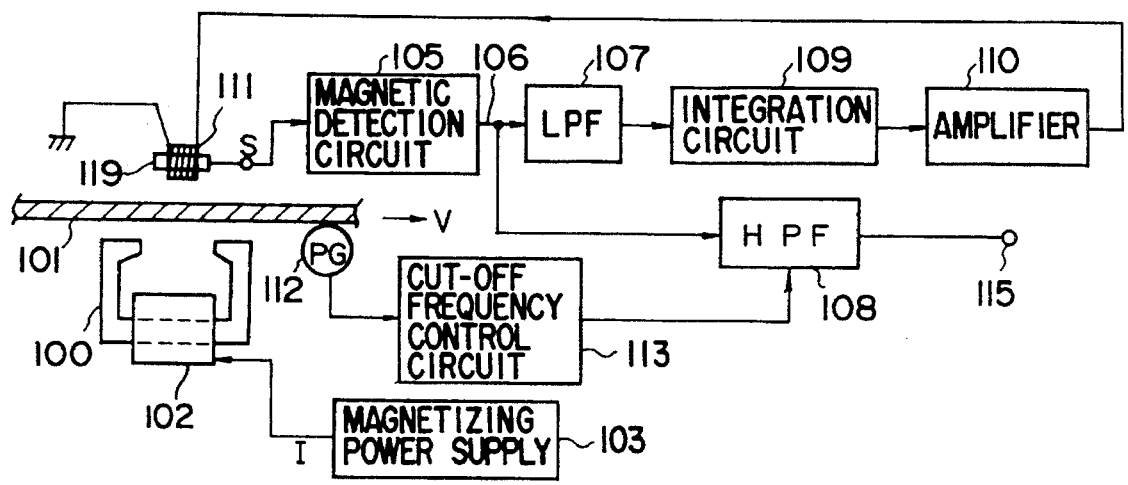
FIG. 18 is a block diagram showing the electrical structure of a magnetic detector according to a further embodiment of the present invention.

FIG. 18 is a block diagram showing a magnetic detector according to a further embodiment of this invention. The components identical to those of the embodiment shown in FIG. 17 are designated by the same reference numerals and will not be described in detail.

In this embodiment, an integration circuit 109 is connected between a low-pass filter 107 and an amplifier 110. Except for this point, the detector is identical to the magnetic detector shown in FIG. 17. It therefore achieves almost the same advantage as the embodiment of FIG. 15, which differs from the embodiment of FIG. 1 in that it incorporates the integration circuit 109.

Figure 19:
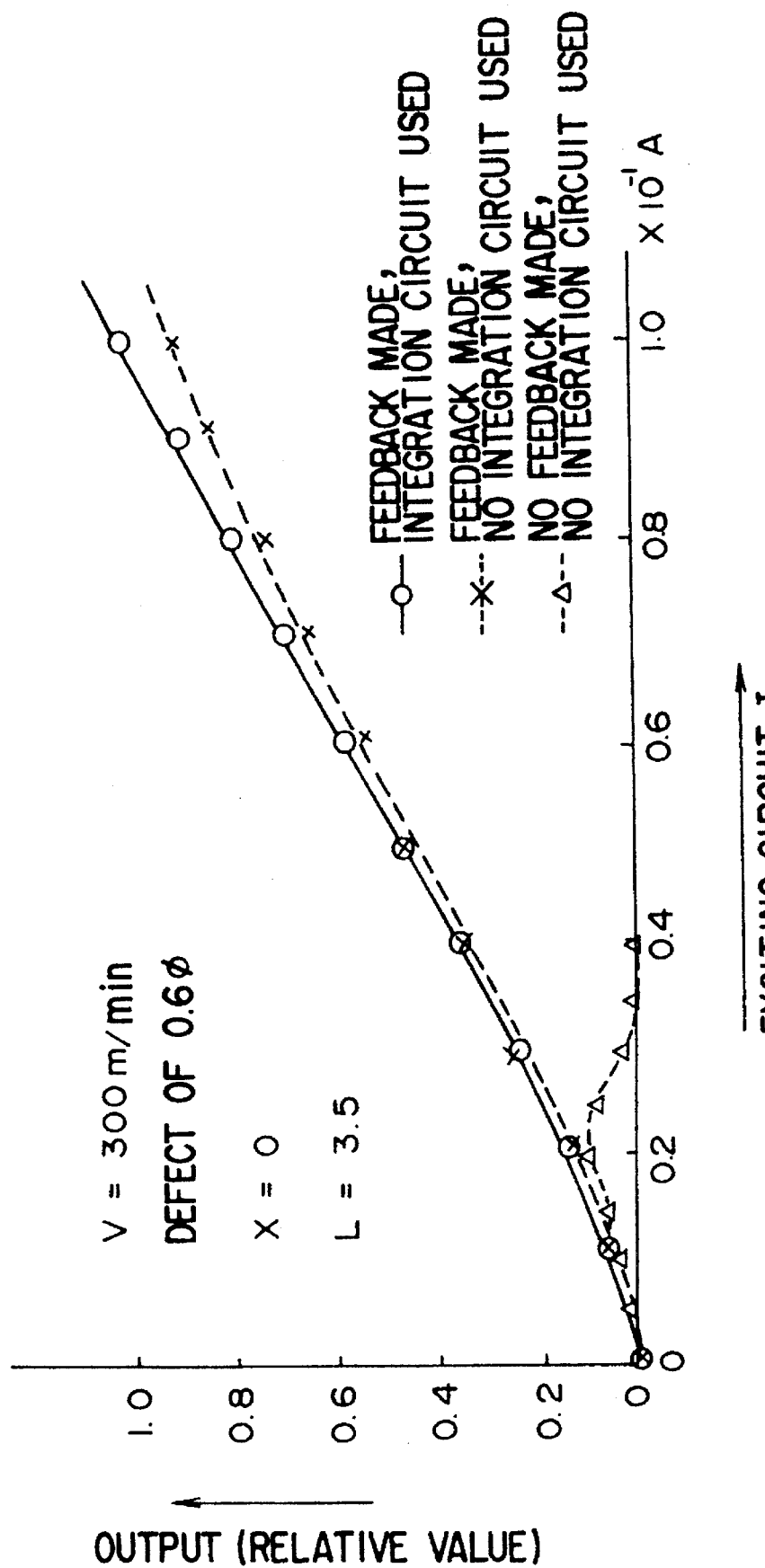
FIG. 19 is a diagram representing the relation between an exciting current and an output-signal which was observed in the embodiment of FIGS. 17 and 18.

FIG. 19 is a diagram representing the values actually measured in the embodiments of FIGS. 7 and 16 in which horizontal-type magnetic sensors 7b are used in place of vertical-type magnetic sensors 7a.

If the switch 25 is opened, not feeding the low-frequency signal or the bias signal back to the compensating coil 22, the output signal of each magnetic sensor 7b will be saturated when the exciting current I supplied to the magnetizer 4 is increased to about 0.02 A, and will fall to 0 when the exciting current I is further increased to 0.04 A.

In contrast to this, if the low-frequency signal is fed back to the compensating coil 22, it is possible to increase the exciting current I up to 0.1 A. Moreover, the use of the integration circuit 109 enables the output signal of the magnetic sensor 7b to increase, substantially in proportion to the exciting current I, until the current I is increased to 0.1 A.

Figure 20:
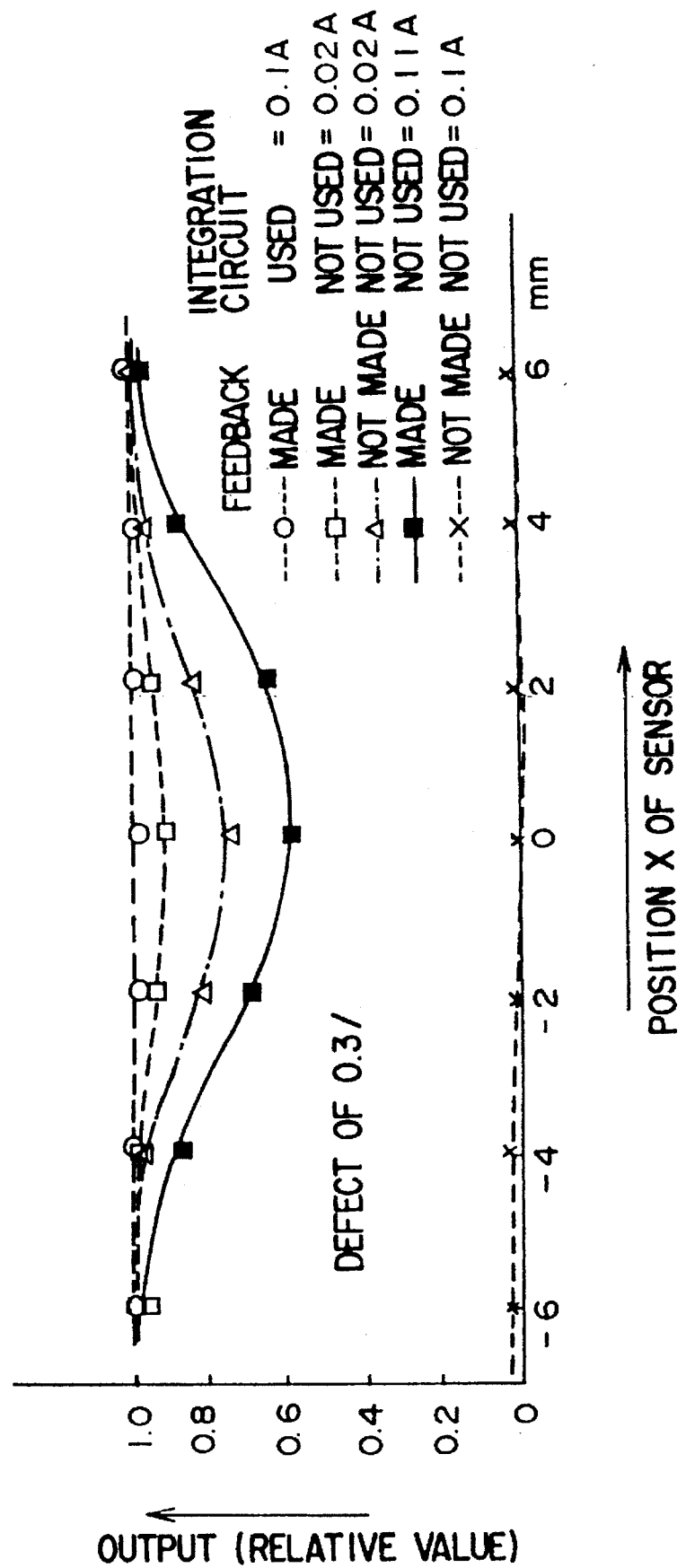
FIG. 20 is a diagram indicating the relation between the position of a sensor and an output-signal level which was observed in the embodiments of FIGS. 17 and 18.

FIG. 20 is a diagram indicating the relation between the position X of the horizontal-type magnetic sensor 7b and the level (relative value) of the signal output by the sensor 7b, which has been actually observed. The position X of the sensor is the distance from the midpoint (X=0) between the magnetic poles 4a and 4b of the magnetizer 4. As is clear from FIG. 20, for the same exciting current I, the level of the signal output by the magnetic sensor 7b is less influenced by the position of the sensor when a low-frequency signal or a bias signal is fed back to the compensating coil 22 than when neither signal is fed back to the coil 22. Thus, no high precision is required in positioning the horizontal-type magnetic sensor 7a, as in positioning the vertical-type magnetic sensor 7a.

Figure 21:
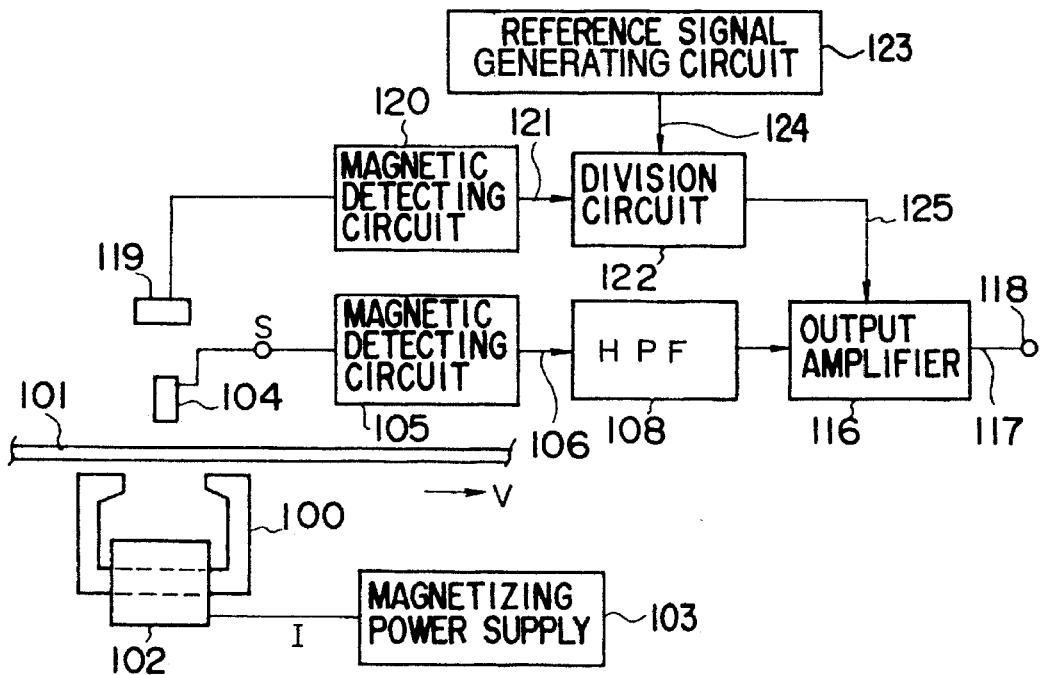
FIG. 21 is a block diagram showing a magnetic detector according to a further embodiment of this invention.

FIG. 21 is a block diagram showing a magnetic detector according to a further embodiment of this invention. The components identical to those of the embodiment shown in FIG. 1 are designated by the same reference numerals and will not be described in detail.

In this embodiment, the output signal of a vertical magnetic sensor 104 for detecting a leakage flux resulting from a magnetically defective portion within a thin steel strip 101 or in the surface thereof is converted by a magnetic detecting circuit 105 into an output signal 106 which corresponds to the intensity of the flux. The output signal 106 is input to a high-pass filter 108. The high-pass filter 108 removes the low-frequency signal component contained in the output signal 106. A signal output by the high-pass filter 108 is amplified by an output amplifier 116 and subsequently supplied, as a defect signal 117, to an output terminal 118.

A horizontal-type magnetic sensor 119 is arranged adjacent to the vertical-type magnetic sensor 104. The horizontal-type magnetic sensor 119 detects the magnetic flux located near the peak of the angle-shaped horizontal magnetic-field distribution F illustrated in FIG. 47.

The signal output by the horizontal-type magnetic sensor 119 is converted by a magnetic detecting circuit 120 into an output signal 121 which corresponds to the intensity of a flux crossing the magnetic sensor 119. The signal output from the magnetic detecting circuit 120 is input to a division circuit 122. A reference signal generating circuit 123 supplies a reference signal 124 having a level corresponding to a preset reference amplification factor, to the division circuit 122. The division circuit 122 divides the output signal 121 of the magnetic detecting circuit 120 by the level of the reference signal 124, generating a control signal 125, which is supplied to the output amplifier 116. The output amplifier 116 lowers the amplification factor when the control signal 125 rises to a high level, and raises the amplification factor when the control signal 125 falls to a low level.

As has been indicated, the magnetizing force on the thin steel strip 101 decreases as the moving speed V of the strip 101 increases, when the exciting current I supplied to the magnetizer 100 is controlled at the same value. Hence, the defect signal 117 falls to a low level when the moving speed V increases, even if the defect is of the same size. In the embodiment, however, the level of the signal 121 output by the horizontal-type magnetic sensor 119 falls when the magnetizing force on the thin steel strip 101 decreases. As a result of this, the amplification factor of the output amplifier 116 increases, compensating for the level fall of the defect signal 117.

Conversely, when the moving speed V of the thin steel strip 101 decreases, thus increasing the magnetizing force, the level of the signal 121 output by the horizontal-type magnetic sensor 119 rises. As a result, the amplification factor of the output amplifier 116 decreases, suppressing the increase of the level of the defect signal 117.

The horizontal-type magnetic sensor 119 detects change in the magnetizing force, which has resulted from the change in the moving speed V of the thin steel strip 101. The change in the magnetizing force, thus detected, controls the amplification factor of the output amplifier 116. Therefore, the level of the signal output from the output terminal 118 is always at the level which corresponds to the size of the defect. This further enhances the accuracy of detecting the size of a defect.

Moreover, this embodiment can fully cope with changes in the attributes of the object, such as thickness and type. It is, therefore, useful particularly in continuous, on-line inspection of objects which differ in thickness or quality.

Figure 22:
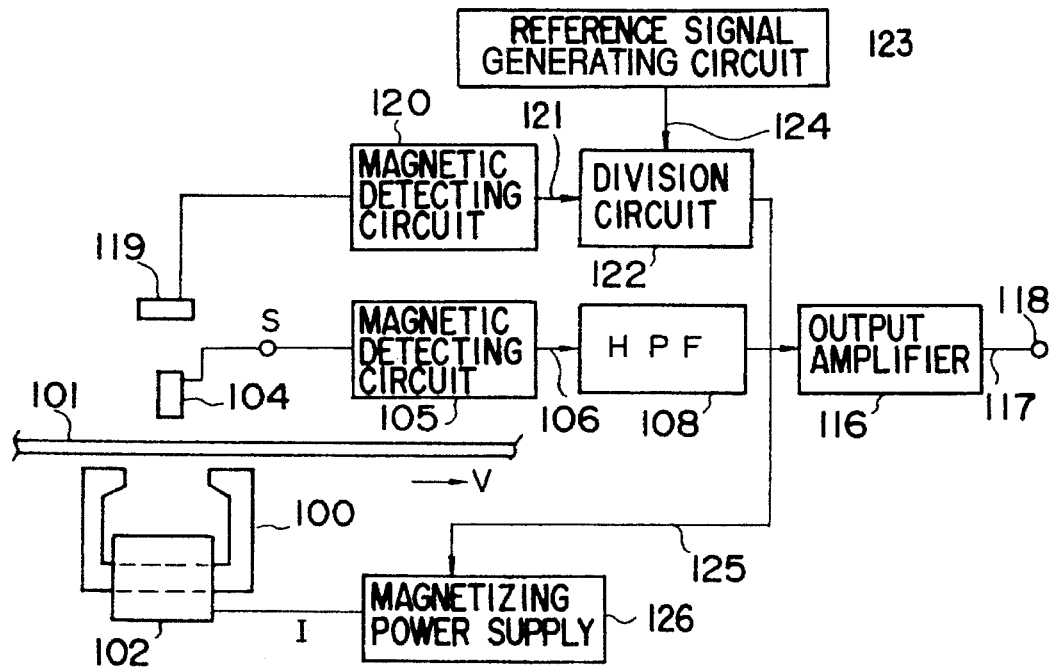
FIG. 22 is a block diagram illustrating a magnetic detector according to another embodiment of the present invention.

FIG. 22 is a block diagram illustrating a magnetic detector according to another embodiment of the present invention. The components identical to those of the embodiment shown in FIG. 21 are designated by the same reference numerals and will not be described in detail.

In this embodiment, a control signal 125 output by a division circuit 122 is input to the control terminal of a magnetizing power supply 126. A reference signal generating circuit 123 outputs a reference signal 124 which corresponds to a reference magnetizing current. When the level of the control signal 125 rises, the magnetizing power supply 126 reduces the exciting current I for an exciting coil 102 to a value equal to or less than the reference magnetizing current. Conversely, when the level of the control signal 125 falls, the power supply 126 increases the exciting current I.

In the magnetic detector of this structure, as has been described, the magnetizing force on the thin steel strip 101 decreases as the moving speed V of the strip 101 increases. As a result, the control signal 125 falls to a low level, and the exciting current I increases, compensating for the decrease in the magnetizing force on the strip 101. Conversely, when the moving speed V of the strip 101 decreases, thus increasing the exciting current I, the exciting current I output from the magnetizing power supply 126 decreases, thereby suppressing an increase in the magnetizing force.

As the moving speed V of the thin steel strip 101 changes, the magnetizing force changes. The change in the magnetizing force, thus caused, is detected by a horizontal-type magnetic sensor 119. The exciting current I for a magnetizer 100 is changed in accordance with the detected change of the magnetizing force, whereby the magnetizing force on the thin steel strip 101 is always maintained at a constant value. The level of the defect signal 117 output from an output terminal 118 is always at the level corresponding to the side of a defect. This further enhances the accuracy of detecting the size of a defect.

Figure 23:
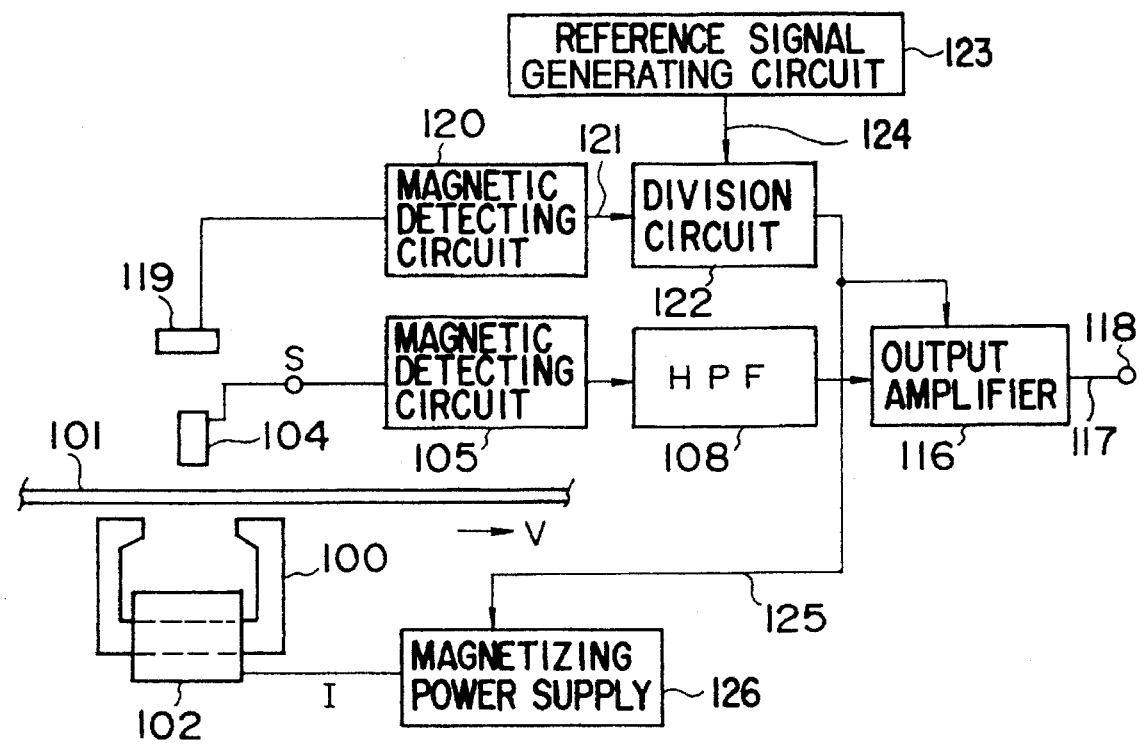
FIG. 23 is a block diagram showing a magnetic detector according to a different embodiment of the invention.

FIG. 23 is a block diagram showing a magnetic detector according to a different embodiment of the invention. The components identical to those of the embodiment shown in FIG. 22 are designated by the same reference numerals and will not be described in detail.

In this embodiment, the control signal 125 output from a division circuit 122 is input to the control terminal of a magnetizing power supply 126, and also to the control terminal of an output amplifier 116.

With the magnetic detector of this structure, the level of a defect signal 117 and that of the exciting current for a magnetizer 100 are corrected at the same time. The signal level and the current level change rapidly when the moving speed V of, for example, a thin steel strip 101 abruptly changes. The accuracy of detecting the size of a defect is therefore enhanced further.

To compare the detector of FIG. 21, in which the control signal 125 is fed back to the output amplifier 116, and the detector of FIG. 22, in which the control signal 125 is fed back to the magnetizing power supply 126, a thin steel strip 101 with a standard defect having a diameter of 0.2 mm was moved at various speeds ranging from 0 to 1200 m/min, and the level of the signal output by the horizontal-type magnetic sensor 119 was monitored while the strip 101 was moving at each speed. The results are shown in FIG. 24.

Figure 24:
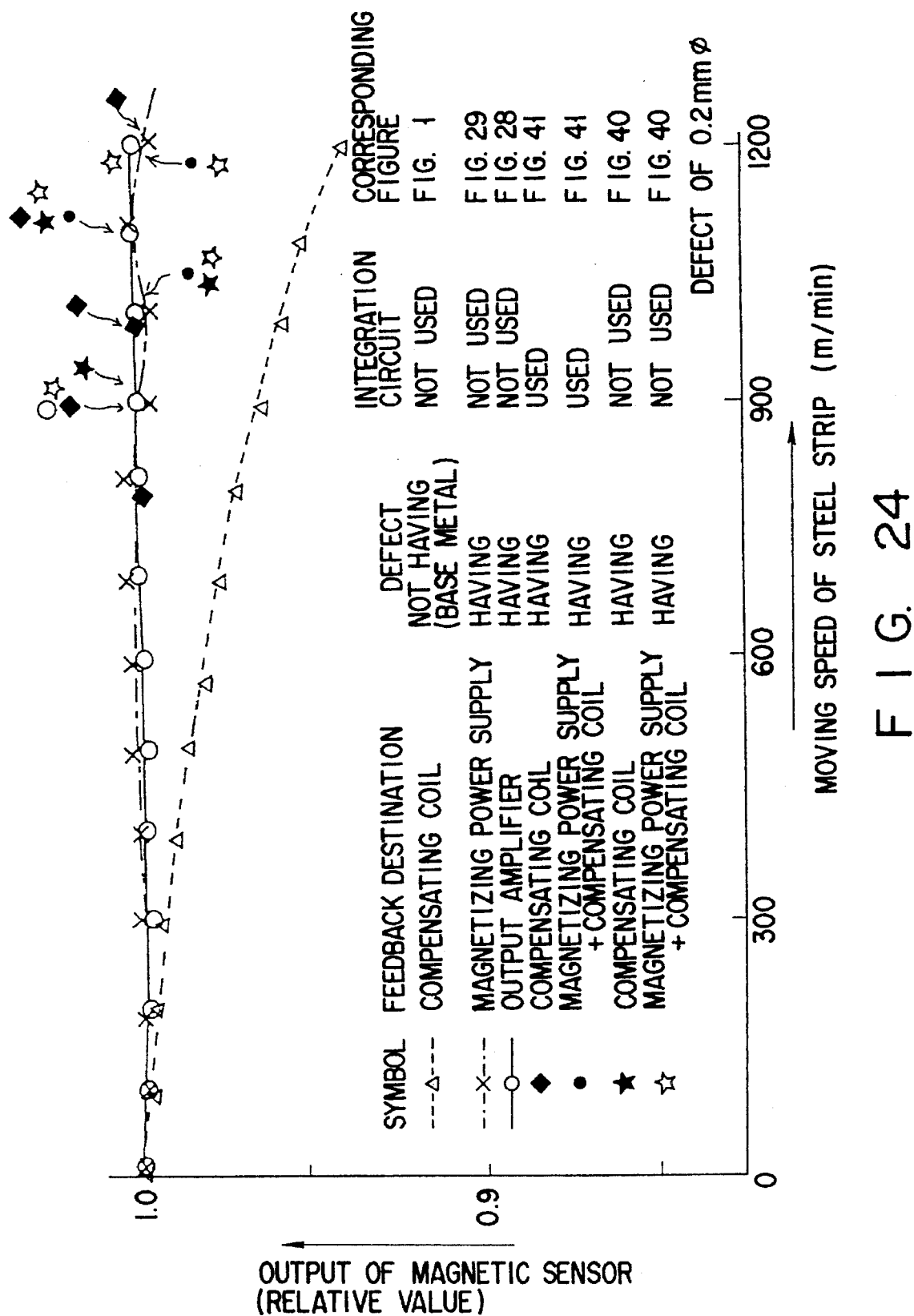
FIG. 24 is a diagram representing the relation which the moving speed of a thin steel strip and the output-signal level had in the embodiments of FIGS. 21, 22 and 23.

FIG. 24 also shows the values actually measured when the low-frequency signal output by the amplifier 110 was fed back to the compensating coil 111 only as in the embodiment of FIG. 1. In this case, use was made of a thin steel strip 101 which has no defects at all.

As is shown in the figure, the level of the output signal falls when the moving speed V of the thin steel strip 101 increases, if a low-frequency signal is fed back to a compensating coil 111. If a control signal 125 is fed back to the magnetizing power supply 126 or an output amplifier 116, however, the level of the output signal scarcely changes even when the moving speed V varies greatly. Therefore it can be understood that the accuracy of detecting the size of a defect is therefore enhanced very much.

Figure 25:
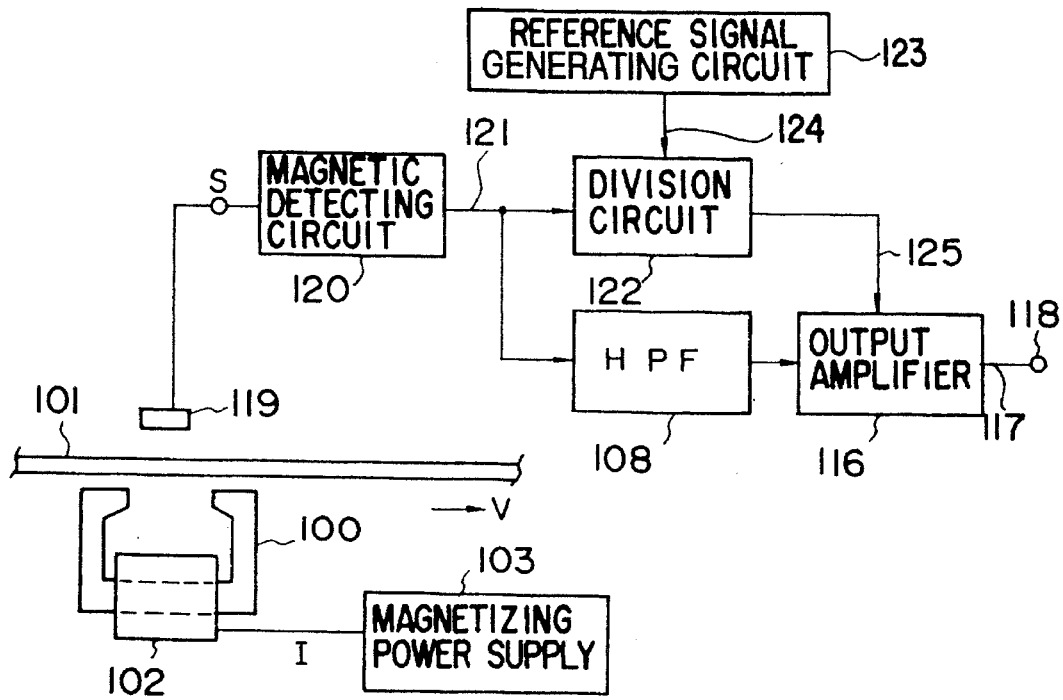
FIG. 25 is a block diagram showing a magnetic detector according to an embodiment of this invention.

FIG. 25 is a block diagram showing a magnetic detector according to an embodiment of this invention. The components identical to those of the embodiment shown in FIG. 21 are designated by the same reference numerals and will not be described in detail.

In this embodiment, a horizontal-type magnetic sensor 119 detects defects.

More specifically, the output signal of the horizontal-type magnetic sensor 119 which detects a leakage flux resulting from a magnetically defective portion within a thin steel strip 101 or in the surface thereof is converted by a magnetic detecting circuit 120 into an output signal 121 which corresponds to the intensity of the flux. The output signal 121 is input to a high-pass filter 108. The high-pass filter 108 removes the low-frequency signal component contained in the output signal 121. A signal output by the high-pass filter 108 is amplified by an output amplifier 116 and subsequently supplied, as a defect signal 117, to an output terminal 118.

The output signal 121 of the magnetic detecting circuit 120 is input to a division circuit 122. A reference signal generating circuit 123 supplies a reference signal 124 which corresponds to the reference amplification preset in the output amplifier 116, to the division circuit 122. The division circuit 122 divides the output signal 121 of the magnetic detecting circuit 121 by the level of the reference signal 124, generating a control signal 125, which is supplied to the control terminal of the output amplifier 116. The output amplifier 116 lowers the amplification factor when the control signal 125 rises to a high level, and raises the amplification factor when the control signal 125 falls to a low level.

With the magnetic detector of this structure, the horizontal-type magnetic sensor 119 detects a floating flux corresponding to the magnetic field at the midpoint (X=0) of the horizontal magnetic-field distribution F illustrated in FIG. 47, and also a leakage flux resulting from a defect. Hence, if a defect exists, the horizontal-type magnetic sensor 119 detects a composite flux which consists of the low-frequency floating flux and the leakage flux resulting from the defect and superposed on the floating flux. The high-frequency signal component contained in the output signal 121 of the magnetic detecting circuit 120 is detected by the high-pass filter 108. The defect signal 117 resulting from the defect is thereby output from the output terminal 118. Since the low-frequency signal component resulting from the floating flux is far greater than the high-frequency signal component resulting from the defect, the level of the signal input to the division circuit 122 can be regarded as almost equal to the level of the low-frequency signal component resulting from the floating flux. Hence, the amplification factor of the output amplifier 116 changes in response to the changes in the level of the floating flux. As a result, even if the moving speed V of the thin steel strip 101 changes greatly, the accuracy of detecting the size of the defect can be controlled at a substantially constant value over a broad range of the moving speed V. This embodiment can, therefore, attain advantages similar to those of the embodiment illustrated in FIG. 21.

Figure 26:
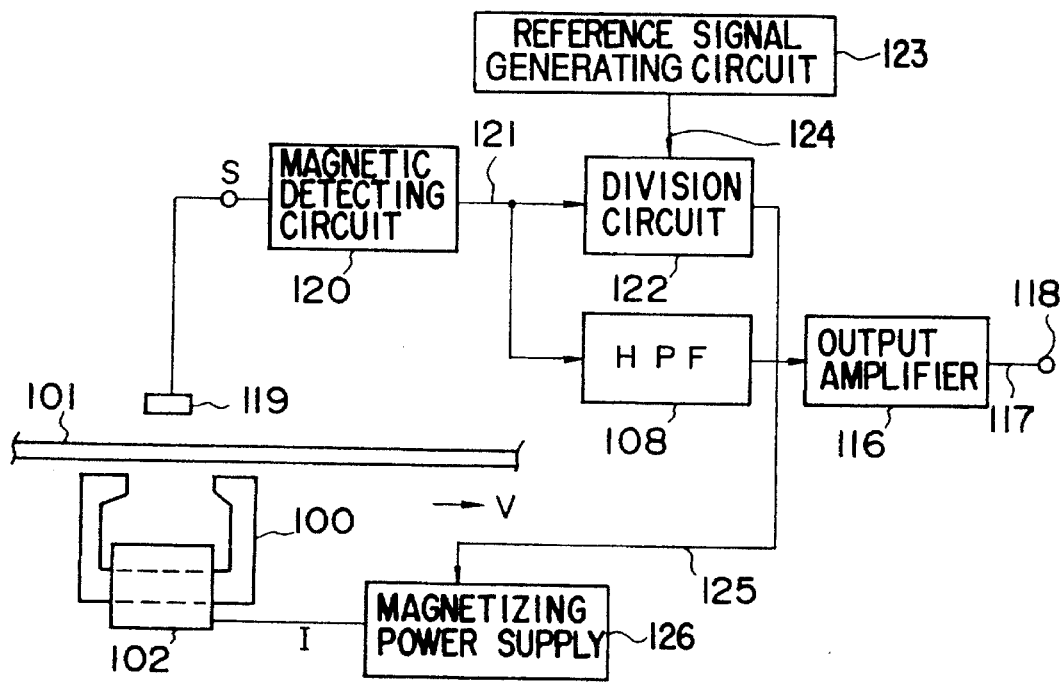
FIG. 26 is a block diagram illustrating a magnetic detector according to another further embodiment of the present invention.

FIG. 26 is a block diagram illustrating a magnetic detector according to another further embodiment of the present invention. The components identical to those of the embodiment shown in FIG. 25 are designated by the same reference numerals and will not be described in detail.

In this embodiment, the control signal 125 output from a division circuit 122 is input to the control terminal of a magnetizing power supply 126. The control signal 125 controls the exciting current I to be supplied from the magnetizing power supply 126 to a magnetizer 100.

As has been indicated, the level of the signal input to the division circuit 122 can be regarded as almost equal to the level of the low-frequency signal which corresponds to the intensity of a magnetic field. Thus, the exciting current I is thereby controlled such that the floating flux detected by a horizontal-type magnetic sensor 119 always remains at a constant value. As a result, the fluctuation of the magnetizing force on a thin steel strip 101, which has resulted from the changes in the moving speed, is compensated for, and the accuracy of detecting the size of the defect is always maintained at a substantially constant value.

Figure 27:
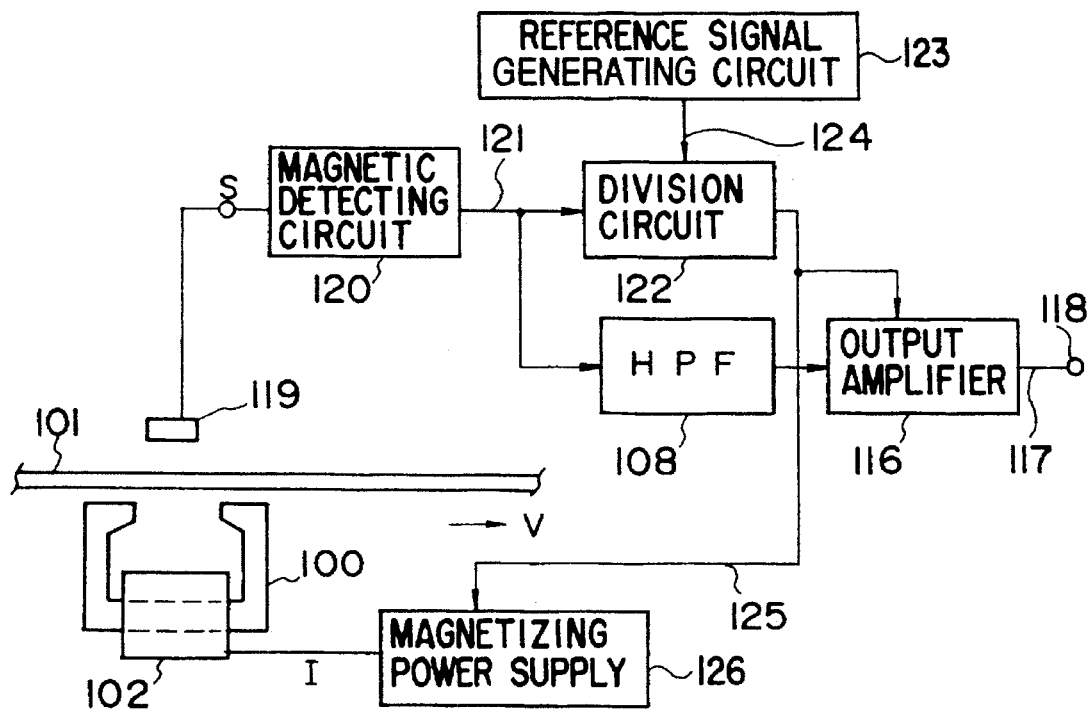
FIG. 27 is a block diagram showing a magnetic detector according to still another further embodiment of the invention.

FIG. 27 is a block diagram showing a magnetic detector according to still another further embodiment of the invention. The components identical to those of the embodiment shown in FIG. 26 are designated by the same reference numerals and will not be described in detail.

In this embodiment, the control signal 125 output from a division circuit 122 is input to the control terminal of a magnetizing power supply 126, and also to the control terminal of an output amplifier 116.

With the magnetic detector of this structure, the level of a defect signal 117 and that of the exciting current for a magnetizer 100 are corrected at the same time. The signal level and the current level change rapidly when the moving speed V of, for example, a thin steel strip 101 abruptly changes. The accuracy of detecting the size of a defect is therefore enhanced further.

Figure 28:
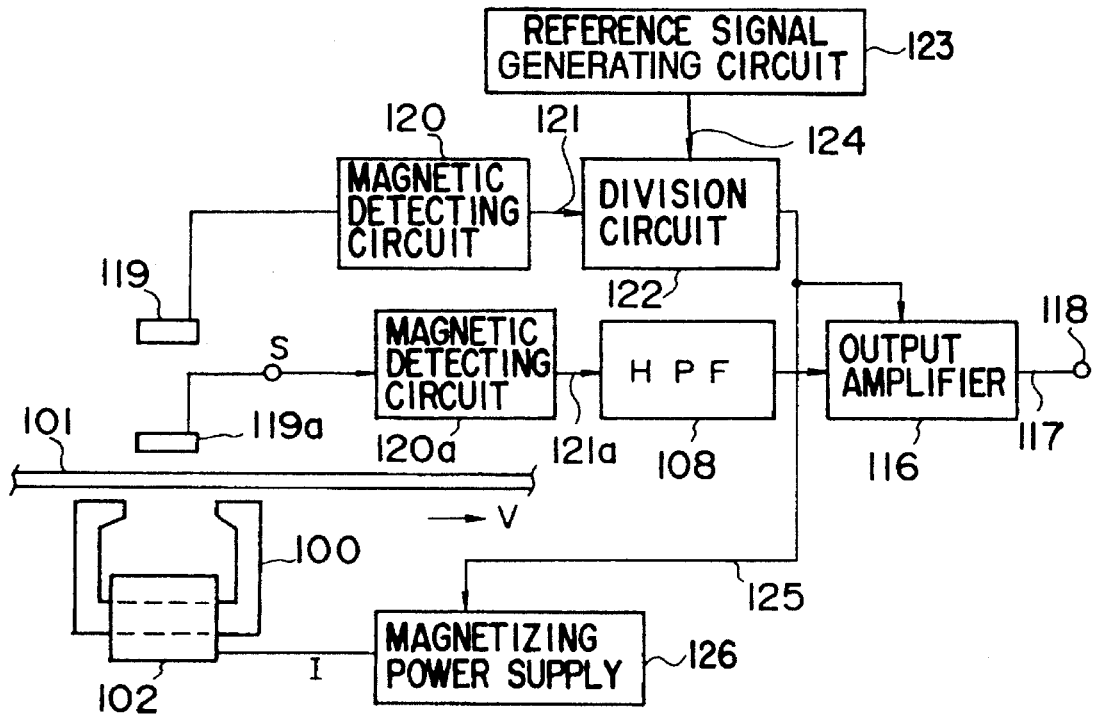
FIG. 28 is a block diagram showing a magnetic detector according to a further embodiment of this invention.

FIG. 28 is a block diagram showing a magnetic detector according to a further embodiment of this invention. The components identical to those of the embodiment shown in FIG. 23 are designated by the same reference numerals and will not be described in detail.

In this embodiment, a horizontal-type magnetic sensor 119a detects a leakage flux resulting from a defect in a thin steel strip 101. A magnetic detecting circuit 120a converts the signal output by the horizontal-type magnetic sensor 119a, into an output signal 121a which corresponds to the intensity of the magnetic flux. The output signal 121a is input to a high-pass filter 108. The high-pass filter 108 removes the low-frequency signal component contained in the output signal 121a. A signal output by the high-pass filter 108 is amplified by an output amplifier 116 and subsequently supplied, as a defect signal 117, to an output terminal 118.

The output signal 121 obtained from another horizontal-type magnetic sensor 119 is input to a division circuit 122. The division circuit 122 supplies a control signal 125 to a magnetizing power supply 126 and an output amplifier 116.

In the magnetic detector of this structure, as well, the horizontal-type magnetic sensor 119a detects defects, and the output signal of the other horizontal-type magnetic sensor 119 controls the exciting current and the amplification factor. Hence, this embodiment can attain advantages similar to those of the embodiment illustrated in FIG. 23.

Figure 29A:
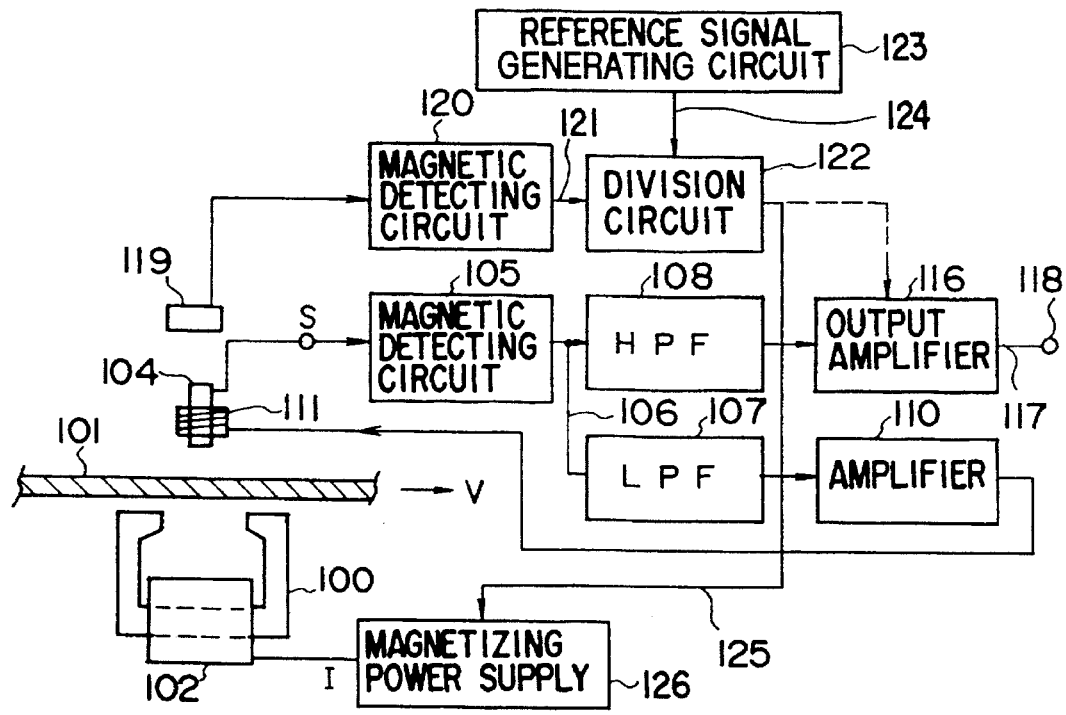
FIG. 29A is a block diagram showing a magnetic detector according to a further embodiment of this invention.

FIG. 29A is a block diagram showing a magnetic detector according to a further embodiment of this invention. The components identical to those of the embodiments shown in FIGS. 1 and 22 are designated by the same reference numerals and will not be described in detail.

In this embodiment, a vertical-type magnetic sensor 104 for detecting a leakage flux resulting from a defect, a compensating coil 111, and a horizontal-type magnetic sensor 119 for detecting a floating flux corresponding to the intensity of a magnetic field are arranged above a thin steel strip 101.

The signal output by the vertical-type magnetic sensor 104 is converted by a magnetic detecting circuit 105 into an output signal 106 which corresponds to a defect. The output signal 106 is input to a high-pass filter 108. The high-pass filter 108 removes the low-frequency signal component from the output signal 106. The signal output by the high-pass filter 108 is amplified by an output amplifier 116 and subsequently supplied, as a defect signal 117, to an output terminal 118. The low-frequency signal component contained in the output signal 106 is extracted by a low pass filter 107 and subsequently amplified by an amplifier 110. The low-frequency signal component, thus amplified, is supplied to the compensating coil 111.

Meanwhile, the signal output by the horizontal-type magnetic sensor 119 is converted by a magnetizing detecting circuit 120 into an output signal 121 which corresponds to the floating flux. The signal 121 is input to a division circuit 122. The division circuit 122 supplies a magnetizing power supply 126 with a control signal 125 which varies in accordance with the floating flux.

In this embodiment, the exciting current I for a magnetizer 100 changes in response to the changes in the magnetizing force on the thin steel strip 101, which have been caused by the changes of the moving speed V of the strip 101. The magnetizing force is thereby maintained always at a constant value. Further, the low-frequency signal component contained in the output signal 106 and resulting from the floating flux is canceled and reduced.

By virtue of the two independent control methods, thus performed, it is possible to maintain the accuracy of detecting the size of a defect, always at a high value.

Figure 29B:
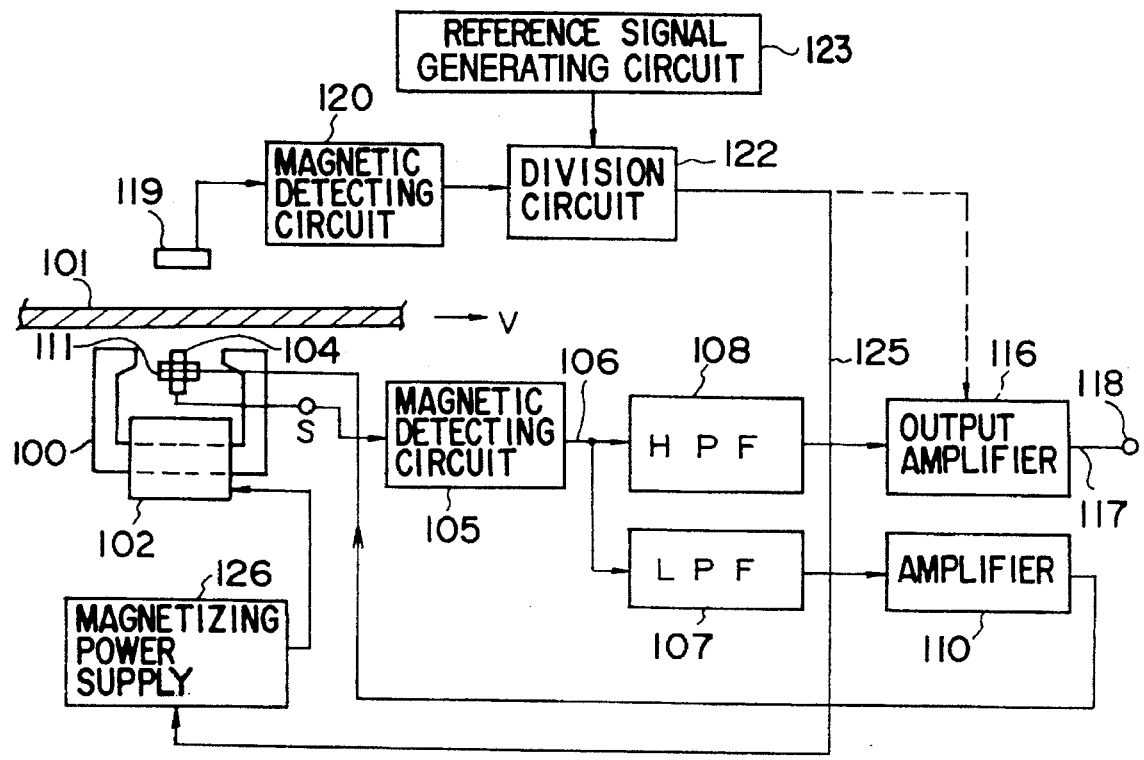
FIG. 29B is a block diagram showing a magnetic detector according to another embodiment of the present invention.

FIG. 29B is a block diagram showing a magnetic detector according to another embodiment of the present invention. The components identical to those of the embodiment shown in FIG. 29A are designated by the same reference numerals and will not be described in detail.

In this embodiment, a horizontal-type magnetic sensor 119 for detecting a floating flux corresponding to the intensity of a magnetic field is arranged above a thin steel strip 101, whereas a vertical-type magnetic sensor 104 for detecting a leakage flux resulting from a defect and a compensating coil 111 are located below the thin steel strip 101. The magnetic detector of this structure can attain advantages similar to those of the embodiment shown in FIG. 29A, too.

Figure 29C:
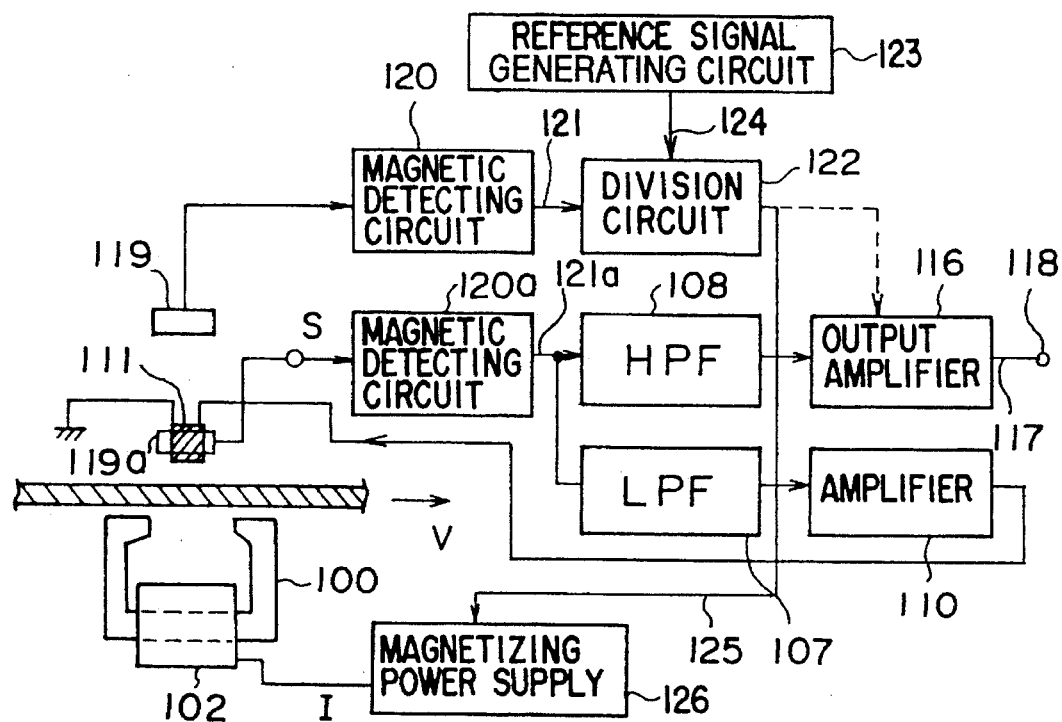
FIG. 29C is a block diagram showing a magnetic detector according to still another further embodiment of this invention.

FIG. 29C is a block diagram showing a magnetic detector according to still another further embodiment of this invention. The components identical to those of the embodiment shown in FIG. 29A are designated by the same reference numerals and will not be described in detail.

In the detector according to this embodiment, a leakage flux resulting from a defect in a thin steel strip 101 is detected by a horizontal-type magnetic sensor 119a. A compensating coil 111 is wound around the horizontal-type magnetic sensor 119a. The signal output by the horizontal-type magnetic sensor 119a is converted by a magnetic detecting circuit 120a into an output signal 121a which corresponds to the intensity of the flux. The output signal 121a is input to a high-pass filter 108 and a low-pass filter 107. The signal output by the high-pass filter 108 is amplified by an output amplifier 116 and output as a defect signal 117. The signal output by the low-pass filter 107 is amplified by an amplifier 110 and subsequently supplied to the compensating coil 111. A division circuit 122 supplies a control signal to a magnetizing power supply 126.

Since the amplification factor of the output amplifier 116 and the magnetizing current supplied by the magnetizing power supply 126 are controlled, this embodiment can attain advantages almost identical to those of the embodiment shown in FIG. 29A.

Figure 30:
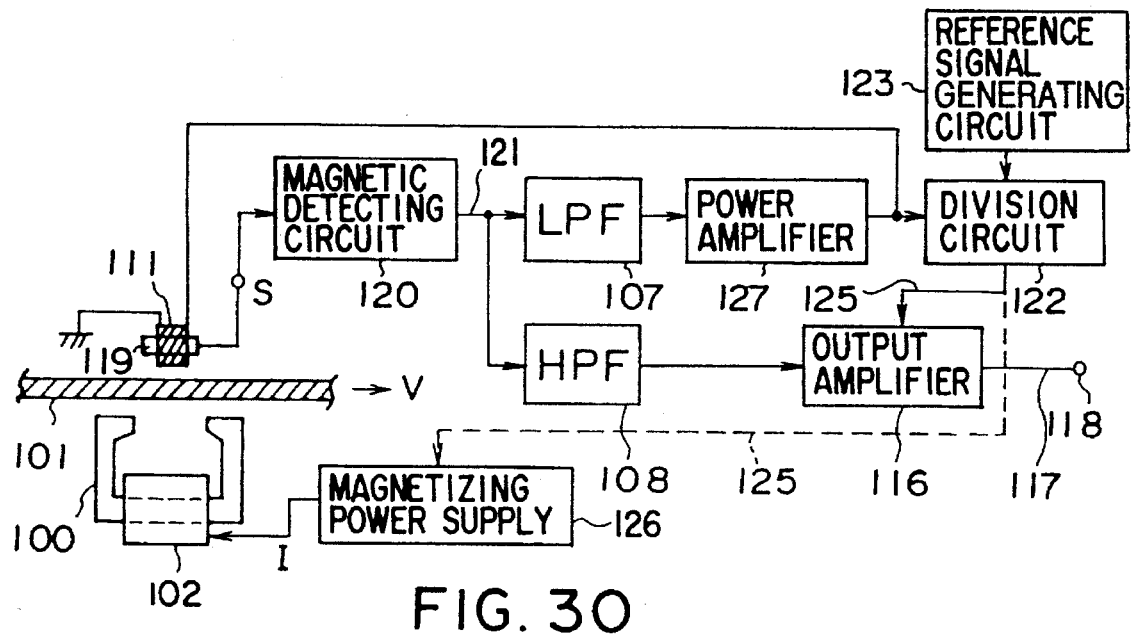
FIG. 30 is a block diagram illustrating a magnetic detector according to a different embodiment of this invention.

FIG. 30 is a block diagram illustrating a magnetic detector according to a different embodiment of this invention. The components identical to those of the embodiment shown in FIG. 28 are designated by the same reference numerals and will not be described in detail.

In the detector according to this embodiment, a horizontal-type magnetic sensor 119 and a compensating coil 111 wound around this magnetic sensor 119 are located above a thin steel strip 101. The signal output by the horizontal-type magnetic sensor 119 is converted by a magnetic detecting circuit 120 into an output signal 121 which corresponds to a magnetic flux crossing the horizontal-type magnetic sensor 119. The low-frequency signal component contained in the output signal 121 and corresponding to a floating flux is removed by means of a high-pass filter 108. The output signal, no longer containing the low-frequency signal component, is amplified by an output amplifier 116 and output from an output terminal 118 in the form of a defect signal 117.

The low-frequency signal component contained in the output signal 121 and corresponding to a floating flux is extracted by a low-pass filter 107 and subsequently amplified by a power amplifier 127. The low-frequency signal component, amplified by the power amplifier 127, is supplied to the compensating coil 111. Further, the low-frequency signal component, amplified by the power amplifier 127, is input to a division circuit 122. The control signal output from the division circuit 122 is supplied to the control terminal of the output amplifier 116 and that of a magnetizing power supply 126.

In the magnetic detector of this structure, the compensating coil 111 generates magnetic fluxes which cancel out the floating flux. The low-frequency signal component contained in the output signal 121 and resulting from the floating flux is reduced thereby. Hence, the S/N ratio of the output signal 121 increases. In response to the changes in the magnetizing force which have resulted from the changes in the moving speed V of the thin steel strip 101, the exciting current I for a magnetizer 100 varies, thereby controlling the magnetizing force always at a constant value. Also, the amplification factor of the output amplifier 116 changes in response to the changes in the magnetizing force on the steel strip 101. This embodiment can therefore attain advantages almost identical to those of the embodiment shown in FIG. 28.

FIG. 31 is a block diagram showing a magnetic detector according to a further embodiment of this invention. The components identical to those of the embodiments shown in FIGS. 7 and 29A are designated by the same reference numerals and will not be described in detail.

In this embodiment, a vertical-type magnetic type sensor is used to detect a leakage flux resulting from a defect and also changes in magnetizing force which have resulted from the changes in the moving speed of a thin steel strip.

More specifically, the defect signal e selected by a multiplexer circuit 30 is input via an output amplifier 116 to a display 31. The signal output by an amplifier 26 is input to a division circuit 122. The division circuit 122 divides the output signal by the reference signal 124 output from a reference signal generating circuit 123, generating a control signal 125, which is supplied to the magnetizing power supply 126 of a magnetizer 4 (100).

In the magnetic detector of this structure, a compensating coil 22 generates magnetic fluxes which extend in such a direction as to cancel out the floating flux. The low-frequency signal component contained in the output signal d of a vertical-type magnetic sensor 7a and resulting from the floating flux is reduced thereby. Hence, the S/N ratio of the output signal increases. When a magnetizing force changes due to a change in the moving speed of a thin steel strip 10 (101), the output signal of the amplifier 26 has its level changed. As a result of this, the control signal 125 output by the division circuit 122 varies, changing the exciting current I for the magnetizer 4 (100). The magnetizing force on the thin steel strip 10 (101) is thereby controlled always at a constant value. Hence, the embodiment can therefore attain advantages almost identical to those of the embodiments shown in FIGS. 29A, 29B, and 29C.

The output signal of the amplifier 26 is supplied to the division circuit 122 in the embodiment of FIG. 31. Instead, the output signal of a low-pass filter 33 may be supplied to the division circuit 122.

Moreover, as is indicated by dashed lines, the control signal output from the division circuit 122 may be supplied to the output amplifier 116, not to the magnetizing power supply 126. In this case, the level of the defect signal e supplied to the display 31 is controlled in accordance with the change of the magnetizing force on the thin steel strip 10 (101).

FIG. 32 is a block diagram showing a magnetic detector according to another embodiment of the present invention. The components identical to those of the embodiment shown in FIG. 31 are designated by the same reference numerals and will not be described in detail.

In this embodiment, too, a vertical-type magnetic sensor is used to detect a leakage flux resulting from a defect and also changes in magnetizing force which have resulted from the changes in the moving speed of a thin steel strip.

More specifically, an integration circuit 35 is connected between a low-pass filter 33 and an amplifier 26. The output signal of the amplifier 26 is input to a division circuit 122. The division circuit 122 divides the output signal by the reference signal 124 output from a reference signal generating circuit 123, generating a control signal 125, which is supplied to an output amplifier 116.

In the magnetic detector of this structure, as in the embodiment of FIG. 31, a compensating coil 22 serves to reduce the low-frequency signal component contained in the output signal d of a vertical-type magnetic sensor 7a and resulting from the floating flux is reduced thereby. Hence, the S/N ratio of the output signal d increases. When a magnetizing force changes due to a change in the moving speed of a thin steel strip 10 (101), the output signal of the amplifier 26 has its level changed, and the control signal 125 output by the division circuit 122 varies. As a result, the level of the defect signal e supplied to the display 31 is controlled in accordance with the change in the magnetizing force on the thin steel strip 10 (101). Hence, the embodiment can therefore attain advantages almost identical to those of the embodiment shown in FIG. 31.

The output signal of the amplifier 26 is supplied to the division circuit 122 in the embodiment of FIG. 32. Instead, the output signal of a low-pass filter 33 or the integration circuit 35 may be supplied to the division circuit 122.

Moreover, as is indicated by dashed lines, the control signal output from the division circuit 122 may be supplied to a magnetizing power supply 126, not to the output amplifier 116. In this case, the magnetizing current I supplied from the magnetizing power supply 126 to a magnetizer 10 (100) changes such that the magnetizing force on the thin steel strip 10 (100) remains constant.

The inventors used the detectors according to the embodiments shown in FIGS. 31 and 32, thus performing flaw detection on a thin steel strip 10 with a standard defect having a diameter of 0.2 mm. The moving speed of the strip 10 was changed from 0 to 1200 m/min. The flaw detection was conducted under two different conditions. In the first condition, the switch 25 was closed, thus operating the compensating coil 22. In the second condition, the switch 25 was opened, thus not operating the compensating coil 22. The results are shown in FIG. 24.

From these results it can be understood that no substantial difference exists between the characteristic of the detectors of FIGS. 31 and 32, wherein only one type of a magnetic sensor, i.e., a vertical-type magnetic sensor, and the characteristic of the detectors of FIGS. 21 and 22, with only two types of magnetic sensors, i.e., a vertical-type magnetic sensor 104 and a horizontal-type magnetic sensor 119.

This phenomenon may be explained as follows.

As is shown in FIG. 24, too, in the embodiment of FIG. 1, in which feedback is made to the compensating coil only, the output (relative value) of the magnetic sensor decreases along a curve. This decrease is at most 5% when the moving speed V is increased to 1200 m/min. Said curve therefore looks almost like a straight line. This phenomenon is equivalent to the case where the vertical components of a magnetic field vary linearly with the moving speed. Thus, if the current from the magnetizing power supply or the amplification factor of the output amplifier is controlled to compensate for the decrease in the actual magnetizing force on the thin steel strip, a horizontal-type magnetic sensor need not be used to detect the horizontal component proportional to the speed V. Rather, to achieve the object, it suffices to use the output of the vertical-type magnetic sensor to control the current from the magnetizing power supply or the amplification factor of the output amplifier.

Needless to say, the accuracy of detecting defects will be enhanced if a horizontal-type magnetic sensor is used to detect a decrease in the magnetizing force on the thin steel strip.

Figure 33:
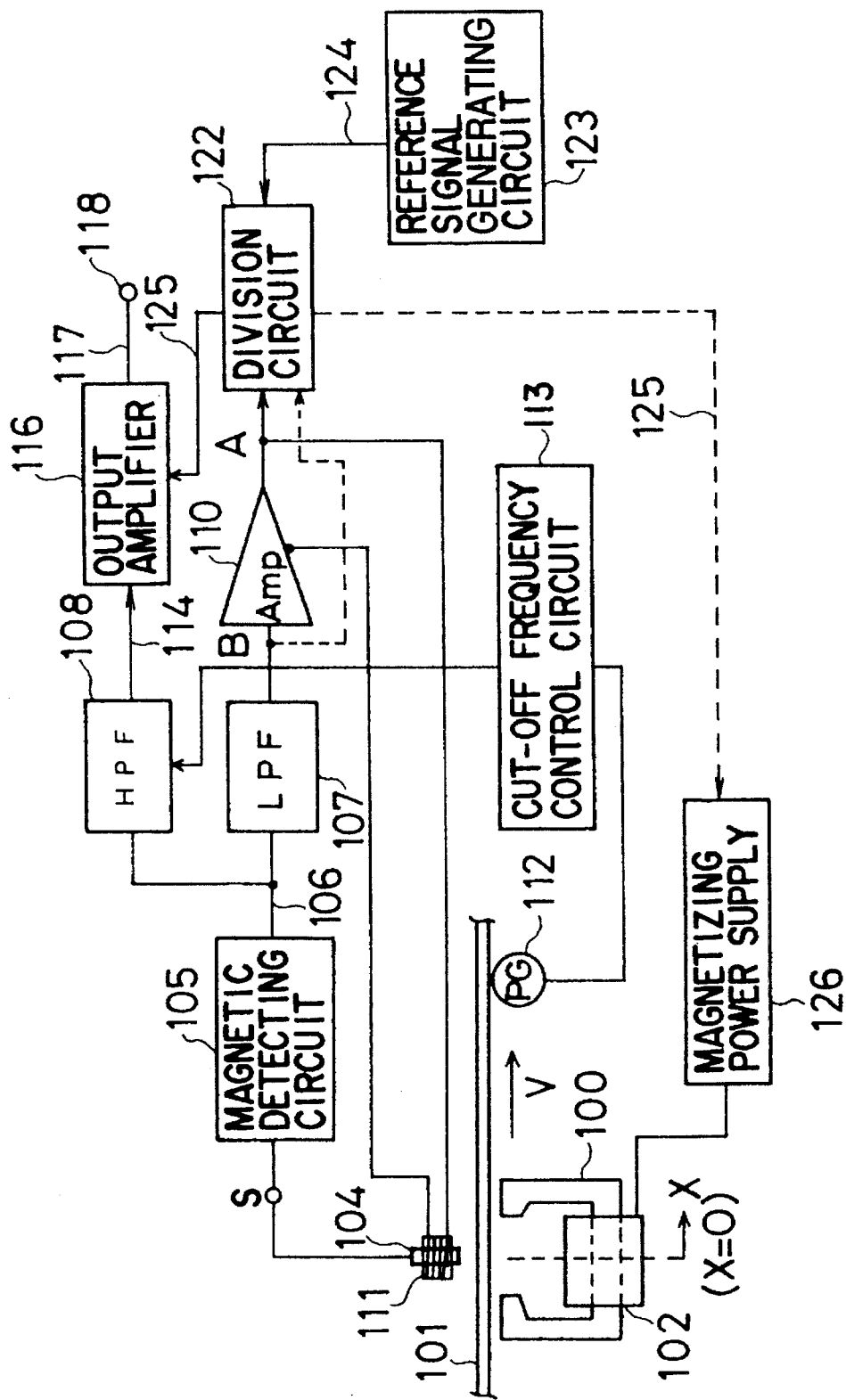
FIG. 33 is a block diagram showing a magnetic detector according to still another embodiment of this invention.

FIG. 33 is a block diagram showing a magnetic detector according to still another embodiment of this invention. The components identical to those of the embodiments shown in FIGS. 1 and 31 are designated by the same reference numerals and will not be described in detail.

The detector according to this embodiment is identical to the detector of FIG. 1, except that a division circuit 122, a reference signal generating circuit 123, and an output amplifier 116—all shown in FIG. 31—are used as additional components. The division circuit 122 divides the signal output by an amplifier 110 or a low-pass filter 107 by the reference signal 124 output from the reference signal generating circuit 123, producing a control signal 125, which is supplied to the output amplifier 116 or a magnetizing power supply 126.

Also in the magnetic detector of this structure, a floating flux component and a change of the magnetizing force can be removed. Hence, this embodiment can attain advantages almost identical to those of the embodiment shown in FIG. 31.

Figure 34:
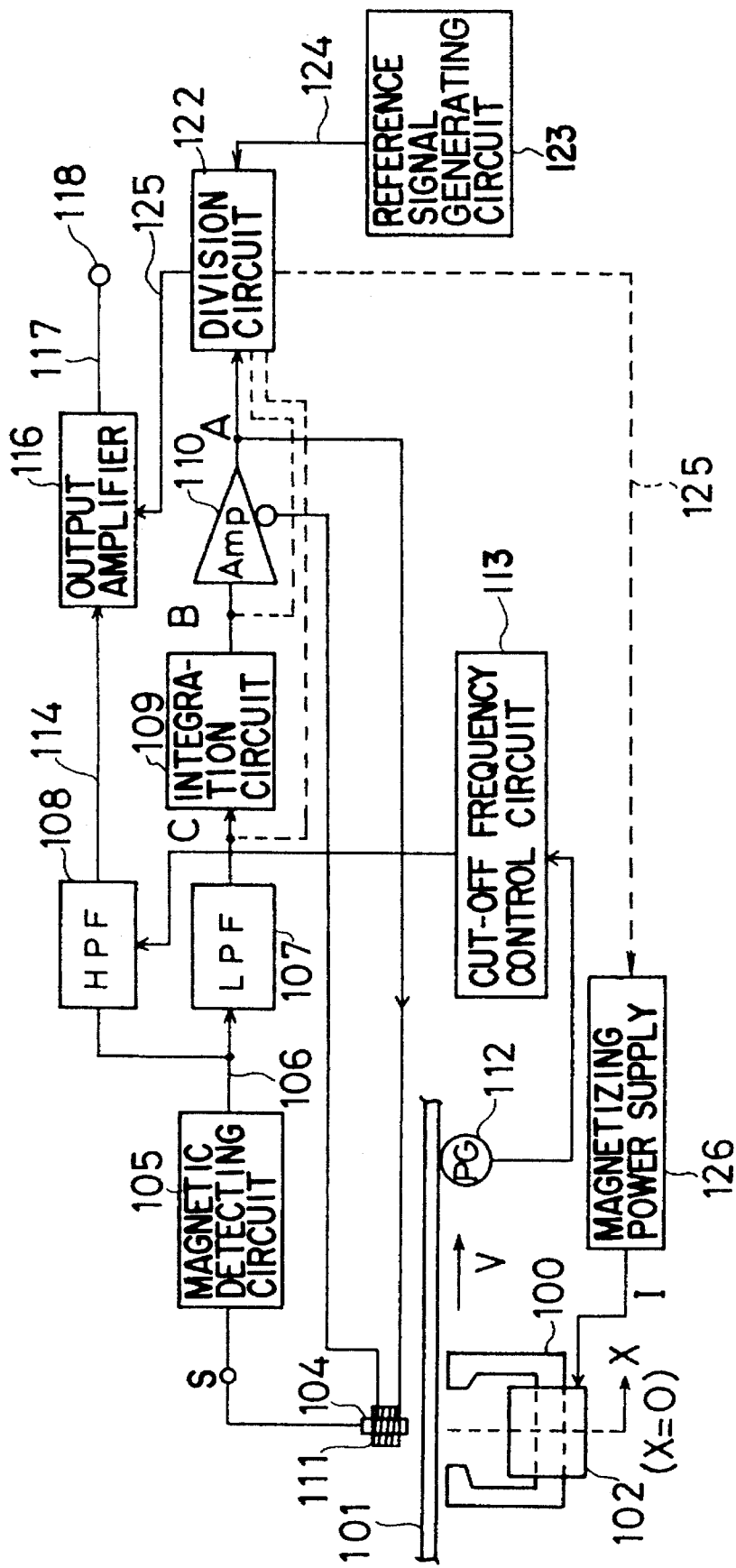
FIG. 34 is a block diagram showing a magnetic detector according to an embodiment of this invention.

FIG. 34 is a block diagram showing a magnetic detector according to an embodiment of this invention. The components identical to those of the embodiments shown in FIGS. 15 and 32 are designated by the same reference numerals and will not be described in detail.

The detector according to this embodiment is identical to the detector of FIG. 15, except that a division circuit 122, a reference signal generating circuit 123, and an output amplifier 116—all shown in FIG. 32—are used as additional components. The division circuit 122 divides the signal output by an amplifier 110, an LPF 107, or an integration circuit 109, by the reference signal 124 output from the reference signal generating circuit 123, producing a control signal 125, which is supplied to the output amplifier 116 or a magnetizing power supply 126.

Also in the magnetic detector of this structure, a floating flux component and a change of the magnetizing force can be removed. Hence, this embodiment can attain advantages almost identical to those of the embodiment shown in FIG. 32.

The present invention is not limited to each embodiment described above. As has been indicated, the high-pass filter 108 used in the embodiment of FIG. 1 can be replaced by a band-pass filter, whose pass-frequency band is broad. Nonetheless, the high-pass filter 108 used in any other embodiment can be replaced by a band-pass filter, as in the embodiment of FIG. 1.

Figure 35:
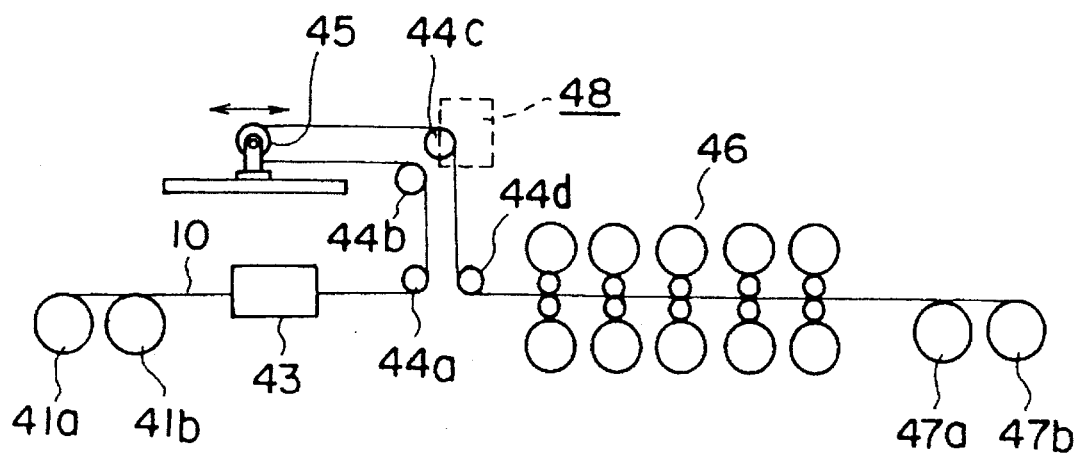
FIG. 35 is a schematic representation of a rolling line installed in an iron foundry.

FIG. 35 is a schematic representation of a rolling line installed in an iron foundry and incorporating a magnetic detector according to still another embodiment of the present invention.

Thin steel strips 10 are alternately fed from supply reels 41a and 41b. Each of the strips 10 passes through a welding apparatus 43. The welding apparatus 43 welds the strip to the immediately preceding one. The thin steel strip 10 is then turned by 180° by means of rolls 44a and 44b. It is further turned by 180° by means of looper roll 45, and further turned by 90° by means or rolls 44c and 44d, respectively. Then, the thin steel strips 10 are subjected to a rolling step 46 performed by a plurality of rolls and are alternately taken up by take-up reels 47a and 47b. The looper roll 45 can be moved back and forth as is indicated by the arrows shown in the figure. It is moved to the right while the welding apparatus 43 is welding the strips, so that the thin steel strips 10 may be fed forward in the rolling step 46.

In the rolling line, the magnetic detector unit 48 of this invention is incorporated in the roll 44c which turns the thin steel strip 10 by 90°, feeding the strip downwards.

Figure 36:
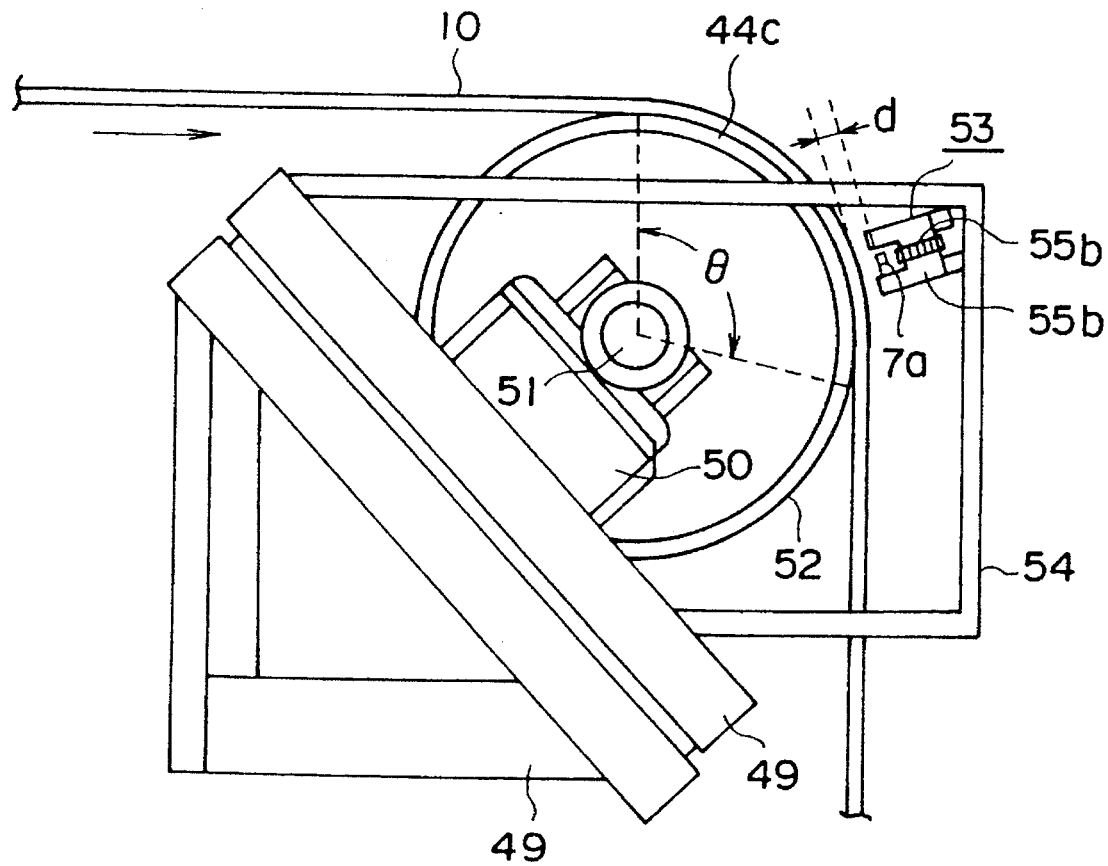
FIG. 36 is a side view schematically showing a magnetic detector used in the rolling line.

FIG. 36 is a side view schematically showing the magnetic detector unit 48. A shaft 51 is rotatably supported by a bracket 50 secured to a frame 49 which is fixed to the base of the building. The roll 44c is mounted on the shaft 51. The thin steel strip 10 fed from the left at a constant speed is supplied downwards, contacting about ¼ of the outer circumferential surface 52 of the roll 44c. The angle of contact of the strip 10, with respect to the roll 44c, is approximately 90°.

A support frame 54 is fastened to the frame 49 and supports the magnetic detector 53 at a predetermined position. The magnetic detector 53 is attached to the support frame 54 such that it opposes that portion of the thin steel strip 10 which contacts the outer circumferential surface 52 of the roll 44c, which surface is made of non-magnetic material.

The spacing d changes least, due to the vibration or warping of the thin steel strip 10, at the middle part of that portion of the strip 10 which contacts the roll 44c. In the embodiment shown in FIG. 36, however, the magnetic detector 53 is located, facing the lower end of that portion of the strip which contacts the roll 44c, due to the limited installation space, the position of the support frame 54, and the like. The fluctuation of the spacing, which takes place at this position, is far less than at the position where the strip 10 does not contact the roll 44c at all or than in the case where an extremely short portion of the strip 10 contacts the roll 44c. A sufficiently high S/N ratio can be secured at this position, too. In particular, it suffices to locate the magnetic detector 53, making it oppose that part of the thin steel strip 10 which contacts the roll 44c, in order to detect the welded portion of the thin steel strip 10.

Figure 37:
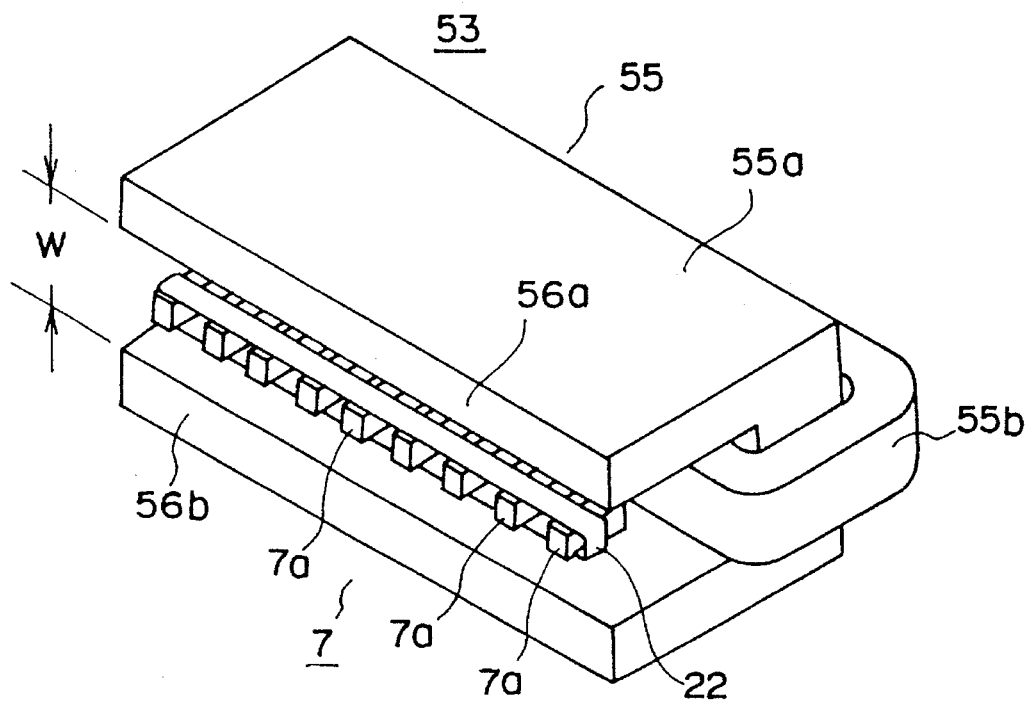
FIG. 37 is a perspective view schematically showing the magnetic sensor unit of the magnetic detector.

As is shown in FIG. 37, the magnetic detector 53 comprises, for example, a magnetizer 55 and a group 7 of magnetic sensors. The magnetizer 55 is constituted by a magnetizing core 55a having a substantially U-shaped cross section, and a magnetizing coil 55b wound around the core 55a. The group 7 consists of a plurality of magnetic sensors 7a which are arranged between a pair of magnetic poles 56a and 56b. A compensating coil 22 is wound, surrounding the magnetic-sensor group 7. The magnetizing core 55a has a width greater than that of the thin steel strip 10. The magnetic sensors 7a are arranged at predetermined intervals, over a distance which is longer than the width of the thin steel strip 10. The tip of each magnetic sensor 7a is placed in the same plane as the tips of the magnetic poles 56a and 56b. Each magnetic sensor 7a opposes the running strip 10, spaced apart therefrom for a narrow gap (i.e., distance d), as is illustrated in FIG. 36.

Each of the magnetic sensors 7a is of the saturable type which has been described. To be more specific, each magnetic sensor 7a comprises a core having a section of 0.1 mm×2.0 mm and a detecting coil wound around this core. In the embodiment, the magnetic sensors 7a are located at intervals of 10 mm. As a result, the detector has a sensitivity which is uniform in the width direction of the thin steel strip 10.

Figure 38:
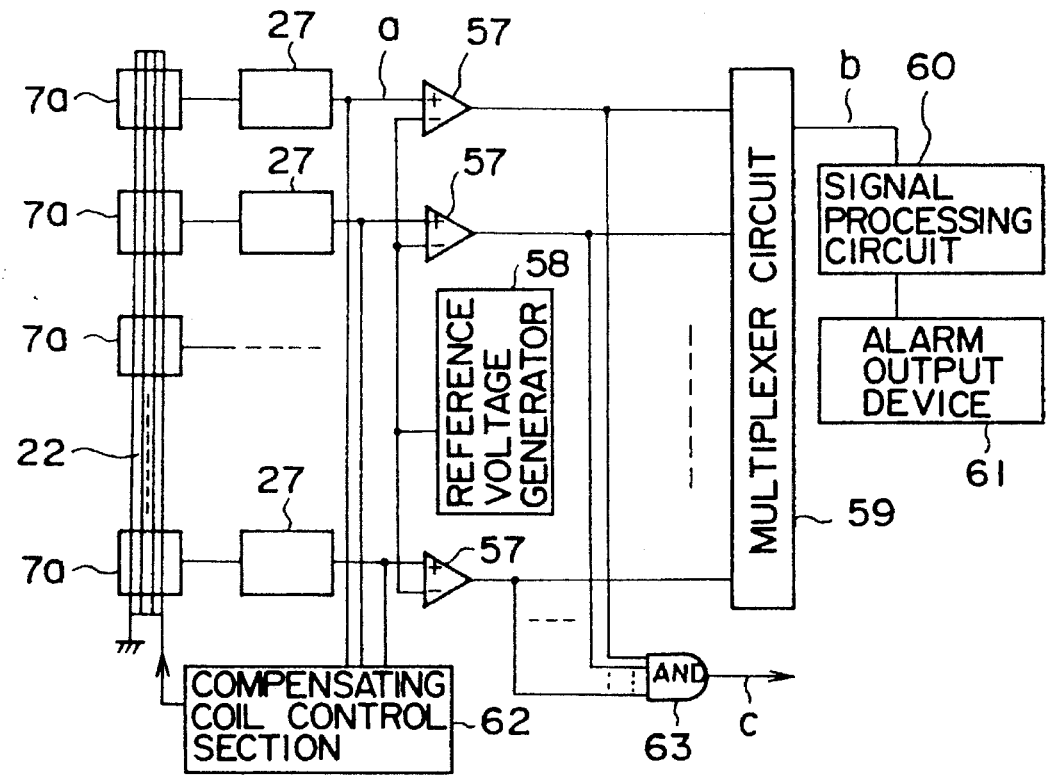
FIG. 38 is a block diagram showing the electrical structure of the sensor unit.

FIG. 38 is a block diagram showing the electrical structure of the magnetic sensor unit 48. The signal output by each magnetic sensor 7a is input to the corresponding one of magnetic detecting circuits 27. The circuit 27 converts the signal into a signal which corresponds to the intensity of a magnetic flux crossing the magnetic sensor 7a. The signal output by each magnetic detecting circuit 27 is input to the (+) input terminal of the corresponding one of comparators 57. The (−) input terminal of the comparator 57 receives a threshold voltage applied from a reference voltage generator 58. Each comparator 57 outputs a defect signal at the high (H) level when the output signal a of the magnetic detecting circuit 27 is higher than the threshold voltage. Each comparator 57 outputs a normal signal at the low (L) level when the output signal a is lower than the threshold voltage.

The defect signals or the normal signals output by the comparators 57 are converted into a time-divided multiplex signal b by means of a multiplexer circuit 59. The signal b is input to a signal processing circuit 60. The signal processing circuit 60 demodulates the time-divided multiplex signal b back into the defect signals or normal signals corresponding to the outputs of the magnetic sensors 7a. These signals are displayed by, for example, a CRT display or are converted into alarms by means of an alarm output device 61.

The output signal a of each magnetic sensor 7a is input to a compensating coil control section 62. The compensating coil control section 62 incorporates an equalizing circuit 32, a low-pass filter 33, an integration circuit 35, and an amplifier 26—all being of the types shown in FIG. 16. The compensating coil control section 62 supplies an exciting current to the compensating coil 22 so that each output signal a may contain no low-frequency signal component resulting from a floating flux.

The defect signal or normal signal output from each comparator 57 is input to an AND gate 63. The AND gate 63 outputs a signal only when all signals are defect signals at the high (H) level. In other words, defects have been detected at the positions where the all magnetic sensors 7a are arranged in the widthwise direction of the thin steel strip 10. Therefore, it is determined that the welded portion formed by the welding apparatus 43 shown in FIG. 35 has been detected. Thus, the AND gate 63 outputs a welded portion signal.

The magnetic detector shown in FIG. 38 reliably detects defects having a size greater than the reference value and existing at intervals in the widthwise direction of a thin steel strip 10 running in the rolling line. Not only the defects, but also the welded portion is detected when it reaches the magnetic sensors and a welded portion signal is generated.

Figure 39:
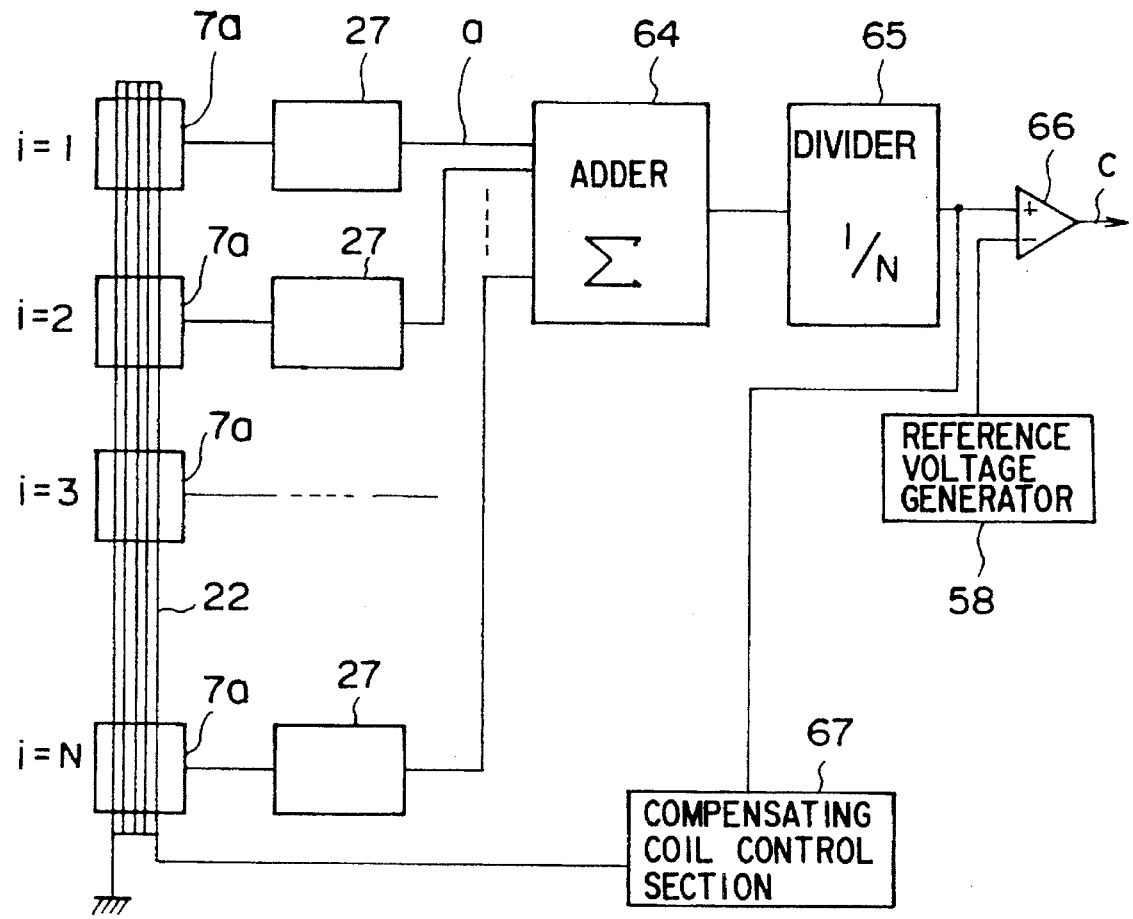
FIG. 39 is a block diagram showing the electrical structure of a magnetic detector according to another embodiment of the present invention.

FIG. 39 is a block diagram showing the electrical structure of a magnetic detector according to another embodiment of the present invention. This detector is designed to detect welded portions only.

The signals output by N magnetic sensors 7a (i=1 to N) are converted by magnetic detecting circuits 27 into output signals a which correspond to the intensities of the magnetic fluxes crossing the magnetic sensors 7a, respectively. Thereafter, the N output signals a are added together by means of an adder 64. The signal obtained by adding these signals a is divided by N in a divider 65. In other words, the divider 65 calculates an average value for each output signal a. The signal representing the average value is compared by a comparator 66 with a threshold voltage applied from a reference voltage generator 58. The comparator 66 outputs a welded portion signal c only when the average-value signal is greater than the threshold voltage. The average-value signal output from the divider 65 is input to a compensating coil control section 67. The compensating coil control section 67 performs the same function as the compensating coil control section 62 shown in FIG. 38; it supplies an exciting current to a compensating coil 22 so that each output signal a may contain no low-frequency signal component resulting from a floating flux.

Next, a test device measures the output signal a of each magnetic sensor 7a, while the ratio ($\alpha/\beta$) is being varied, where $\alpha$ is the contact angle defined by the center of the roll 44c and the edges of that portion of the thin steel strip 10 which contacts the outer circumferential surface 52 of the roll 44c, and $\beta$ is the angle defined by the center of the roll 44c and the ends of a line which represented the inter-polar distance w projected on the steel strip 10. The S/N ratio of each output signal a was thereby obtained.

Figure 40:
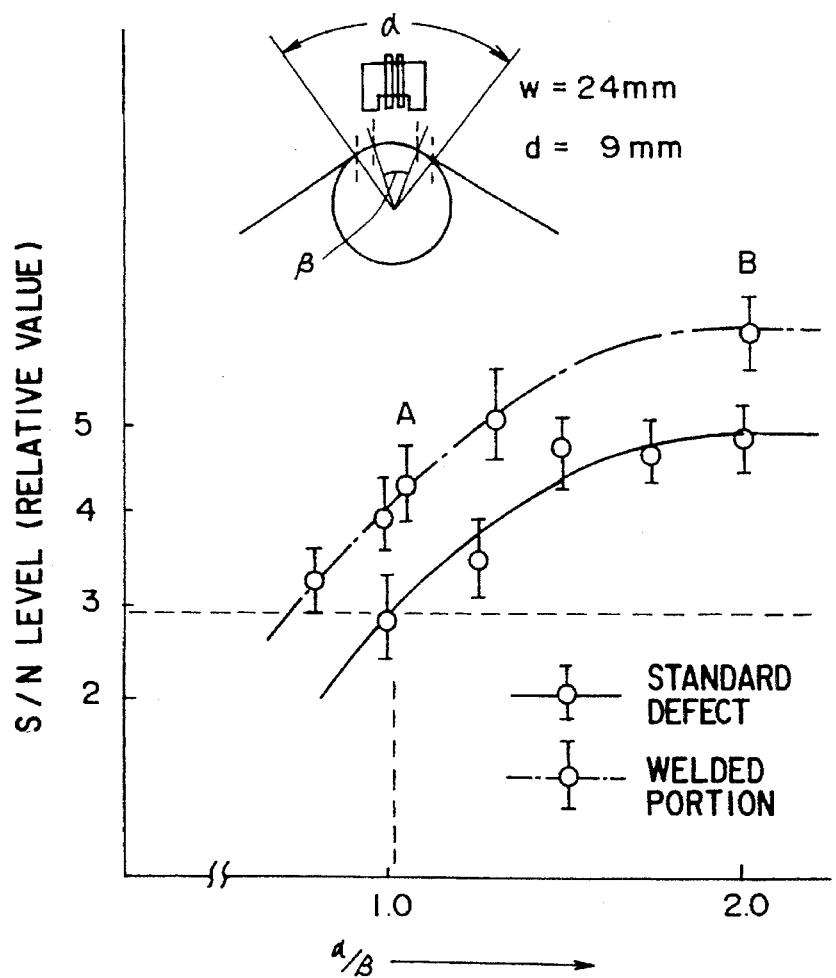
FIG. 40 is a diagram representing the relation between an angle ($\alpha/\beta$) ratio (the ratio of a contact length to an inter-pole distance) and a signal/noise (S/N) ratio, explaining the advantages of the detector.

The S/N ratio for each ratio ($\alpha/\beta$) is indicated by a one-dot, one-dash line in FIG. 40. The S/N ratio shown is one statistically processed and represented in relative value, along with a standard deviation. The inter-polar distance w is of a fixed value of 24 mm. The angle $\beta$ is therefore fixed. Hence, the contact angle $\alpha$ is varied, thereby changing the ratio ($\alpha/\beta$). A thin steel strip 10 having a standard defect (a round hole of 0.8 mm in diameter) is used as a test piece. The distance d between each magnetic sensor 7a and the thin steel strip 10 (i.e., lift-off) is 9 mm.

The solid line indicates the results of measurement of a thin steel strip 10 which is different from the test piece having the standard defect in that it has a welded portion extending over its entire width.

Assuming that an S/N ratio equal to or greater than 3 is a practical level, the ratio ($\beta/\beta$) needs to be 1.0 or more in practical defect detection. Since the welded portion can be regarded as a defect much larger than the standard defect, it can be reliably detected when the S/N ratio is 0.8 or more. Thus, it is required that the inter-polar angle $\beta$ (distance w) be less than the contact angle $\alpha$ of the strip 10 with respect to the roll 44c.

Figure 41:
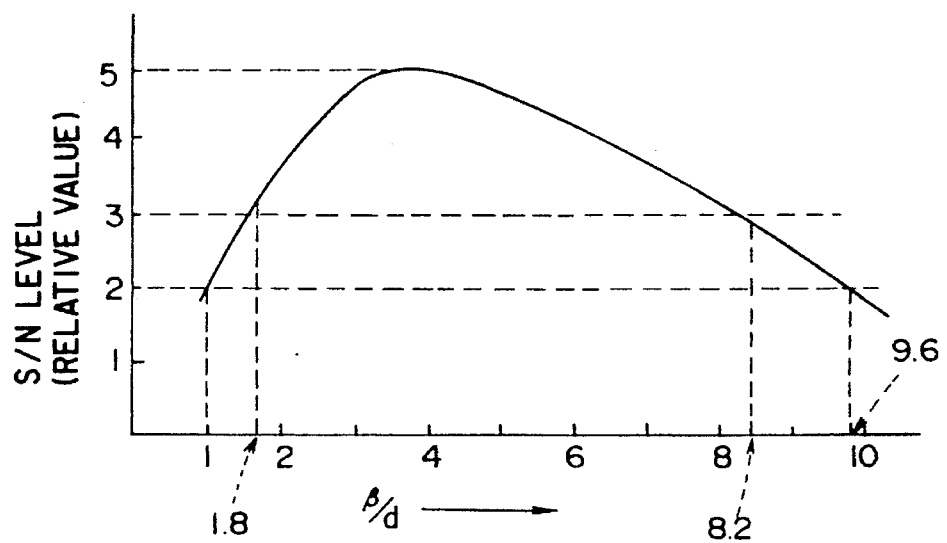
FIG. 41 is a diagram illustrating the relation between a ratio of an inter-pole distance (given in terms of angle $\beta$) to a lift off d ($\beta/d$) and a signal/noise (S/N) ratio, explaining the advantages of the detector.

Next, the S/N ratio of the signal a output by each magnetic sensor 7a was measured while the ratio ($\alpha/\beta$) of the inter-polar angle $\beta$ (distance w) to the spacing d was varied and while the distance d between the sensor 7a and the thin steel strip 10 was gradually changed. In FIG. 41, the ratio ($\beta/d$) of the inter-polar angle $\beta$ (distance w) to the spacing d is plotted on the abscissa and the statistical relative value of the S/N ratio is plotted on the ordinate. The inter-polar angle $\beta$ (distance w) is fixed (w=20 mm), and the spacing was changed to vary the ratio ($\beta/d$). Also, the condition that the ratio ($\alpha/\beta$) shown in FIG. 41 be 1 or more was satisfied.

As is shown in FIG. 41, a good S/N ratio (relative value) of 3 or more was acquired when the ratio ($\beta/d$) between the inter-polar angle $\beta$ (distance w) and the distance d ranged from 1.8 to 8.2.

To perform on-line flaw detection, it is desirable that the S/N ratio be 3 or more, as has been described. In order to detect, for example, a welded portion, however, an S/N ratio of 2 or more is sufficient in practice. In this case, the ratio ($\beta/d$) can be in a broader range of 1.0 to 9.6.

Figure 42:
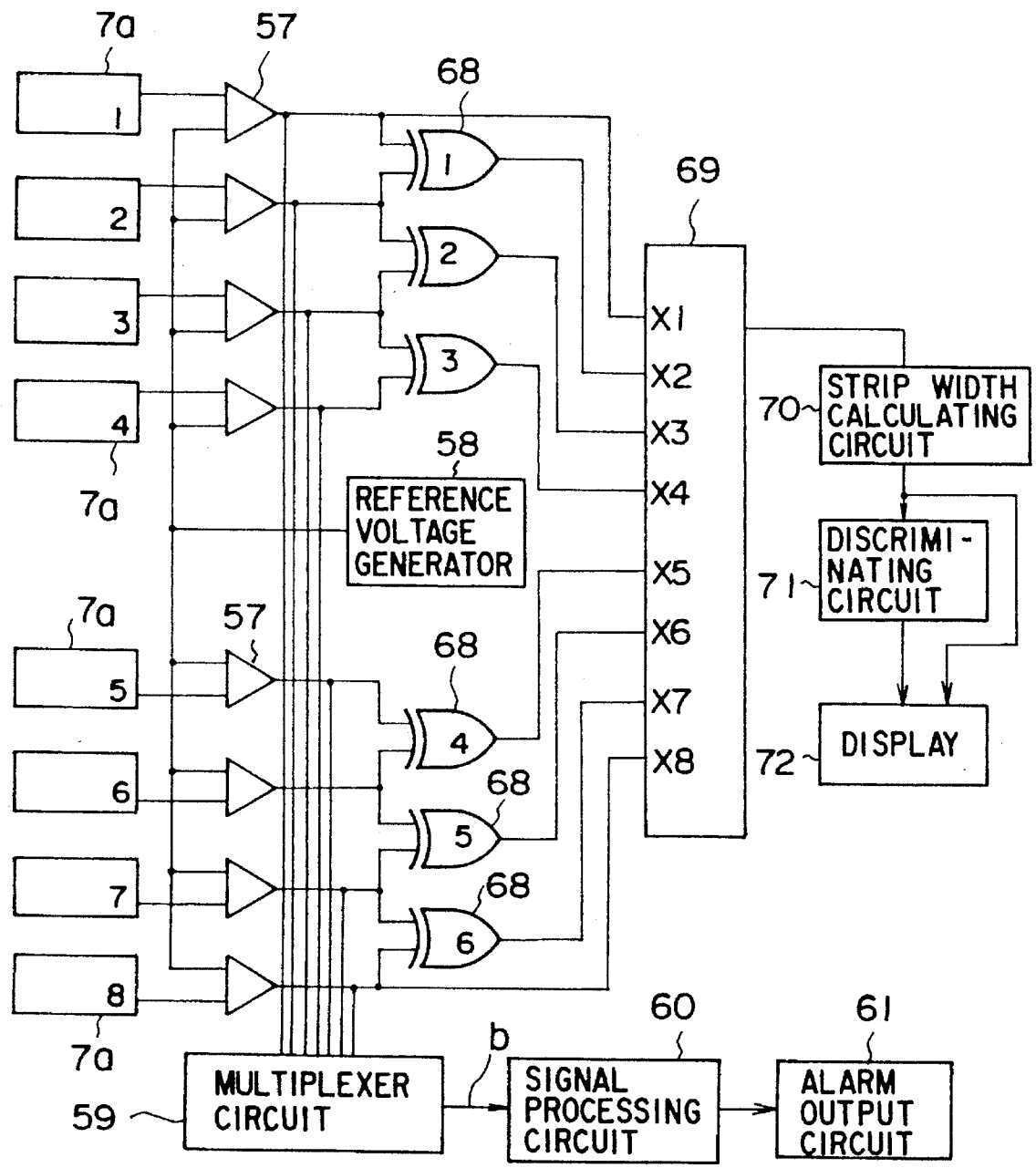
FIG. 42 is a block diagram showing the electrical structure of a magnetic detector according to still another embodiment of the invention.

FIG. 42 is a block diagram showing the electrical structure of a magnetic detector according to still another embodiment of the invention. The components identical to those of the embodiments shown in FIG. 38 are designated at the same reference numerals. The detector of this embodiment can detect not only defects but also the width A of a thin steel strip 10.

Eight magnetic sensors 7a are arranged in the widthwise direction of the thin steel strip 10. The signal output by each sensor 7a is input to the corresponding one of comparators 57, which compares the signal with the threshold voltage applied from a reference voltage generator 58. The signal is thereby converted into a binary signal, either a defect signal or a normal signal. The signals output by the comparators 57, each being either a defect signal or a normal signal, are converted into a time-divided multiplex signal b by means of a multiplexer circuit 59. The signal b is input to a signal processing circuit 60. The signal processing circuit 60 demodulates the time-division multiplex signal b back into the signals output from the magnetic sensors 7a, each being a defect signal or a normal signal. These signals are displayed by, for example, a CRT display or are converted into alarms by means of an alarm output circuit 61.

In FIG. 42, a compensating coil 22 and a compensating coil control section 67 are not illustrated.

To detect an ordinary defect existing in a thin steel strip 10, the threshold voltage applied from the reference voltage generator 58 is set at a value a little less than the level of a signal representing the standard defect. Hence, a leakage flux at a specific level is generated even if the thin steel strip 10 has no defects. However, if there is no thin steel strip 10, the leakage flux is far less intense than in the case where there is a thin steel strip 10, and the signal corresponding to the leakage flux is at a level which is substantially constant. Thus, the threshold voltage is set low, thereby to detect the presence or absence of a thin steel strip 10.

The signals output by any two adjacent comparators 57, each being either a defect signal or a normal signal, are input to an exclusive logic-sum gate 68. The signals output by the first and last comparators 57 and the signals output by the exclusive logic-sum gates 68 are input to the eight terminals X1 to X8 of an input circuit 69. The signals input to the terminals X1 to X8 are input to a strip width calculating circuit 70. The strip width calculating circuit 70 calculates the width A of the strip 10 from the values of the eight input signals. A discriminating circuit 71 determines whether or not the width A of the strip 10 falls within a tolerance range. A display 72 displays the result of this determination and the width A calculated.

The width A of the thin steel strip 10 is calculated in the following way. Assuming that any two adjacent magnetic sensors 7a are spaced apart by a distance B, the distance between the first and last sensors 7a and 7a shown in FIG. 38 is 7B. If the output signal of every magnetic sensor 7a is "0," there is no thin steel strip 10. If the signal is "1,"0 there is a thin steel strip 10. Hence, when the signal output by an exclusive logic-sum gate 68 is "1," it is determined that the edge of a thin steel strip 10 exists between the magnetic sensors 7a connected to the two comparators 57 which are connected to that exclusive logic-sum gate 68. The width A of the strip 10 can therefore be obtained by multiplying the distance B by the number of exclusive logic-sum gates 68 located between the two exclusive logic-sum gates 57 whose output signals are "1."

It is necessary to determine that the comparators 57 connected to the first and eighth magnetic sensors 7a output signals of "0." If one of these signals is "1," it is determined that the width A of the strip 10 is longer than the distance between the magnetic sensors 7a.

Thus, any defect in the thin steel strip 10 can be detected with high accuracy, and the width A of the strip 10 can be measured, if necessary.

Figure 43:
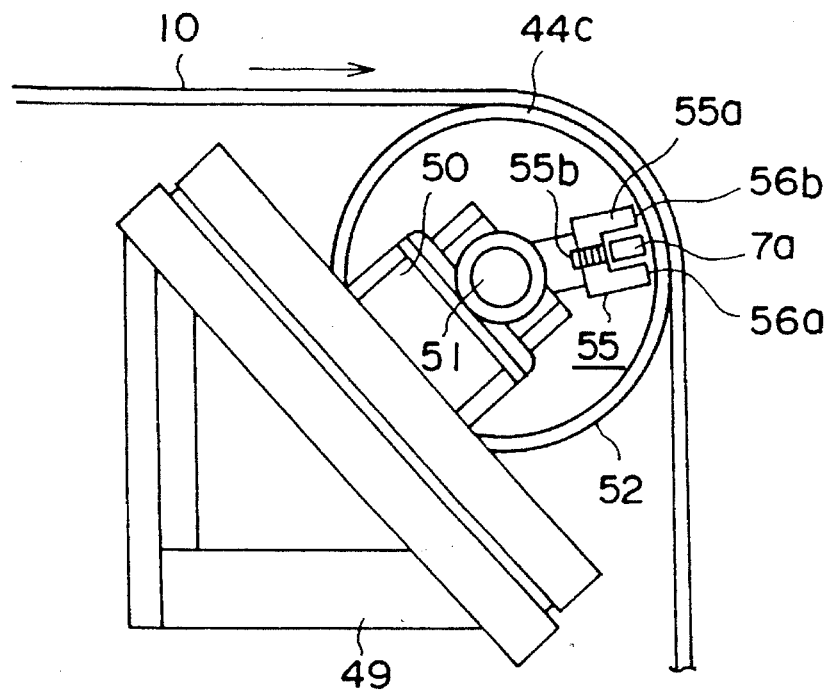
FIG. 43 is a side view schematically showing a magnetic detector according to an embodiment of the present invention.

FIG. 43 is a side view schematically showing a magnetic detector according to an embodiment of the present invention. The components identical to those of the embodiments shown in FIG. 36 are designated by the same reference numerals and will not be described in detail.

In this embodiment, a magnetizer 55 for magnetizing a thin steel strip 10 and magnetic sensors 7a for detecting leakage fluxes resulting from defects, if any, in the strip 10 are contained in a roll 44c. To be specific, the magnetic poles 56a and 56b of the magnetizer 55 are secured to a bracket 50 by a support member, such that the poles oppose the inner circumferential surface of the roll 44c and are spaced apart therefrom by a narrow gap. Therefore, the magnetizer 55 does not rotate, and only the roll 44c rotates. The magnetic sensors 7a are arranged between the magnetic poles 56a and 56b of the magnetizer 55.

Also in the magnetic detector of this structure, each magnetic sensor 7a can detect a leakage flux resulting from a defect in the thin steel strip 10 and extending through the wall of the roll 44c. Thus, this embodiment can attain advantages similar to those of the embodiments described above.

Further, the magnetic detector according to this embodiment can be installed in a limited space provided within a manufacturing line. This is because the magnetizer 55 and the magnetic sensors 7a are contained in the roll 44c.

Figure 44:
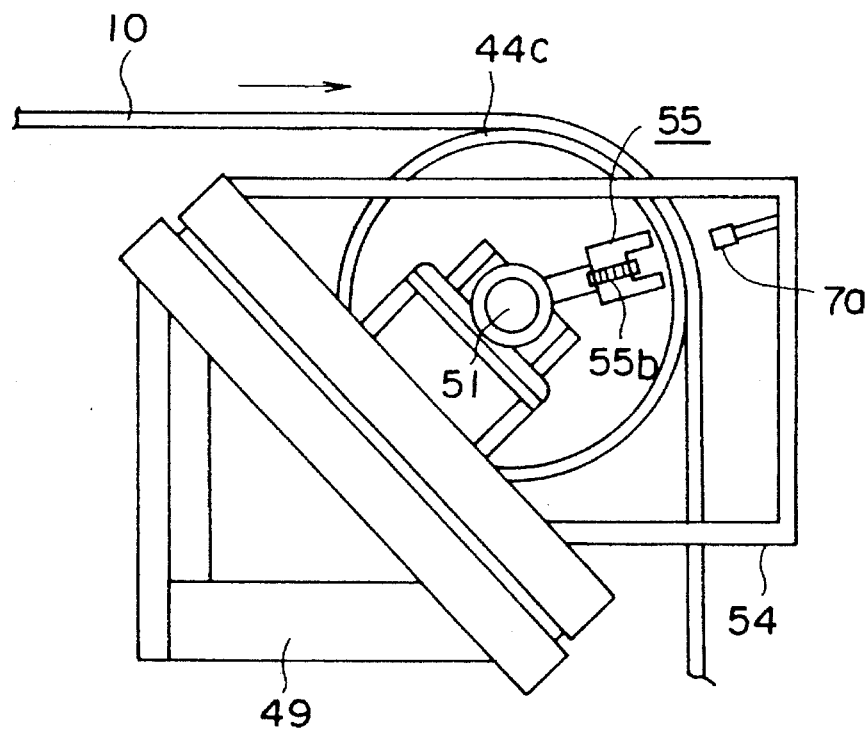
FIG. 44 is a side view schematically showing a magnetic detector according to another embodiment of this invention.

FIG. 44 is a side view schematically showing a magnetic detector according to another embodiment of this invention. In this embodiment, only a magnetizer 55 is contained in a roll 44c in the same manner as in the embodiment of FIG. 43. Each magnetic sensor 7a is fixed by a support frame 54, opposing the poles 56a and 56b of the magnetizer 55 contained in the roll 44c, with a thin steel strip 10 and the roll 44c interposed between the sensor 7a and the poles 56a and 56b. The magnetic detector thus structured, too, can attain advantages similar to those of the embodiments described above.

Figure 45:
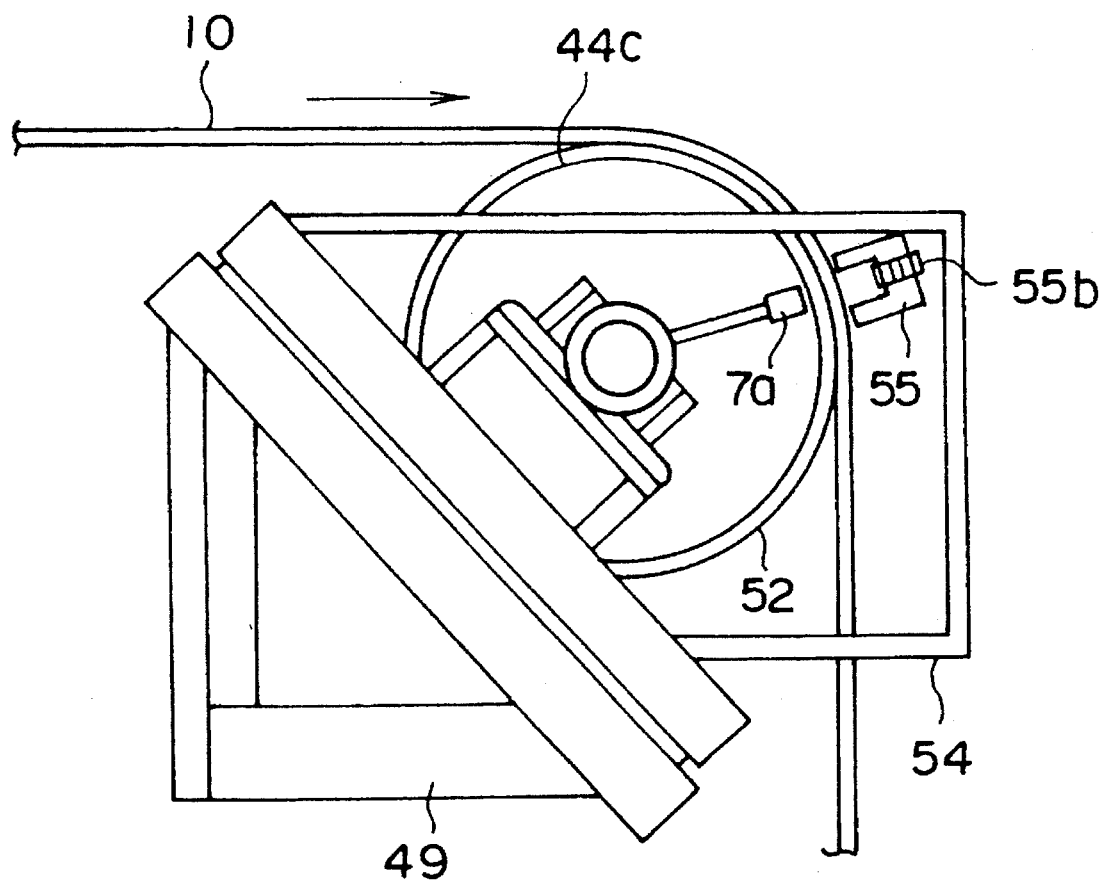
FIG. 45 is a side view schematically showing a magnetic detector according to still another embodiment of the present invention.

FIG. 45 is a side view schematically showing a magnetic detector according to still another embodiment of the present invention. This embodiment differs from that of FIG. 44 in that each magnetic sensor 7a is contained in a roll 44c, whereas a magnetizer 55 is located outside the roll 44c, secured to a support frame 54. This magnetic detector, thus structured, too, can attain advantages similar to those of the embodiments described above.

We claim:

1. A magnetic detector comprising:

means for generating a magnetic field;

a magnetic sensor for detecting a leakage flux resulting from a magnetically defective portion of an object moving in and relative to said magnetic field and for producing a signal corresponding thereto;

a low-pass filter for extracting a low-frequency signal component contained in said signal that is output by the magnetic sensor, said low-frequency signal component being indicative of a floating flux which crosses said magnetic sensor and which is a result of the object moving through said magnetic field;

an integrator for integrating the low-frequency signal component extracted by the low-pass filter;

an amplifier for amplifying the low-frequency signal component integrated by the integrator; and a compensating coil excited by the amplified low-frequency signal component output by the amplifier, for generating a magnetic flux which cancels out said floating flux crossing said magnetic sensor.

2. A magnetic detector according to claim 1, wherein said compensating coil is wound in surrounding relation to an outer circumferential surface of said magnetic sensor.

3. A magnetic detector comprising:

means for generating a magnetic field;

a first magnetic sensor for detecting a leakage flux resulting from a magnetically defective portion of an object moving in and relative to said magnetic field, said object having a surface;

a high-pass filter for extracting a signal resulting from the magnetically defective portion and which is contained in the signal that is output by said first magnetic sensor;

an output amplifier for amplifying a signal output by said high-pass filter and for outputting the amplified signal as a defect signal;

a second magnetic sensor located near said first magnetic sensor, for detecting a component of said magnetic field which is parallel to the surface of said object; and amplifier control means for controlling an amplification factor of said output amplifier in accordance with a signal output by said second magnetic sensor.

4. A magnetic detector comprising:

a magnetizer for generating a magnetic field;

a first magnetic sensor for detecting a leakage flux resulting from a magnetically defective portion of an object moving in and relative to said magnetic field generated by said magnetizer, said object having a surface;

said first magnetic sensor outputting a first output signal that is indicative of the leakage flux of the magnetically defective portion of the object;

a high-pass filter for extracting a signal resulting from the magnetically defective portion and which contained in the signal that is output by said first magnetic sensor;

a second magnetic sensor located near said first magnetic sensor, for detecting a component of said magnetic field which is parallel to the surface of said object;

an output amplifier coupled to receive a signal output by the high pass filter and for outputting an amplified signal as a defect signal; and magnetizer control means for controlling intensity of an said magnetic field generated by said magnetizer, in accordance with a signal output by the second magnetic sensor.

5. A magnetic detector comprising:

means for generating a magnetic field;

a first magnetic sensor for detecting a leakage flux resulting from a magnetically defective portion of an object moving in and relative to said magnetic field and for producing a signal corresponding thereto, said object having a surface;

a low-pass filter for extracting a low-frequency signal component contained in said signal output by the first magnetic sensor, said low-frequency signal component being indicative of a floating flux which crosses said first magnetic sensor and which is a result of the object moving through said magnetic field;

an amplifier for amplifying the low-frequency signal component extracted by said low-pass filter;

a compensating coil excited by the amplified low-frequency signal component output by the amplifier, for generating a magnetic flux which cancels out said floating flux crossing said first magnetic sensor, said compensating coil being located near said first magnetic sensor;

a high-pass filter for extracting a signal resulting from the magnetically defective portion and which is contained in the signal that is output by said first magnetic sensor;

an output amplifier for amplifying a signal output by said high-pass filter and for outputting the amplified signal as a defect signal;

a second magnetic sensor located near said first magnetic sensor, for detecting a component of said magnetic field which is parallel to the surface of said object; and amplifier control means for controlling an amplification factor of said output amplifier in accordance with a signal output by the second magnetic sensor.

6. A magnetic detector comprising:

a magnetic for generating a magnetic field;

a first magnetic sensor for detecting a leakage flux resulting from a magnetically defective portion of an object moving in and relative to said magnetic field generated by a magnetizer and for producing a signal corresponding thereto, said object having a surface;

a low-pass filter for extracting a low-frequency signal component contained in said signal output by the first magnetic sensor, said low-frequency signal component being indicative of a floating flux which crosses said first magnetic sensor and which is a result of the object moving through said magnetic field;

an amplifier for amplifying the low-frequency signal component extracted by said low-pass filter;

a compensating coil excited by the amplified low-frequency signal component output by the amplifier, for generating a magnetic flux which cancels out said floating flux crossing said first magnetic sensor, said compensating coil being located near said first magnetic sensor;

a high-past filter for extracting a signal resulting from the magnetically defective portion and which is contained in the signal output by said first magnetic sensor;

an output amplifier for amplifying a signal output by said high-pass filter and for outputting the amplified signal as a defect signal;

a second magnetic sensor located near said first magnetic sensor, for detecting a component of said magnetic field which is parallel to the surface of said object; and magnetizer control means for controlling the intensity of the magnetic field generated by said magnetizer, in accordance with a signal output by the second magnetic sensor.

7. A magnetic detector according to any one of claims 3, 4, 5 and 6, wherein said first magnetic sensor for detecting said leakage flux is oriented to detect a component of said leakage flux which is orthogonal to the surface of said object.

8. A magnetic detector according to any one of claims 3, 4, 5 and 6, wherein said first magnetic sensor for detecting said leakage flux is oriented to detect a component of said leakage flux which is parallel to the surface of said object.

9. A magnetic detector according to claim 5, wherein said compensating coil is wound in surrounding relation to an outer circumferential surface of said first magnetic sensor.

10. A magnetic detector according to claim 6, wherein said compensating coil is wound in surrounding relation to an outer circumferential surface of said first magnetic sensor.

11. A magnetic detector comprising:

means for generating a magnetic field;

a magnetic sensor for detecting a leakage flux resulting from a magnetically defective portion of an object moving in and relative to said magnetic field and for producing a signal corresponding thereto;

a low-pass filter for extracting a low-frequency signal component contained in said signal output by the magnetic sensor, said low-frequency signal component being indicative of a floating flux which crosses said magnetic sensor and which is a result of the object moving through said magnetic field;

an amplifier for amplifying the low-frequency signal component extracted by said low-pass filter;

a compensating coil excited by the amplified low-frequency signal component output by the amplifier, for generating a magnetic flux which cancels out said floating flux crossing said magnetic sensor;

a high-pass filter for extracting a signal resulting from the magnetically defective portion and contained in the signal that is output by said magnetic sensor;

an output amplifier for amplifying a signal output by said high-pass filter and for outputting the amplified signal as a defect signal; and amplifier control means for controlling an amplification factor of said output amplifier in accordance with a signal output by said magnetic sensor.

12. A magnetic detector comprising:

a magnetizer for generating a magnetic field;

a magnetic sensor for detecting a leakage flux resulting from a magnetically defective portion of an object moving in and relative to said magnetic field generated by said magnetizer and for producing a signal corresponding thereto, said object having a surface;

a low-pass filter for extracting a low-frequency signal component contained in said signal output by the magnetic sensor, said low-frequency signal component being indicative of a floating flux which crosses said magnetic sensor and which is a result of the object moving through said magnetic field;

an amplifier for amplifying the low-frequency signal component extracted by said low-pass filter;

a compensating coil excited by the amplified low-frequency signal component output by the amplifier, for generating a magnetic flux which cancels out said floating flux crossing said magnetic sensor;

a high-pass filter for extracting a signal resulting from the magnetically defective portion and contained in the signal that is output by said magnetic sensor;

an output amplifier for amplifying a signal output by said high-pass filter and for outputting the amplified signal as a defect signal; and magnetizer control means for controlling the intensity of the magnetic field generated by said magnetizer, in accordance with a signal output by the magnetic sensor.

13. A magnetic detector according to claims 11 or 12, wherein an integrator is connected between said low-pass filter and said amplifier.

14. A magnetic detector comprising:

a magnetizer for generating a magnetic field;

a magnetic sensor for detecting a leakage flux resulting from a magnetically defective portion of an object moving in and relative to a magnetic field generated by said magnetizer;

magnetizer control means for controlling the intensity of the said magnetic field generated by said magnetizer, in accordance with a signal output by said second magnetic sensor;

a high-pass filter for extracting a signal resulting from the magnetically defective portion and which is contained in a signal output by said magnetic sensor;

an output amplifier for amplifying a signal output by said high-pass filter and for outputting the amplified signal as a defect signal; and amplifier control means for controlling an amplification factor of said output amplifier in accordance with a signal output by said magnetic sensor.

15. A magnetic detector according to claim 14, wherein said object has a surface which extends in a plane, and said magnetic sensor for detecting said leakage flux is oriented to detect a component of said leakage flux which is parallel to said plane.

16. A magnetic detector comprising:

means for generating a magnetic field;

a magnetic sensor for detecting a leakage flux resulting from a magnetically defective portion of an object moving in and relative to said magnetic field and for producing a signal corresponding thereto;

a low-pass filter for extracting a low-frequency signal component contained in said signal output by the magnetic sensor, said low-frequency signal component being indicative of a floating flux which crosses the magnetic sensor and which is a result of the object moving through said magnetic field;

an amplifier for amplifying the low-frequency signal component extracted by the low-pass filter;

a compensating coil excited by the amplified low-frequency signal component output by the amplifier, for generating a magnetic flux which cancels out said floating flux crossing said magnetic sensor;

a high-pass filter for extracting a signal resulting from the magnetically defective portion and which is contained in the signal that is output by said magnetic sensor;

a speed detector for detecting a speed at which said object moves relative to said magnetic sensor; and frequency control means for controlling a pass frequency of said high-pass filter in accordance with the speed detected by said speed detector.

17. A magnetic detector according to claim 16, wherein said object has a surface which extends in a plane, and said magnetic sensor is oriented to detect a component of the leakage flux resulting from the magnetically defective portion of said object, which is parallel to said plane, and said compensating coil is wound in surrounding relation to an outer circumferential surface of said magnetic sensor.

18. A magnetic detector according to claim 16, further comprising:

a roll contacting said object for changing a direction in which said object is moving, and wherein said object is a moving strip; and wherein said means for generating a magnetic field includes a magnetizer opposing a portion of said object which contacts an outer circumferential surface of said roll, for generating said magnetic field.

19. A magnetic detector according to claim 18, wherein said magnetizer has a pair of magnetic poles which oppose the object contacting the outer circumferential surface of said roll, and said magnetic sensor is arranged between the magnetic poles of said magnetizer.

20. A magnetic detector according to claim 18, wherein said magnetizer has a pair of magnetic poles which oppose a portion of said roll which is to contact said object, and said magnetic sensor is arranged between the magnetic poles of said magnetizer.

21. A magnetic detector according to claim 16, wherein said compensating coil is wound in surrounding relation to an outer circumferential surface of said magnetic sensor.

22. A magnetic detector comprising:

means for generating a magnetic field;

a magnetic sensor for detecting a leakage flux resulting from a magnetically defective portion of an object moving in and relative to said magnetic field and for producing a signal corresponding thereto;

a low-pass filter for extracting a low-frequency signal component contained in said signal output by the magnetic sensor, said low-frequency signal component being indicative of a floating flux which crosses the magnetic sensor and which is a result of the object moving through said magnetic field;

an amplifier for amplifying the low-frequency signal component extracted by the low-pass filter;

a compensating coil excited by the amplified low-frequency signal component output by the amplifier, for generating a magnetic flux which cancels out said floating flux crossing said magnetic sensor;

said means for generating said magnetic field comprising a magnetizer arranged such that a pair of magnetic poles oppose said object;

said magnetic sensor being arranged on a line connecting said magnetic poles;

a high-pass filter for extracting a signal resulting from the magnetically defective portion and which is contained in the signal that is output by said magnetic sensor;

a speed detector for detecting a speed at which said object moves relative to said magnetic sensor; and frequency control means for controlling a pass frequency of said high-pass filter in accordance with the speed detected by said speed detector.

23. A magnetic detector according to claim 22, wherein said compensating coil is wound in surrounding relation to an outer circumferential surface of said magnetic sensor.

24. A magnetic detector comprising:

means for generating a magnetic field;

a first magnetic sensor for detecting a leakage flux resulting from a magnetically defective portion of an object moving in and relative to said magnetic field, said object having a surface;

a high-pass filter for extracting a signal resulting from the magnetically defective portion and which is contained in the signal that is output by said first magnetic sensor;

an output amplifier for amplifying a signal output by said high-pass filter and for outputting the amplified signal as a defect signal;

a second magnetic sensor located near said first magnetic sensor, for detecting a component of said magnetic field which is parallel to the surface of said object;

amplifier control means for controlling an amplification factor of said output amplifier in accordance with a signal output by said second magnetic sensor;

a reference signal generating circuit for generating a reference signal corresponding to a reference amplification factor; and a division circuit connected between said second magnetic sensor and said output amplifier for detecting that component of said magnetic field which is parallel to the surface of said object, and for dividing a signal output by said second magnetic sensor by said reference signal for controlling amplification of said output amplifier.

25. A magnetic detector according to claim 24, wherein a compensating coil is wound in surrounding relation to an outer circumferential surface of said first magnetic sensor.

26. A magnetic detector comprising:

a magnetizer for generating a magnetic field;

a first magnetic sensor for detecting a leakage flux resulting from a magnetically defective portion of an object moving in and relative to said magnetic field generated by said magnetizer, said object having a surface;

said first magnetic sensor outputting a first output signal that is indicative of the magnetically defective portion of the object;

a second magnetic sensor located near said first magnetic sensor, for detecting a component of said magnetic field which is parallel to the surface of said object;

magnetizer control means for controlling an intensity of said magnetic field generated by said magnetizer, in accordance with a signal output by the second magnetic sensor;

a high-pass filter for extracting a signal resulting from the magnetically defective portion of the object and which is contained in the first output signal output by said first magnetic sensor;

an output amplifier for amplifying the first signal output by said first magnetic sensor and for outputting an amplified signal as a defect signal; and amplifier control means for controlling an amplification factor of said output amplifier in accordance with a signal output by said second magnetic sensor for detecting said component of said magnetic field which is parallel to the surface of said object.

27. A magnetic detector according to claim 26, wherein the first output signal output from the first magnetic sensor is amplified by an amplifier.

28. A magnetic detector according to claim 26, wherein a compensating coil is wound in surrounding relation to an outer circumferential surface of said first magnetic sensor.

* * * * *